(12) United States Patent
Ma et al.

(10) Patent No.: US 9,512,355 B2
(45) Date of Patent: *Dec. 6, 2016

(54) ORGANIC LIGHT EMITTING MATERIALS

(75) Inventors: Bin Ma, Ewing, NJ (US); Alan DeAngelis, Pennington, NJ (US); Chuanjun Xia, Lawrenceville, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 1219 days.

This patent is subject to a terminal disclaimer.

(21) Appl. No.: 13/316,162

(22) Filed: Dec. 9, 2011

(65) Prior Publication Data

US 2013/0146848 A1   Jun. 13, 2013

(51) Int. Cl.

| H01L 51/54 | (2006.01) |
|---|---|
| C09K 11/06 | (2006.01) |
| C07F 15/00 | (2006.01) |
| H05B 33/14 | (2006.01) |
| H01L 51/00 | (2006.01) |
| H01L 51/50 | (2006.01) |

(52) U.S. Cl.
CPC ........... *C09K 11/06* (2013.01); *C07F 15/0033* (2013.01); *H01L 51/0085* (2013.01); *H05B 33/14* (2013.01); *C09K 2211/1029* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| 4,769,292 A | 9/1988 | Tang et al. |
|---|---|---|
| 5,061,569 A | 10/1991 | VanSlyke et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |

(Continued)

FOREIGN PATENT DOCUMENTS

| CN | 100375749 | 3/2008 |
|---|---|---|
| CN | 100584811 | 1/2010 |

(Continued)

OTHER PUBLICATIONS

Machine translation of KR 2011-0077350 (Jul. 2011).*

(Continued)

*Primary Examiner* — Marie R. Yamnitzky
(74) *Attorney, Agent, or Firm* — Duane Morris LLP

(57) ABSTRACT

Novel phosphorescent metal complexes containing 2-phenylisoquinoline ligands with at least two substituents on the isoquinoline ring are provided. The disclosed compounds have low sublimation temperatures that allow for ease of purification and fabrication into a variety of OLED devices.

20 Claims, 3 Drawing Sheets

Formula I

(56) References Cited

U.S. PATENT DOCUMENTS

| | | | |
|---|---|---|---|
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 8,492,006 | B2 * | 7/2013 | Ma et al. ............ 428/690 |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0152802 | A1 | 8/2003 | Tsuboyama et al. |
| 2003/0162053 | A1 | 8/2003 | Marks et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0137267 | A1 | 7/2004 | Igarashi et al. |
| 2004/0137268 | A1 | 7/2004 | Igarashi et al. |
| 2004/0174116 | A1 | 9/2004 | Lu et al. |
| 2005/0025993 | A1 | 2/2005 | Thompson et al. |
| 2005/0112407 | A1 | 5/2005 | Ogasawara et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0202194 | A1 | 9/2006 | Jeong et al. |
| 2006/0240279 | A1 | 10/2006 | Adamovich et al. |
| 2006/0251923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2008/0015355 | A1 | 1/2008 | Schafer et al. |
| 2008/0018221 | A1 | 1/2008 | Egen et al. |
| 2008/0074033 | A1 | 3/2008 | Ionkin et al. |
| 2008/0106190 | A1 | 5/2008 | Yabunouchi et al. |
| 2008/0124572 | A1 | 5/2008 | Mizuki et al. |
| 2008/0220265 | A1 | 9/2008 | Xia et al. |
| 2008/0261076 | A1 | 10/2008 | Kwong et al. |
| 2008/0297033 | A1 | 12/2008 | Knowles et al. |
| 2009/0008605 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0045731 | A1 | 2/2009 | Nishimura et al. |
| 2009/0048415 | A1 | 2/2009 | Buesing et al. |
| 2009/0101870 | A1 | 4/2009 | Prakash et al. |
| 2009/0108737 | A1 | 4/2009 | Kwong et al. |
| 2009/0115316 | A1 | 5/2009 | Zheng et al. |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |
| 2011/0127501 | A1 | 6/2011 | Lecloux et al. |

FOREIGN PATENT DOCUMENTS

| | | |
|---|---|---|
| CN | 102187491 | 9/2011 |
| EP | 0650955 | 5/1995 |
| EP | 1535981 | 6/2005 |
| EP | 1725079 | 11/2006 |
| EP | 1784057 | 5/2007 |
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 2009507865 | 2/2009 |
| KR | 20110077350 | 7/2011 |
| KR | 1020110077173 | 7/2011 |
| WO | WO 0139234 | 5/2001 |
| WO | WO 0202714 | 1/2002 |
| WO | WO 0215645 | 2/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005019373 | 3/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006072002 | 7/2006 |
| WO | WO 2006082742 | 8/2006 |
| WO | WO 2006098120 | 9/2006 |
| WO | WO 2006100298 | 9/2006 |
| WO | WO 2006103874 | 10/2006 |
| WO | WO 2006114966 | 11/2006 |
| WO | WO 2006132173 | 12/2006 |
| WO | WO 2007002683 | 1/2007 |
| WO | WO 2007004380 | 1/2007 |
| WO | WO 2007063754 | 6/2007 |
| WO | WO 2007063796 | 6/2007 |
| WO | WO 2008056746 | 5/2008 |
| WO | WO 2006056418 | 6/2008 |
| WO | WO 2008101842 | 8/2008 |
| WO | WO 2008132085 | 11/2008 |
| WO | WO 2009000673 | 12/2008 |
| WO | WO 2009003898 | 1/2009 |
| WO | WO 2009008311 | 1/2009 |
| WO | WO 2009018009 | 2/2009 |
| WO | WO 2009021126 | 2/2009 |
| WO | WO 2009050290 | 4/2009 |
| WO | WO 2009062578 | 5/2009 |
| WO | WO 2009063833 | 5/2009 |
| WO | WO 2009066778 | 5/2009 |
| WO | WO 2009066779 | 5/2009 |
| WO | WO 2009086028 | 7/2009 |
| WO | WO 2009100991 | 8/2009 |

OTHER PUBLICATIONS

Notification of First Office Action issued in corresponding Chinese Patent Application No. 201210519745.X, (dated Nov. 3, 2014).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenyl-amino)triphenylamine (m-MTDATA), as Hole-Transport Materials," *Adv. Mater.*, 6(9):677-679 (1994).

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral $Ru^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSLYKE, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

(56) References Cited

OTHER PUBLICATIONS

Ma, Yuguang et al., "Triplet Luminescent Dinuclear-Gold(I) Complex-Based Light-Emitting Diodes with Low Turn-On voltage," *Appl. Phys. Lett.*, 74(10)1361-1363 (1999).
Gao, Zhiqiang et al., "Bright-Blue Electroluminescence From a Silyl-Substituted ter-(phenylene-vinylene) derivative," *Appl. Phys. Lett.*, 74(6):865-867 (1999).
Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15)2280-2282 (2000).
Hung, L.S. et al., "Anode Modification in Organic Light-Emitting Diodes by Low-Frequency Plasma Polymerization of $CHF_3$," *Appl. Phys. Lett.*, 78(5):673-675 (2001).
Ikai, Masamichi et al., "Highly Efficient Phosphorescence From Organic Light-Emitting Devices with an Exciton-Block Layer," *Appl. Phys. Lett.*, 79(2):156-158 (2001).
Wang, Y. et al., "Highly Efficient Electroluminescent Materials Based on Fluorinated Organometallic Iridium Compounds," *Appl. Phys. Lett.*, 79(4):449-451 (2001).
Kwong, Raymond C. et al., "High Operational Stability of Electrophosphorescent Devices," *Appl. Phys. Lett.*, 81(1)162-164 (2002).
Holmes, R.J. et al., "Blue Organic Electrophosphorescence Using Exothermic Host-Guest Energy Transfer," *Appl. Phys. Lett.*, 82(15):2422-2424 (2003).
Sotoyama, Wataru et al., "Efficient Organic Light-Emitting Diodes with Phosphorescent Platinum Complexes Containing NÔCÔN-Coordinating Tridentate Ligand," *Appl. Phys. Lett.*, 86:153505-1-153505-3 (2005).
Okumoto, Kenji et al., "Green Fluorescent Organic Light-Emitting Device with External Quantum Efficiency of Nearly 10%," *Appl. Phys. Lett.*, 89:063504-1-063504-3 (2006).
Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).
Aonuma, Masaki et al., "Material Design of Hole Transport Materials Capable of Thick-Film Formation in Organic Light Emitting Diodes," *Appl. Phys. Lett.*, 90:183503-1-183503-3 (2007).
Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).
Adachi, Chihaya et al., "High-Efficiency Red Electrophosphorescence Devices," *Appl. Phys. Lett.*, 78(11)1622-1624 (2001).
Wong, Keith Man-Chung et al.;"A Novel Class of Phosphorescent Gold(III) Alkynyl-Based Organic Light-Emitting Devices with Tunable Colour," *Chem. Commun.*, 2906-2908 (2005).
Hamada, Yuji et al., "High Luminance in Organic Electroluminescent Devices with Bis(10-hydroxybenzo[h]quinolinato)beryllium as an Emitter," *Chem. Lett.*, 905-906 (1993).
Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).
Mi, Bao-Xiu et al., "Thermally Stable Hole-Transporting Material for Organic Light-Emitting Diode: an Isoindole Derivative," *Chem. Mater.*, 15(16):3148-3151 (2003).
Huang, Wei-Sheng et al., "Highly Phosphorescent Bis-Cyclometalated Iridium Complexes Containing Benzoimidazole-Based Ligands," *Chem. Mater.*, 16(12):2480-2488 (2004).
Niu, Yu-Hua et al., "Highly Efficient Electrophosphorescent Devices with Saturated Red Emission from a Neutral Osmium Complex," *Chem. Mater.*, 17(13):3532-3536 (2005).
Lo, Shih-Chun et al., "Blue Phosphorescence from Iridium(III) Complexes at Room Temperature," *Chem. Mater.*, 18(21):5119-5129 (2006).
Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).
Lamansky, Sergey et al., "Synthesis and Characterization of Phosphorescent Cyclometalated Iridium Complexes," *Inorg. Chem.*, 40(7):1704-1711 (2001).
Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).
Noda, Tetsuya and Shirota,Yasuhiko, "5,5'-Bis(dimesitylboryl)-2,2'-bithlophene and 5,5"- Bis(dimesitylboryl)-2,2':5',2"-terthiophene as a Novel Family of Electron-Transporting Amorphous Molecular Materials," *J. Am. Chem. Soc.*, 120 (37):9714-9715 (1998).
Sakamoto, Youichi et al., "Synthesis, Characterization, and Electron-Transport Property of Perfluorinated Phenylene Dendrimers," *J. Am. Chem. Soc.*, 122(8):1832-1833 (2000).
Adachi, Chihaya et al., "Nearly 100% Internal Phosphorescence Efficiency in an Organic Light Emitting Device," *J. Appl. Phys.*, 90(10):5048-5051 (2001).
Shirota, Yasuhiko at al., "Starburst Molecules Based on π-Electron Systems as Materials for Organic Electroluminescent Devices," *Journal of Luminescence*, 72-74:985-991 (1997).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).
Kido, Junji et al.,"1,2,4-Triazole Derivative as an Electron Transport Layer in Organic Electroluminescent Devices," *Jpn. J. Appl. Phys.*, 32:L917-L920 (1993).
Van Slyke, S. A. et al., "Organic Electroluminescent Devices with Improved Stability," *Appl. Phys. Lett.*, 69(15 ):2160-2162 (1996).
Guo, Tzung-Fang et al., "Highly Efficient Electrophosphorescent Polymer Light-Emitting Devices," *Organic Electronics*, 1:15-20 (2000).
Palilis, Leonidas C., "High Efficiency Molecular Organic Light-Emitting Diodes Based On Silole Derivatives and Their Exciplexes," *Organic Electronics*, 4:113-121 (2003).
Ikeda, Hisao et al., "P-185: Low-Drive-Voltage OLEDs with a Buffer Layer Having Molybdenum Oxide," *SID Symposium Digest*, 37:923-926 (2006).
T. Östergård et al., "Langmuir-Blodgett Light-Emitting Diodes of Poly(3-Hexylthiophene): Electro-Optical Characteristics Related to Structure," *Synthetic Metals*, 87:171-177 (1997).
Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).
Salbeck, J. et al., "Low Molecular Organic Glasses for Blue Electroluminescence," *Synthetic Metals*, 91:209-215 (1997).
Baldo et al., "Highly Efficient Phosphorescent Emission from Organic Electroluminescent Devices," Nature, vol. 395, 151-154, (1998).
Baldo et al., "Very high-efficiency green organic light-emitting devices based on electrophosphorescence," Appl. Phys. Lett., vol. 75, No. 4-6 (1999).
Notice of Reasons for Rejection issued Nov. 16, 2015 for corresponding JP Application No. 2012-268175.
Decision of Rejection issued Jun. 6, 2016 for corresponding JP Application No. 2012-268175.
European Search Report issued Jan. 8, 2015 for corresponding EP Application No. 12196136.1.

* cited by examiner

Formula I

ORGANIC LIGHT EMITTING MATERIALS

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to metal complexes containing heterocyclic ligands with at least two substituents on the heterocyclic ligand. These metal complexes are suitable for use in OLED devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the following structure:

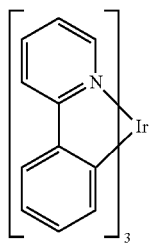

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

In one aspect, a compound having the formula:

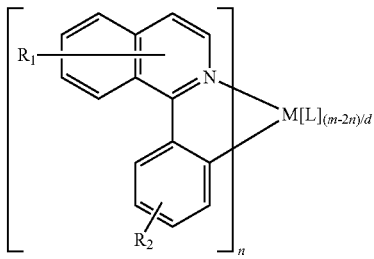

Formula I is provided.

In the compound of Formula I, M is a metal having an atomic weight higher than 40, L is a second ligand, m is the maximum coordination number of the metal M, d is the denticity of L, and n is at least 1. $R_1$ is independently selected for each ligand and represents di, tri, tetra, penta substitutions, or no substitution. Each of $R_1$ is independently selected from the group consisting of hydrogen, deuterium, halide, alkyl, cycloalkyl, heteroalkyl, arylalkyl, alkoxy, aryloxy, amino, silyl, germyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

At least two of $R_1$ is independently selected from two to six carbon containing alkyl, silyl, germyl, cycloalkyl, and combinations thereof. $R_2$ may represent mono, di, tri, tetra substitutions, or no substitution, and each of $R_2$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $R_1$ represents di-substitution. In one aspect, $R_1$ represents di-alkyl substitution. In another aspect, $R_1$ represents silyl or germyl substitution.

In one aspect, the compound has the formula:

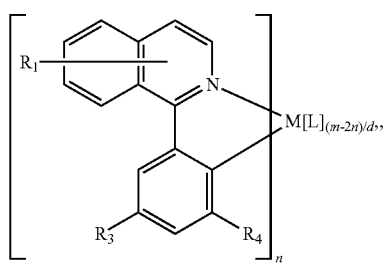

Formula II wherein $R_3$ and $R_4$ are alkyl.

In one aspect, the compound has the formula:

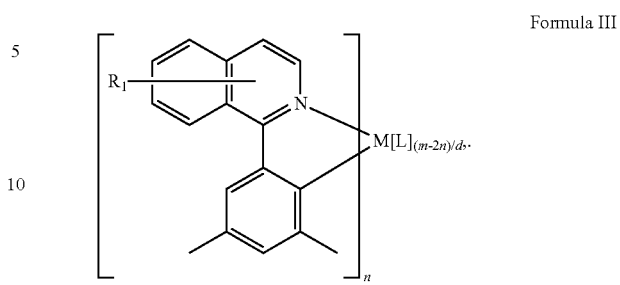

Formula III

In one aspect, $R_1$ is independently selected from the group consisting of $CH(CH_3)_2$, $CH_2CH(CH_3)_2$, $CH_2C(CH_3)_3$, cyclopentyl, cyclohexyl, ethyl, trimethylsilyl, triethylsilyl, triisopropylsilyl, trimethylgermyl, triethylgermyl, and triisopropylgermyl.

In one aspect, n M is Ir. In one aspect, n is 2. In one aspect, L is a monoanionic bidentate ligand. In one aspect, L is

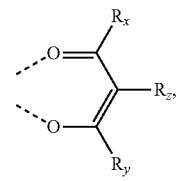

and $R_x$, $R_y$, and $R_z$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $R_x$, $R_y$, and $R_z$ are independently selected from the group consisting of alkyl, hydrogen, deuterium, and combinations thereof.

In one aspect, $R_z$ is hydrogen or deuterium, and $R_x$ and $R_y$ are independently selected from the group consisting of methyl, $CH(CH_3)_2$, and $CH_2CH(CH_3)_2$.

In one aspect, the compound has the formula:

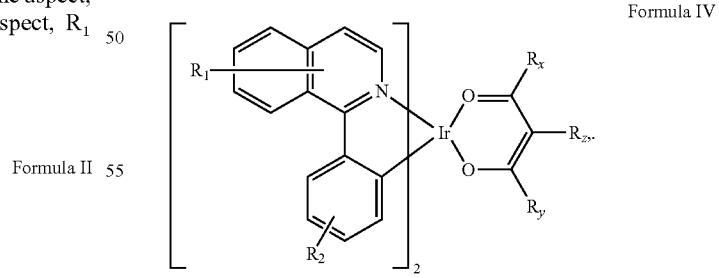

Formula IV

In one aspect, the compound is selected from Compound 1-Compound 50.

In one aspect, a first device is provided. The first device comprises a first organic light emitting device, further comprising an anode, a cathode, and an organic layer, disposed between the anode and the cathode, comprising a compound having the formula:

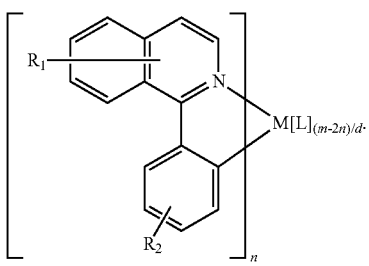

Formula I

In the compound of Formula I, M is a metal having an atomic weight higher than 40, L is a second ligand, m is the maximum coordination number of the metal M, d is the denticity of L, and n is at least 1. $R_1$ is independently selected for each ligand and represents di, tri, tetra, penta substitutions, or no substitution. Each of $R_1$ is independently selected from the group consisting of hydrogen, deuterium, halide, alkyl, cycloalkyl, heteroalkyl, arylalkyl, alkoxy, aryloxy, amino, silyl, germyl, alkenyl, cycloalkenyl; heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

At least two of $R_1$ is independently selected from two to six carbon containing alkyl, silyl, germyl, cycloalkyl, and combinations thereof. $R_2$ may represent mono, di, tri, tetra substitutions, or no substitution, and each of $R_2$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the first device is a consumer product. In one aspect, the first device is an organic light-emitting device. In one aspect, the organic layer is an emissive layer and the compound is a non-emissive dopant. In one aspect, the organic layer further comprises a host.

In one aspect, the host is a metal 8-hydroxyquinolate.

In one aspect, the host is selected from the group consisting of:

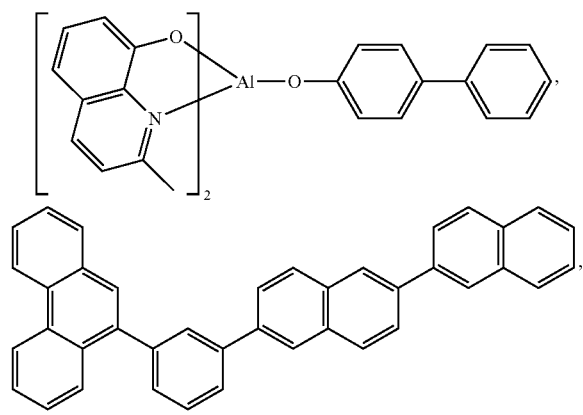

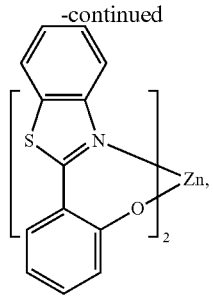

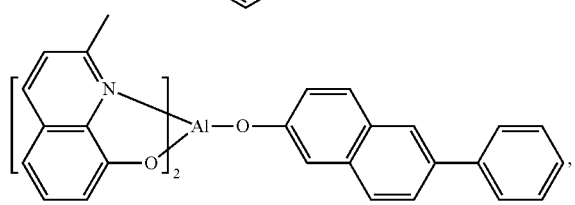

and combinations thereof.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
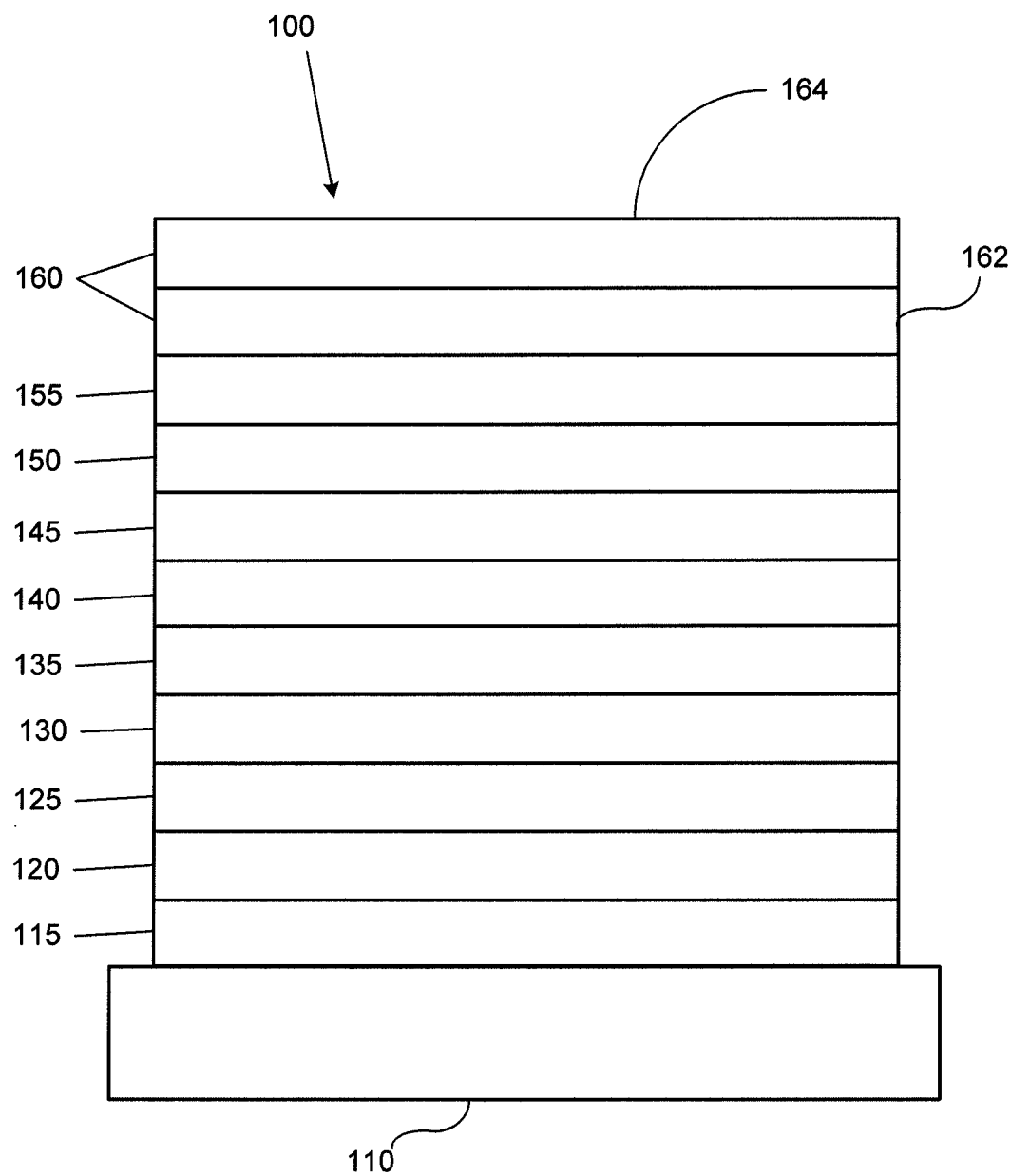
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
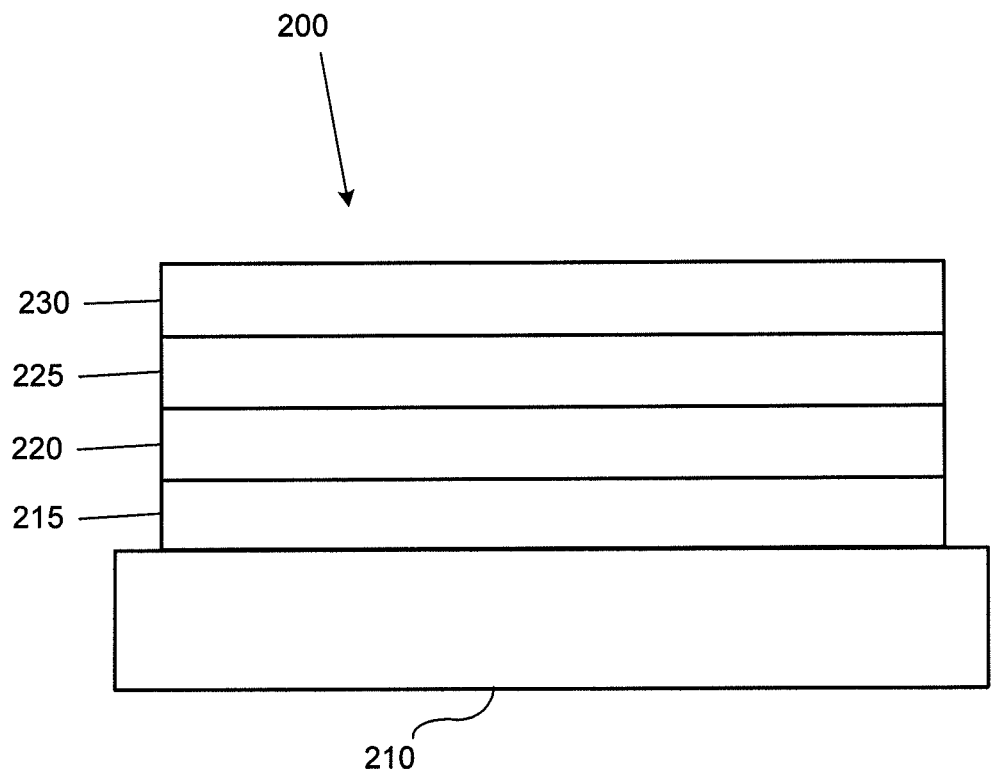
FIG. 2 shows an inverted organic light emitting device that does not have a separate electron transport layer.
Figure 3:
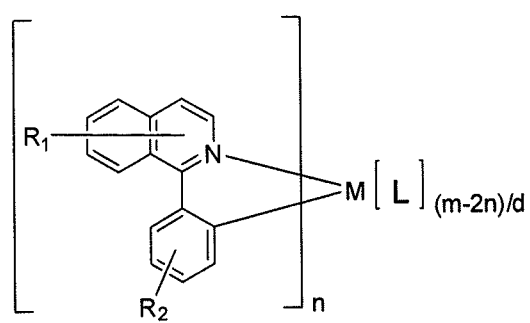
FIG. 3 shows a compound of Formula I.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 now U.S. Pat. No. 7,431,968, to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

In one embodiment, a compound having the formula:

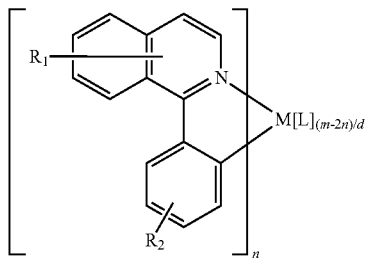

Formula I is provided.

In the compound of Formula I, M is a metal having an atomic weight higher than 40, L is a second ligand, m is the maximum coordination number of the metal M, d is the denticity of L, and n is at least 1. By "denticity" it is meant that d numerically represents the number of bonds a second ligand L makes with metal M. Thus, if L is a monodentate ligand, then d is 1, if L is a bidentate ligand, d is 2, etc. L can be one or more ligands, and when L represents more than one ligand, the ligands can be the same or different.

$R_1$ is independently selected for each ligand and represents di, tri, tetra, penta substitutions, or no substitution. Each of $R_1$ is independently selected from the group consisting of hydrogen, deuterium, halide, alkyl, cycloalkyl, heteroalkyl, arylalkyl, alkoxy, aryloxy, amino, silyl, germyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

At least two of $R_1$ is independently selected from two to six carbon containing alkyl, silyl, germyl, cycloalkyl, and combinations thereof. $R_2$ may represent mono, di, tri, tetra substitutions, or no substitution, and each of $R_2$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

It has been unexpectedly discovered that substitution at two or more of positions (i.e. $R_1$ represents at least di-substitution) on the heterocyclic ring in the compound of Formula I results in compounds with desirable properties. These properties enable OLED devices that incorporate compounds of Formula I to have improved properties such as higher efficiency and longer lifetime. Substitution of two or more positions as described above also results in compounds with lowered sublimation temperatures despite the fact that these compounds have higher molecular weights than unsubstituted or mono-substituted compounds, where the mono-substitution is on the heterocyclic ring. Without being bound by theory, it is believed that this decrease in sublimation temperature may be the result of decreased or less efficient molecular stacking in the solid state, thereby decreasing the energy required to disrupt the crystal lattice and resulting in decreased sublimation temperatures. Lower sublimation temperatures advantageously allow for easier purification of compounds of Formula I and better thermal stability in manufacturing.

In one embodiment, $R_1$ represents di-substitution. In one embodiment, $R_1$ represents di-alkyl substitution. In another embodiment, $R_1$ represents silyl or germyl substitution.

In one embodiment, the compound has the formula:

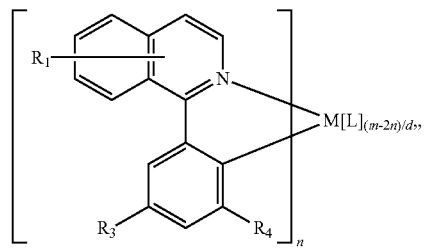

Formula II wherein $R_3$ and $R_4$ are alkyl.

In one embodiment, the compound has the formula:

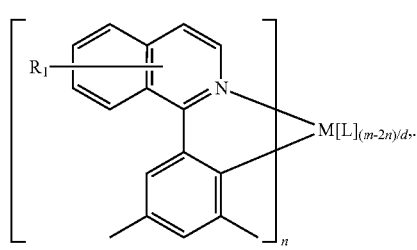

Formula III

In one embodiment, $R_1$ is independently selected from the group consisting of $CH(CH_3)_2$, $CH_2CH(CH_3)_2$, $CH_2C(CH_3)_3$, cyclopentyl, cyclohexyl, ethyl, trimethylsilyl, triethylsilyl, triisopropylsilyl, trimethylgermyl, triethylgermyl, and triisopropylgermyl.

In one embodiment, n M is Ir. In one embodiment, n is 2. In one embodiment, L is a monoanionic bidentate ligand. In one embodiment, L is

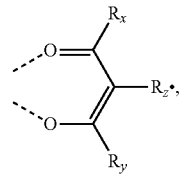

and $R_x$, $R_y$, and $R_z$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, $R_x$, $R_y$, and $R_z$ are independently selected from the group consisting of alkyl, hydrogen, deuterium, and combinations thereof.

In one embodiment, $R_z$ is hydrogen or deuterium, and $R_x$ and $R_y$ are independently selected from the group consisting of methyl, $CH(CH_3)_2$, and $CH_2CH(CH_3)_2$.

In one embodiment, the compound has the formula:

Formula IV

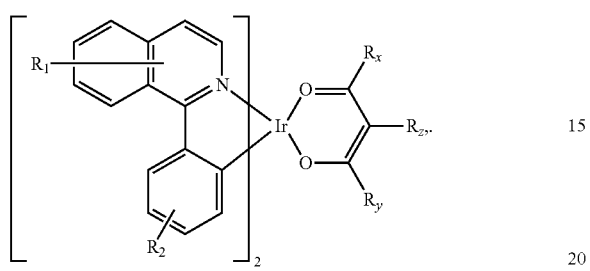

In one embodiment, the compound is selected from the group consisting of:

Compound 1

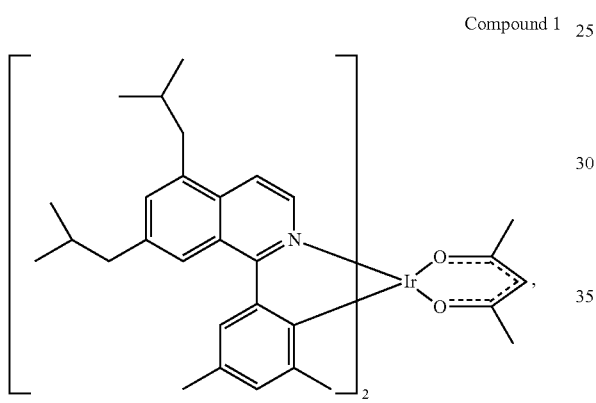

Compound 2

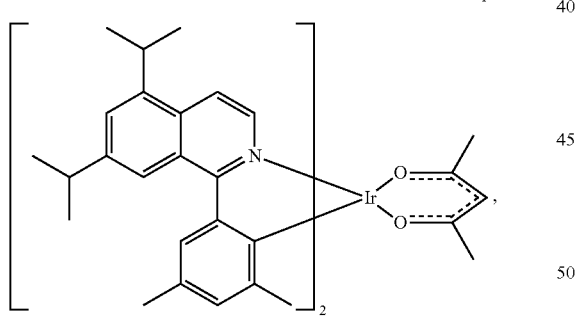

Compound 3

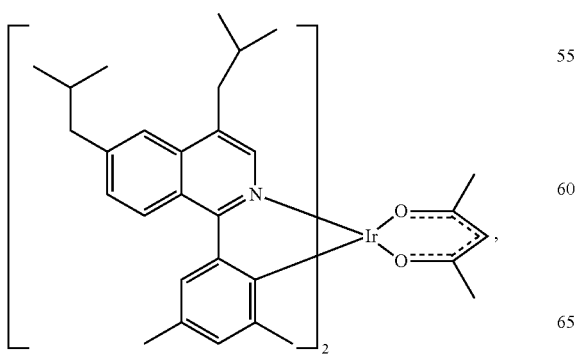

Compound 4

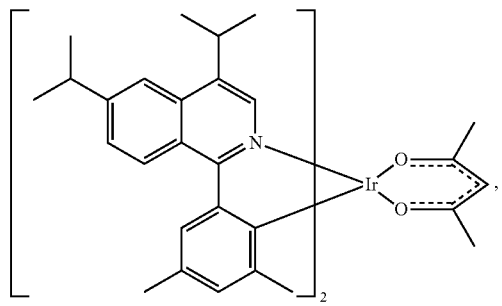

Compound 5

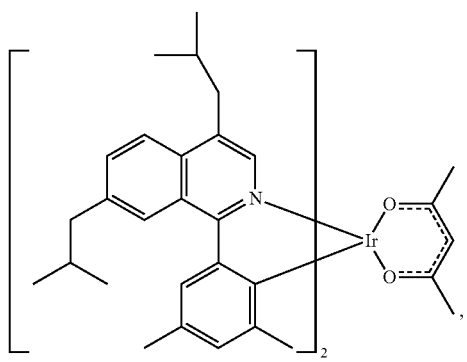

Compound 6

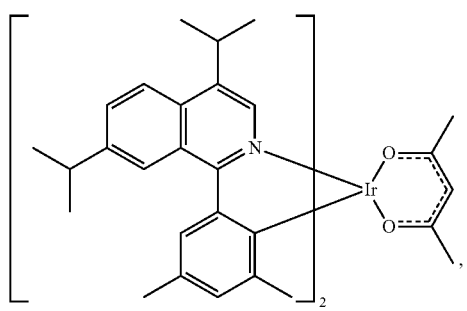

Compound 7

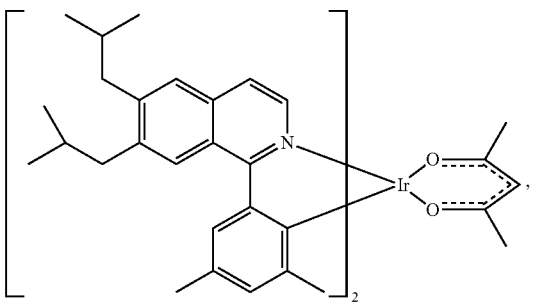

Compound 8
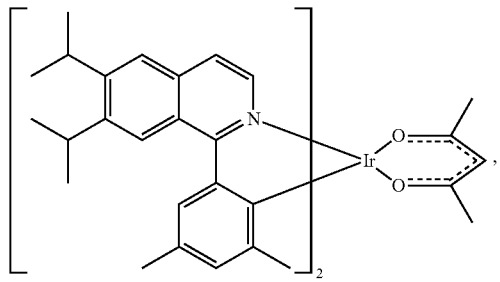
Compound 9
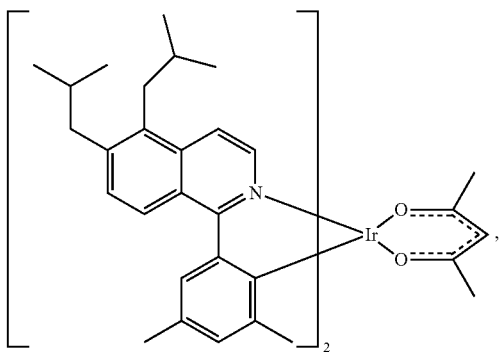
Compound 10
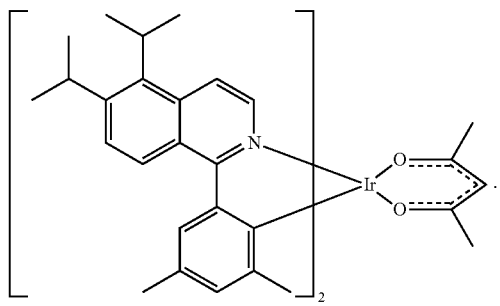
Compound 11
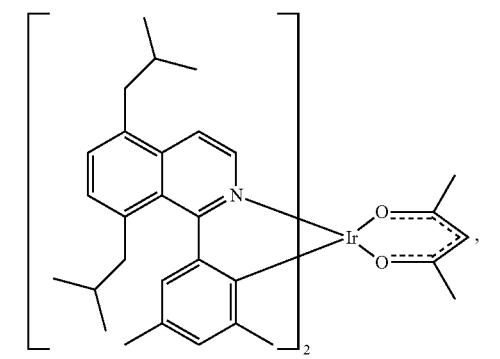
Compound 12
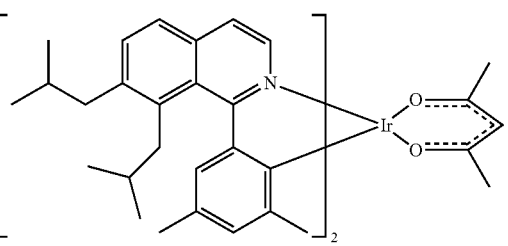
Compound 13
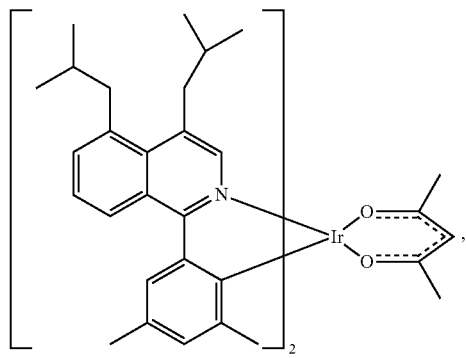
Compound 14
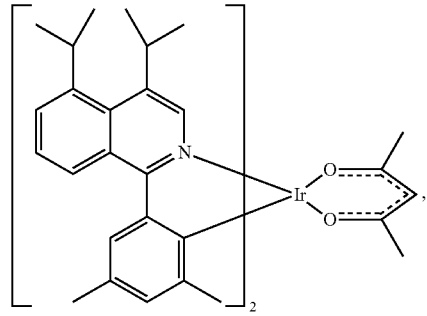
Compound 15
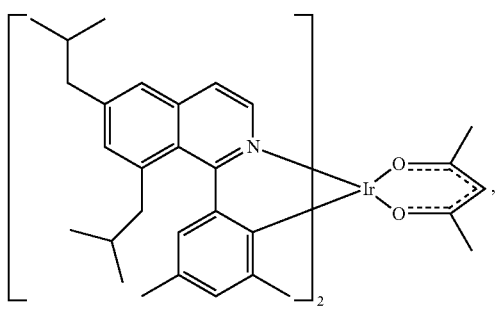
Compound 16
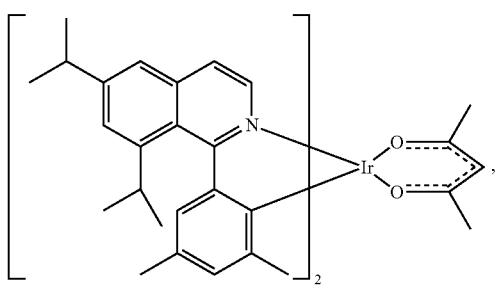

-continued
Compound 17
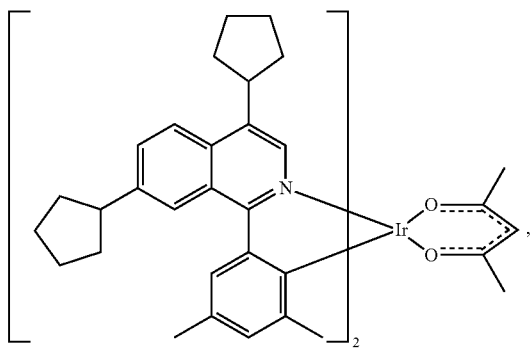
Compound 18
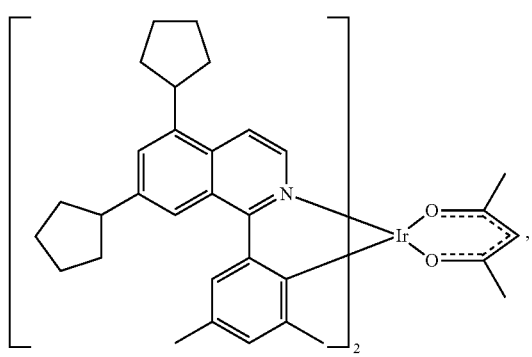
Compound 19
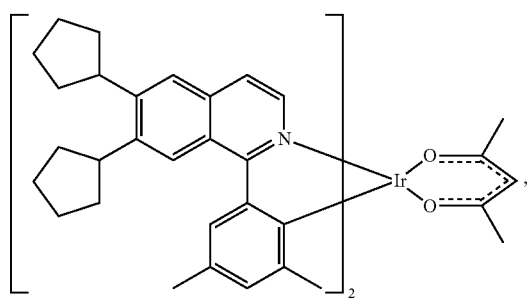
Compound 20
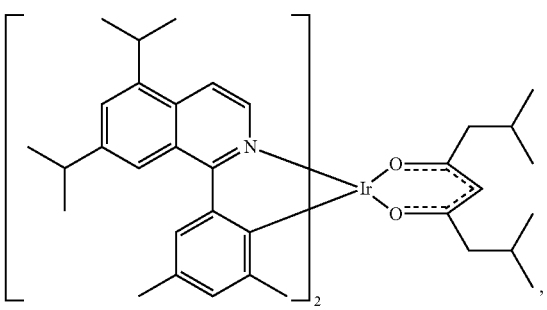
-continued
Compound 21
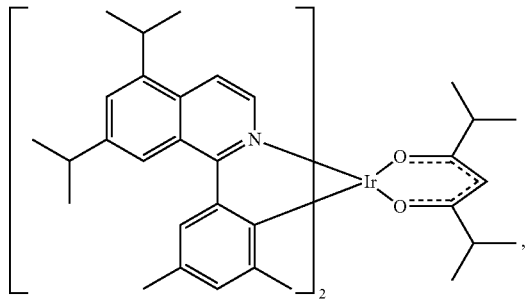
Compound 22
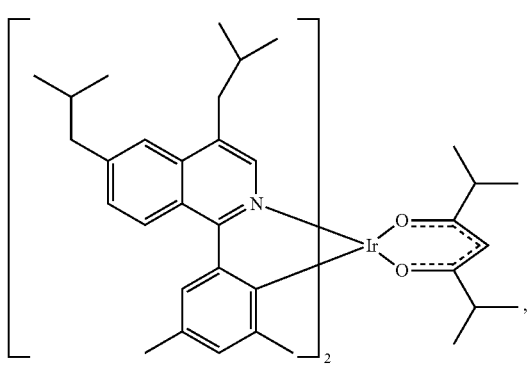
Compound 23
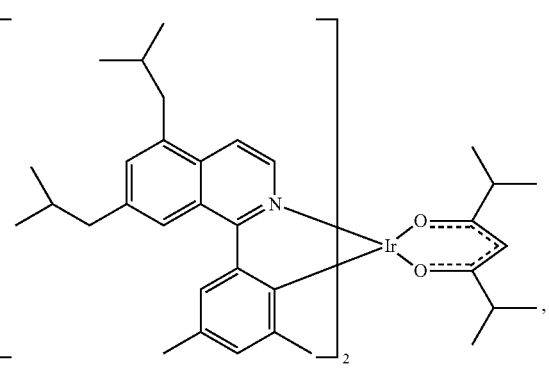
Compound 24
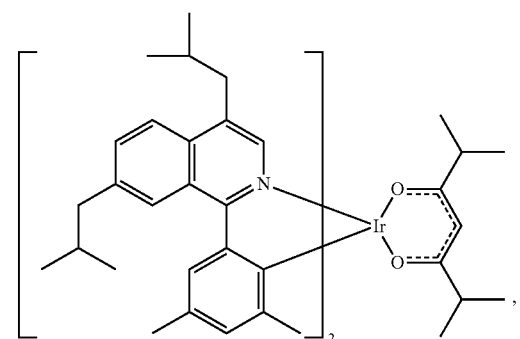

Compound 25
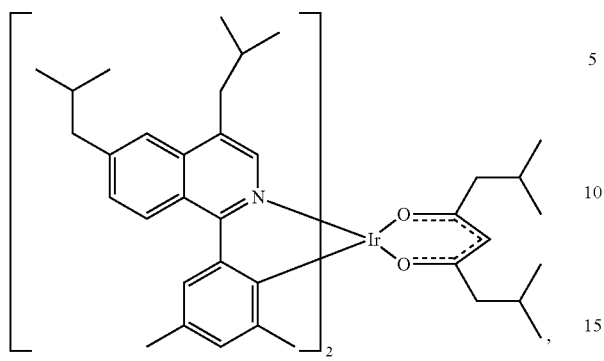
Compound 26
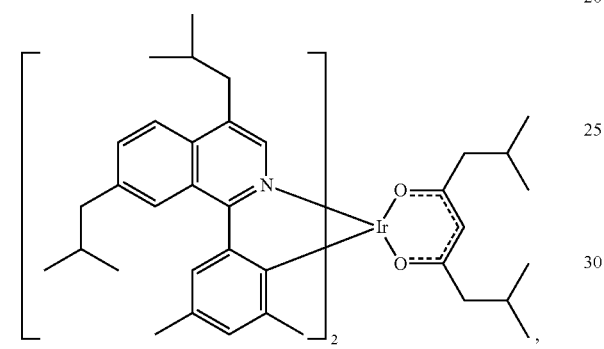
Compound 27
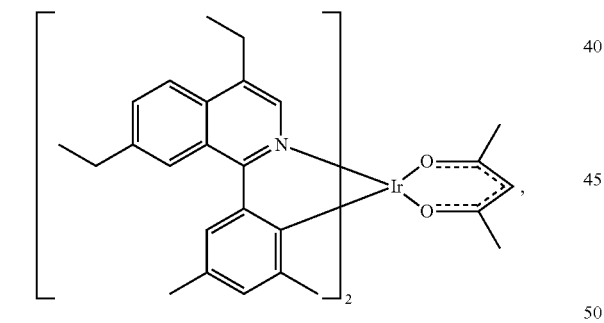
Compound 28
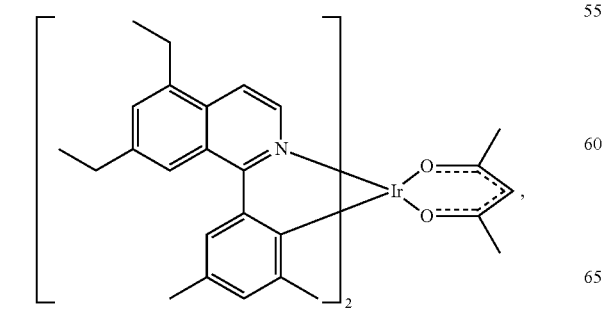
Compound 29
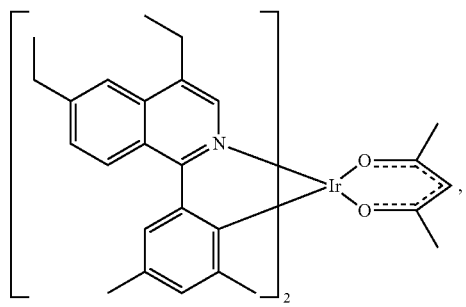
Compound 30
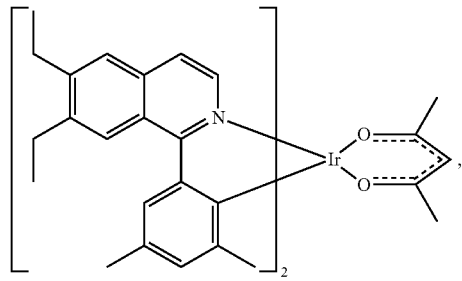
Compound 31
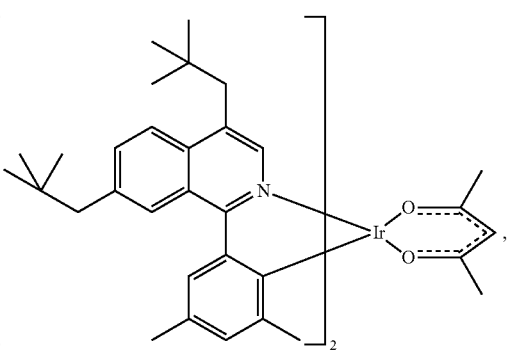
Compound 32
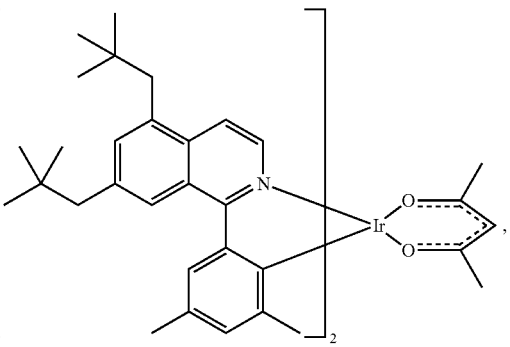

Compound 33
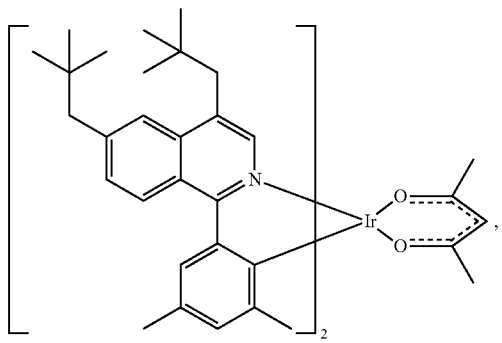
Compound 34
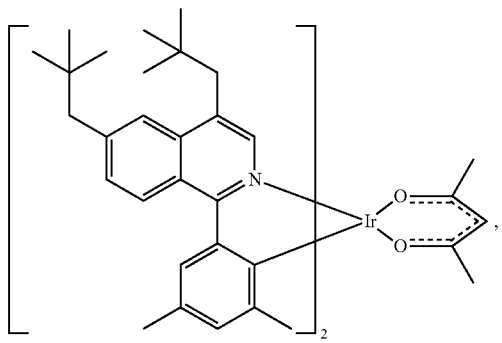
Compound 34
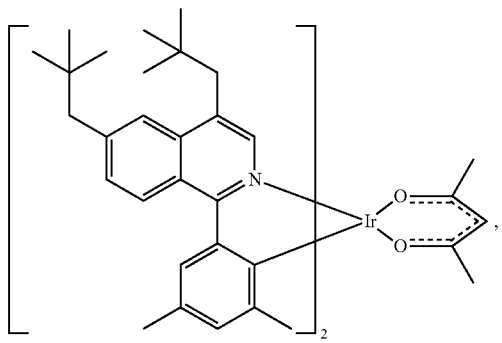
Compound 36
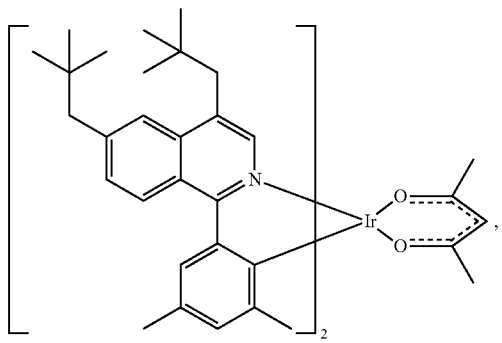
Compound 37
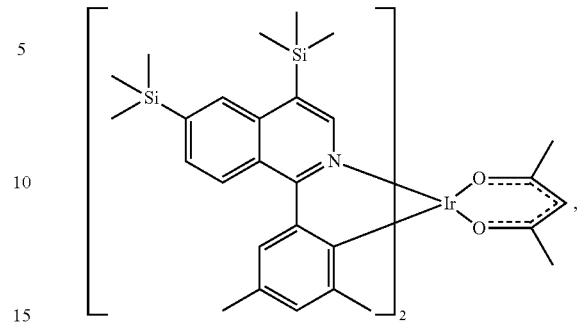
Compound 38
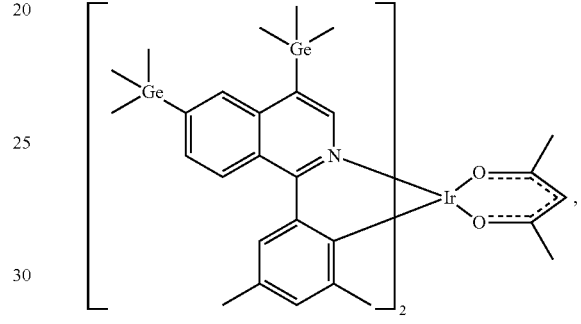
Compound 39
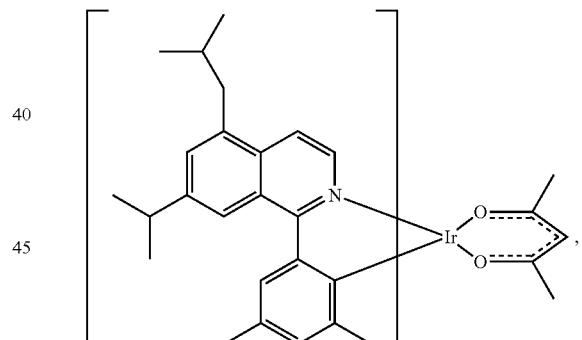
Compound 40
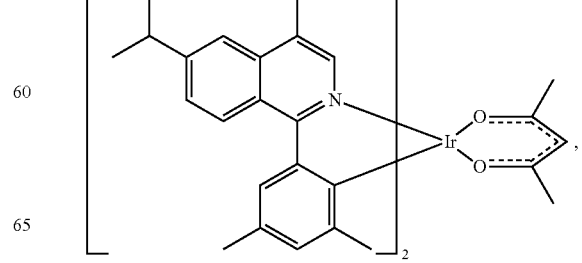

Compound 41
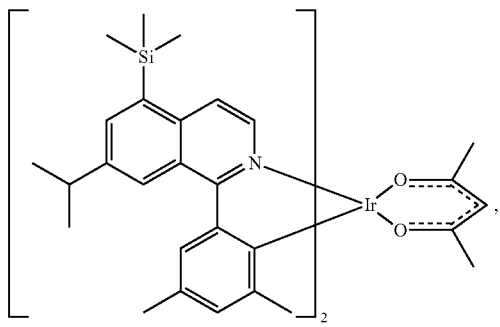
Compound 42
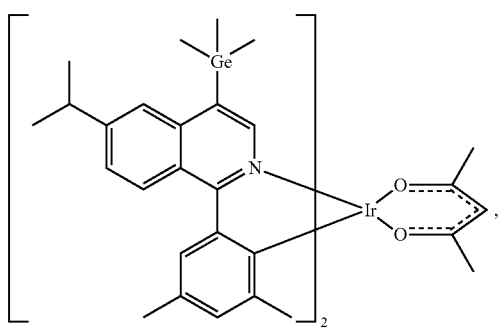
Compound 43
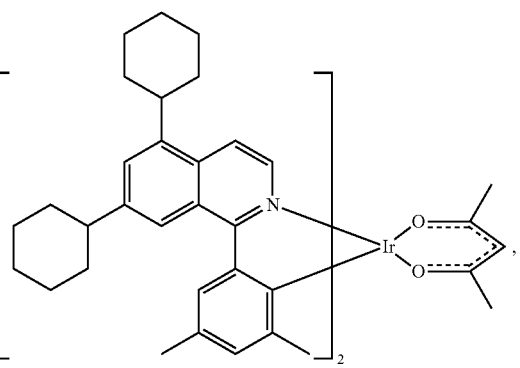
Compound 44
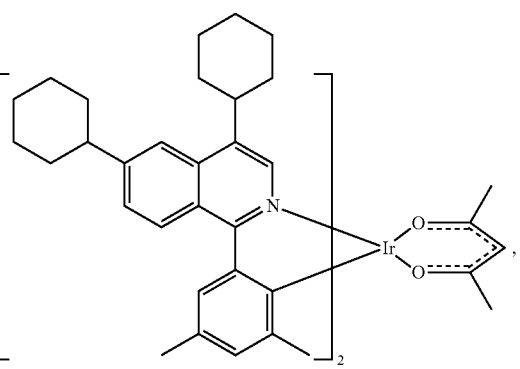
Compound 45
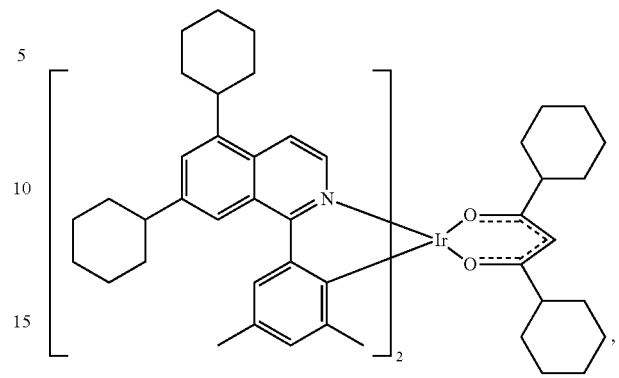
Compound 46
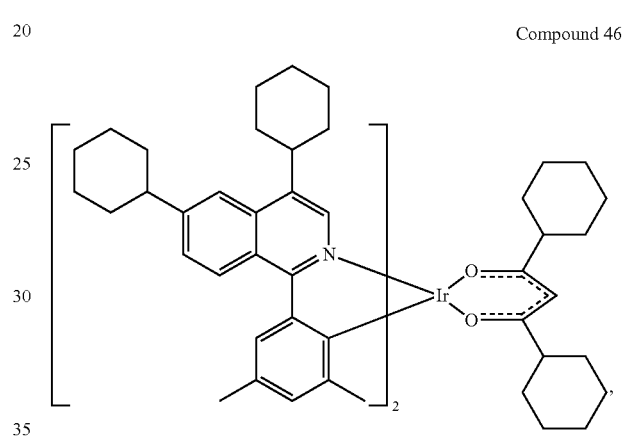
Compound 47
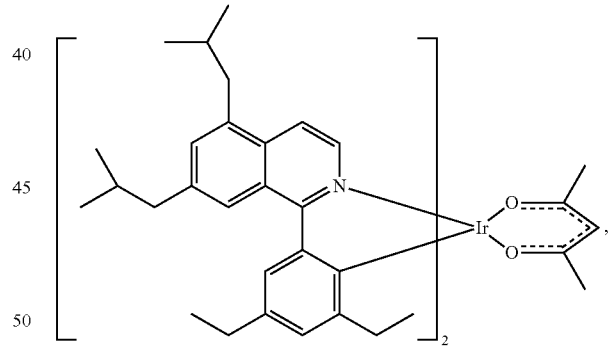
Compound 48
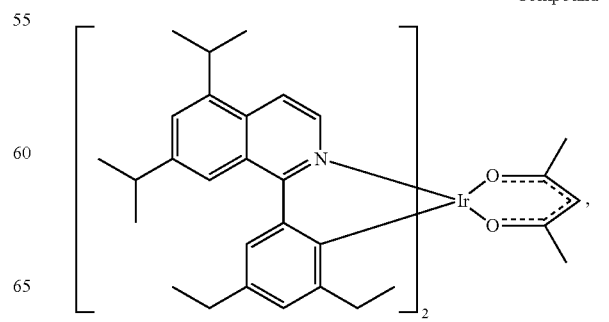

-continued

Compound 49

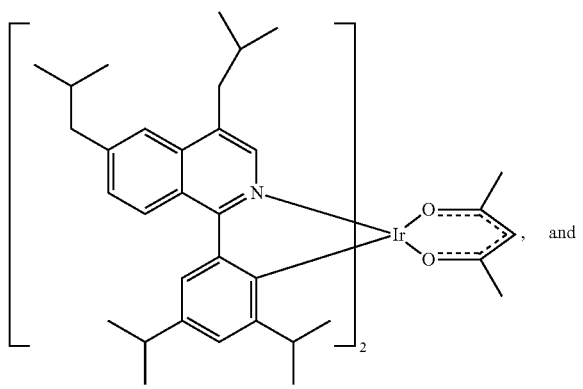

Compound 50

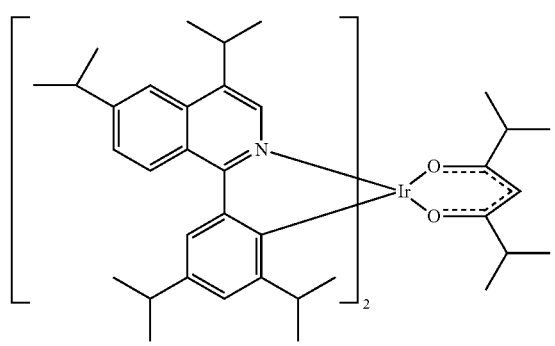

In one embodiment, a first device is provided. The first device comprises a first organic light emitting device, further comprising an anode, a cathode, and an organic layer, disposed between the anode and the cathode, comprising a compound having the formula:

Formula I

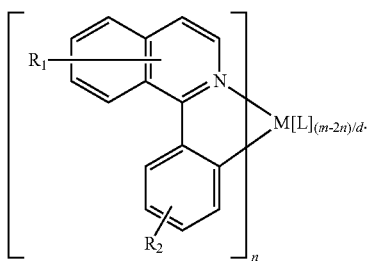

In the compound of Formula I, M is a metal having an atomic weight higher than 40, L is a second ligand, m is the maximum coordination number of the metal M, d is the denticity of L, and n is at least 1. $R_1$ is independently selected for each ligand and represents di, tri, tetra, penta substitutions, or no substitution. Each of $R_1$ is independently selected from the group consisting of hydrogen, deuterium, halide, alkyl, cycloalkyl, heteroalkyl, arylalkyl, alkoxy, aryloxy, amino, silyl, germyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

At least two of $R_1$ is independently selected from two to six carbon containing alkyl, silyl, germyl, cycloalkyl, and combinations thereof. $R_2$ may represent mono, di, tri, tetra substitutions, or no substitution, and each of $R_2$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one embodiment, the first device is a consumer product. In one embodiment, the first device is an organic light-emitting device. In one embodiment, the organic layer is an emissive layer and the compound is a non-emissive dopant. In one embodiment, the organic layer further comprises a host.

In one embodiment, the host is a metal 8-hydroxyquinolate.

In one embodiment, the host is selected from the group consisting of:

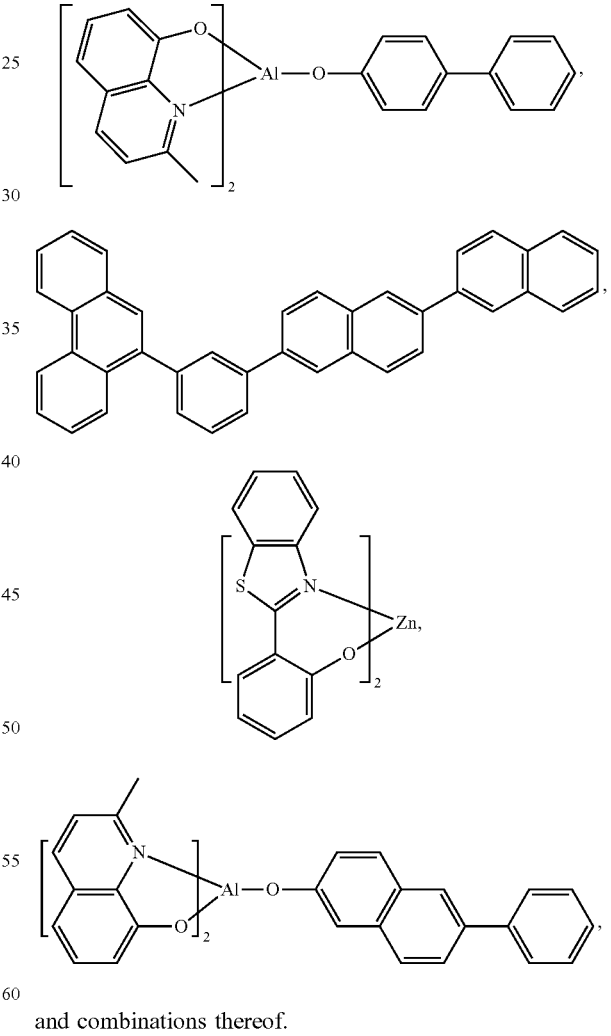

and combinations thereof.

Device Examples

All example devices were fabricated by high vacuum ($<10^{-7}$ Torr) thermal evaporation (VTE). The anode electrode is 1200 Å of indium tin oxide (ITO). The cathode consisted of 10 Å of LiF followed by 1000 Å of Al. All devices are encapsulated with a glass lid sealed with an epoxy resin in a nitrogen glove box (<1 ppm of H₂O and O₂) immediately after fabrication, and a moisture getter was incorporated inside the package.

The organic stack of the device examples consisted of sequentially, from the ITO surface, 100 Å of Compound A as the hole injection layer (HIL), 400 Å of 4,4'-bis[N-(1-naphthyl)-N-phenylamino]biphenyl (NPD) as the hole transporting layer (HTL), 300 Å of the compound of Formula I doped in with BAlq as host with from 4 to 12 wt % of an iridium-containing phosphorescent compound as the emissive layer (EML), 450 or 550 Å of Alq₃ (tris-8-hydroxyquinoline aluminum) as the electron transport layer (ETL). Comparative Examples with Compound B and C were fabricated similarly to the Device Examples except that the Compound B and C were used as the emitters in the EML.

The device results and data are summarized in Tables 1, 2, and 3 from those devices. As used herein, Compounds A, B, and C have the following structures:

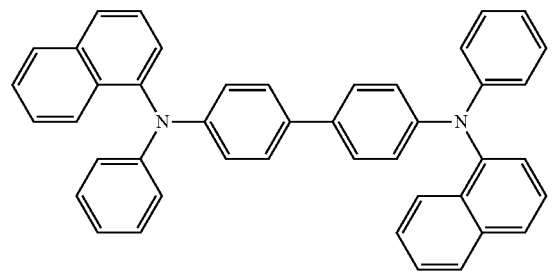

NPD

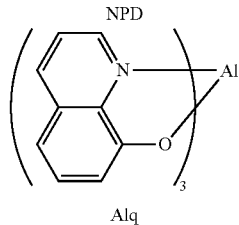

Alq

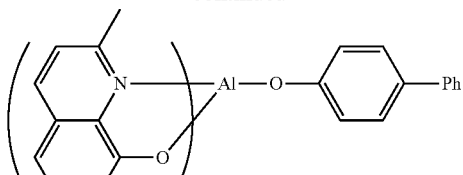

BAlq

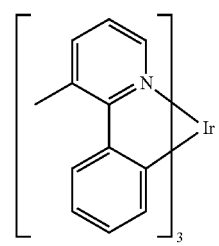

Compound A

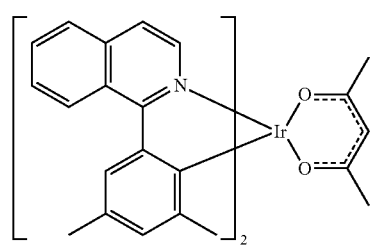

Compound B

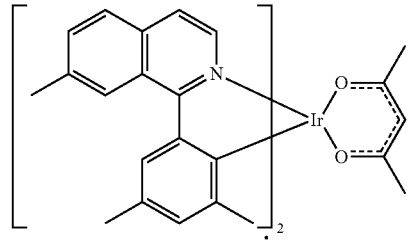

Compound C

TABLE 1

Device structures of invention compounds and comparative compounds

| Example | HIL | HTL | EML (300 Å, doping %) | | BL | ETL |
|---|---|---|---|---|---|---|
| Comparative Example 1 | Compound A 100 Å | NPD 400 Å | BAlq | Compound B 6% | None | Alq 550 Å |
| Comparative Example 2 | Compound A 100 Å | NPD 400 Å | BAlq | Compound B 9% | None | Alq 550 Å |
| Comparative Example 3 | Compound A 100 Å | NPD 400 Å | BAlq | Compound B 12% | None | Alq 550 Å |
| Comparative Example 4 | Compound A 100 Å | NPD 400 Å | BAlq | Compound C 6% | None | Alq 550 Å |
| Comparative Example 5 | Compound A 100 Å | NPD 400 Å | BAlq | Compound C 9% | None | Alq 550 Å |
| Comparative Example 6 | Compound A 100 Å | NPD 400 Å | BAlq | Compound C 12% | None | Alq 550 Å |
| Example 1 | Compound A 100 Å | NPD 400 Å | BAlq | Compound 1 4% | None | Alq 550 Å |
| Example 2 | Compound A 100 Å | NPD 400 Å | BAlq | Compound 1 6% | None | Alq 550 Å |
| Example 3 | Compound A 100 Å | NPD 400 Å | BAlq | Compound 1 8% | None | Alq 550 Å |
| Example 4 | Compound A 100 Å | NPD 400 Å | BAlq | Compound 1 6% | BAlq 100 Å | Alq 450 Å |
| Example 5 | Compound A 100 Å | NPD 400 Å | BAlq | Compound 2 5% | None | Alq 550 Å |
| Example 6 | Compound A 100 Å | NPD 400 Å | BAlq | Compound 2 7% | None | Alq 550 Å |
| Example 7 | Compound A 100 Å | NPD 400 Å | BAlq | Compound 2 10% | None | Alq 550 Å |
| Example 8 | Compound A 100 Å | NPD 400 Å | BAlq | Compound 2 7% | BAlq 100 Å | Alq 450 Å |
| Example 9 | Compound A 100 Å | NPD 400 Å | BAlq | Compound 3 5% | None | Alq 550 Å |
| Example 10 | Compound A 100 Å | NPD 400 Å | BAlq | Compound 3 7% | None | Alq 550 Å |
| Example 11 | Compound A 100 Å | NPD 400 Å | BAlq | Compound 3 10% | None | Alq 550 Å |

TABLE 1-continued

Device structures of invention compounds and comparative compounds

| Example | HIL | HTL | EML (300 Å, doping %) | | BL | ETL |
|---|---|---|---|---|---|---|
| Example 12 | Compound A 100 Å | NPD 400 Å | BAlq | Compound 3 7% | BAlq 100 Å | Alq 450 Å |
| Example 13 | Compound A 100 Å | NPD 400 Å | BAlq | Compound 22 4% | None | Alq 550 Å |
| Example 14 | Compound A 100 Å | NPD 400 Å | BAlq | Compound 22 6% | None | Alq 550 Å |
| Example 15 | Compound A 100 Å | NPD 400 Å | BAlq | Compound 22 8% | None | Alq 550 Å |
| Example 16 | Compound A 100 Å | NPD 400 Å | BAlq | Compound 22 6% | BAlq 100 Å | Alq 450 Å |

TABLE 2

VTE device results

| | x | y | $\lambda_{max}$ (nm) | FWHM (nm) | Voltage (V) | LE (Cd/A) | EQE (%) | PE (lm/W) | LT80 % (h) |
|---|---|---|---|---|---|---|---|---|---|
| Comparative Example 1 Compound B | 0.693 | 0.304 | 635 | 63 | 10 | 10.8 | 18.3 | 3.4 | 606 |
| Comparative Example 2 Compound B | 0.695 | 0.303 | 637 | 66 | 9.9 | 10.5 | 18.5 | 3.3 | 799 |
| Comparative Example 3 Compound B | 0.693 | 0.304 | 637 | 66 | 9.5 | 10.0 | 17.7 | 3.3 | 948 |
| Comparative Example 4 Compound C | 0.690 | 0.306 | 633 | 63 | 10.3 | 12.2 | 19.1 | 3.7 | 650 |
| Comparative Example 5 Compound C | 0.692 | 0.306 | 635 | 65 | 9.4 | 11.8 | 19.3 | 3.9 | 475 |
| Comparative Example 6 Compound C | 0.691 | 0.306 | 635 | 66 | 8.9 | 11.5 | 19.0 | 4.1 | 700 |
| Example 1 Compound 1 | 0.687 | 0.309 | 628 | 52 | 10.1 | 12.5 | 17.8 | 3.9 | 178 |
| Example 2 Compound 1 | 0.689 | 0.307 | 630 | 56 | 9.9 | 12.6 | 18.7 | 4.0 | 174 |
| Example 3 Compound 1 | 0.691 | 0.306 | 632 | 56 | 9.5 | 12.4 | 19.0 | 4.1 | 171 |
| Example 4 Compound 1 | 0.690 | 0.307 | 630 | 56 | 10.9 | 12.5 | 18.6 | 3.6 | 160 |
| Example 5 Compound 2 | 0.687 | 0.311 | 630 | 58 | 9.5 | 13.8 | 19.6 | 4.6 | 350 |
| Example 6 Compound 2 | 0.688 | 0.310 | 630 | 60 | 9.5 | 13.8 | 19.9 | 4.5 | 360 |
| Example 7 Compound 2 | 0.688 | 0.310 | 632 | 62 | 8.8 | 13.1 | 19.4 | 4.7 | 400 |
| Example 8 Compound 2 | 0.687 | 0.309 | 630 | 58 | 10.5 | 12.9 | 18.7 | 3.9 | 360 |
| Example 9 Compound 3 | 0.685 | 0.313 | 626 | 58 | 9.5 | 14.8 | 19.8 | 4.9 | 232 |
| Example 10 Compound 3 | 0.687 | 0.311 | 628 | 62 | 8.9 | 14.5 | 20.5 | 5.1 | 260 |
| Example 11 Compound 3 | 0.688 | 0.310 | 630 | 64 | 8.1 | 14.0 | 20.3 | 5.4 | 235 |
| Example 12 Compound 3 | 0.687 | 0.311 | 628 | 60 | 9.7 | 14.5 | 20.2 | 4.7 | 280 |
| Example 13 Compound 22 | 0.684 | 0.313 | 626 | 48 | 9.3 | 14.8 | 18.8 | 5.0 | 192 |
| Example 14 Compound 22 | 0.686 | 0.311 | 626 | 52 | 8.8 | 14.3 | 19.1 | 5.1 | 170 |
| Example 15 Compound 22 | 0.686 | 0.311 | 628 | 52 | 8.2 | 14.2 | 19.2 | 5.4 | 122 |
| Example 16 Compound 22 | 0.686 | 0.312 | 626 | 50 | 9.3 | 14.8 | 19.6 | 5.0 | 210 |

Table 2 is a summary of the device data. The luminous efficiency (LE), external quantum efficiency (EQE) and power efficiency (PE) were measured at 1000 nits, while the lifetime ($LT_{80\%}$) was defined as the time required for the device to decay to 80% of its initial luminance under a constant current density of 40 mA/cm$^2$.

From Table 2, it can be seen that the EQE, LE and PE of Compounds 1, 2, 3, and 22, which are compounds of Formula I, at three different doping concentrations (without a hole blocking layer) are all higher than those of Comparative Compounds B and C. For example, when the device has the same 6% emitter doping concentration without the hole blocking layer, Compound 22 has EQE of 19.1%, LE of 14.3 Cd/A, and PE of 5.1 lm/W, respectively. This compares to Comparative Compounds B and C which have EQE of 18.3 and 19.1%, LE of 10.8 and 12.2 Cd/A, and PE of 3.4 and 3.7 lm/W, respectively. The device results indicate that, surprisingly, the di-alkyl substituted Compounds 1, 2, 3 and 22 are more efficient than comparative compound B and mono-substituted compound C. It can also been seen from Table 2 that the FWHM (full width at half maximum) values of Compound 1, 2, 3, and 22 under different device structures are in the range of 48-64 nm, which is significantly narrower than those of Compounds B and C, which are in the range of 63-66 nm. Smaller FWHM values are often desirable in display applications. Thus, the use of compounds of Formula I, which are at least di-substituted on the heterocyclic ring contained therein can improve device performance, because these compounds have high EQE, LE, PE values and low FWHM values.

TABLE 3

Comparison of Sublimation Temperatures

| Compounds | Sublimation Temperature (° C.) | Temperature Difference Relative to Compound B |
|---|---|---|
| Compound B | 210 | |
| Compound C | 218 | −8 |
| Compound 1 | 197 | 13 |
| Compound 2 | 202 | 8 |

TABLE 3-continued

Comparison of Sublimation Temperatures

| Compounds | Sublimation Temperature (° C.) | Temperature Difference Relative to Compound B |
|---|---|---|
| Compound 3 | 204 | 6 |
| Compound 22 | 194 | 16 |

It can be seen that di-substitution on the heteroaromatic ring in compounds of Formula I can decreases the sublimation temperature of complex as shown in Table 3. It was surprisingly discovered that di-substituted compounds of Formula I had lower sublimation temperatures than un-substituted or mono-substituted compounds. For example, Compound 22 had a significantly lower sublimation temperature than Comparative Compound B (194° C. vs 210° C.) despite the fact that Compound 22 has a higher molecular weight than Comparative Compound B.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

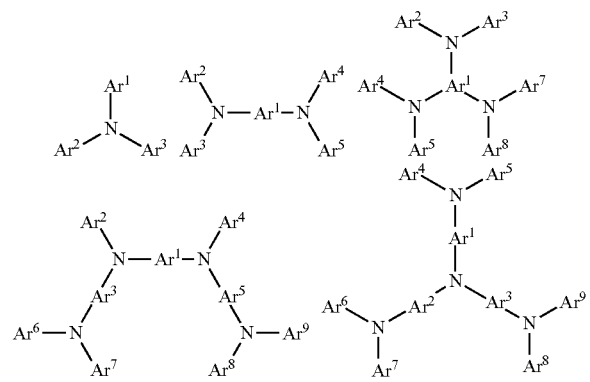

Each of Ar¹ to Ar⁹ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, Ar¹ to Ar⁹ is independently selected from the group consisting of:

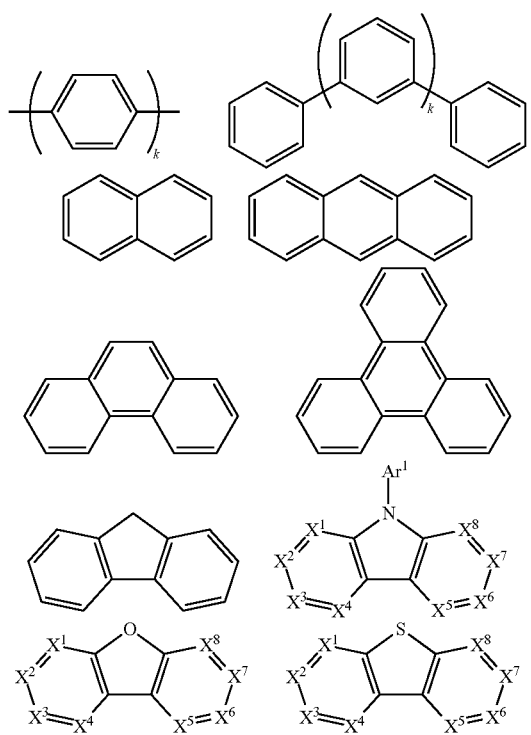

k is an integer from 1 to 20; $X^1$ to $X^8$ is C (including CH) or N; $Ar^1$ has the same group defined above.

Examples of metal complexes used in HIL or HTL include, but not limit to the following general formula:

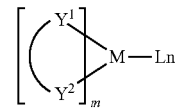

M is a metal, having an atomic weight greater than 40; ($Y^1$-$Y^2$) is a bidentate ligand, $Y^1$ and $Y^2$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, ($Y^1$-$Y^2$) is a 2-phenylpyridine derivative.
In another aspect, ($Y^1$-$Y^2$) is a carbene ligand.
In another aspect, M is selected from Ir, Pt, Os, and Zn.
In a further aspect, the metal complex has a smallest oxidation potential in solution vs. $Fc^+$/Fc couple less than about 0.6 V.

Host:
The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

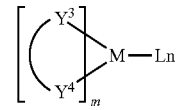

M is a metal; ($Y^3$-$Y^4$) is a bidentate ligand, $Y^3$ and $Y^4$ are independently selected from C, N, O, P, and S; L is an ancillary ligand; m is an integer value from 1 to the maximum number of ligands that may be attached to the metal; and m+n is the maximum number of ligands that may be attached to the metal.

In one aspect, the metal complexes are:

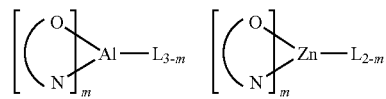

(O—N) is a bidentate ligand, having metal coordinated to atoms O and N.
In another aspect, M is selected from Ir and Pt.
In a further aspect, ($Y^3$-$Y^4$) is a carbene ligand.
Examples of organic compounds used as host are selected from the group consisting aromatic hydrocarbon cyclic compounds such as benzene, biphenyl, triphenyl, triphenylene, naphthalene, anthracene; phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atome, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

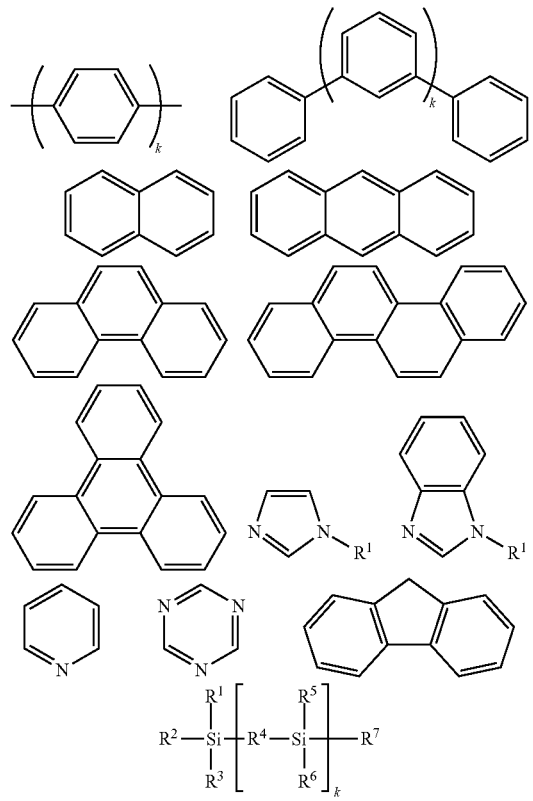

-continued

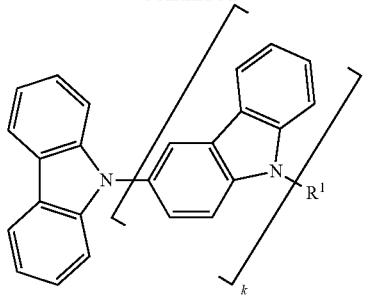

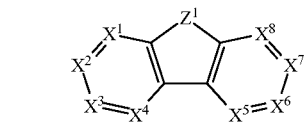

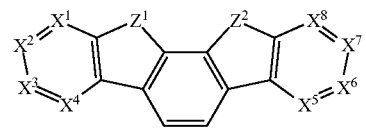

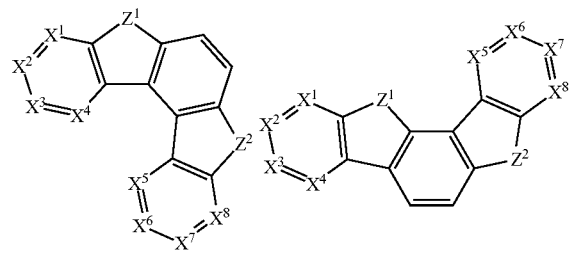

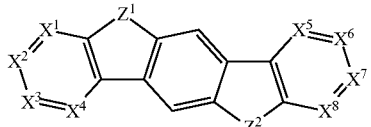

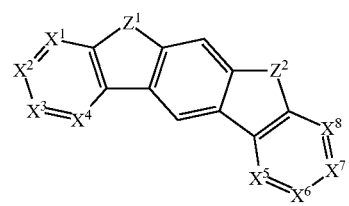

$R^1$ to $R^7$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

k is an integer from 0 to 20.

$X^1$ to $X^8$ is selected from C (including CH) or N.

$Z^1$ and $Z^2$ is selected from $NR^1$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

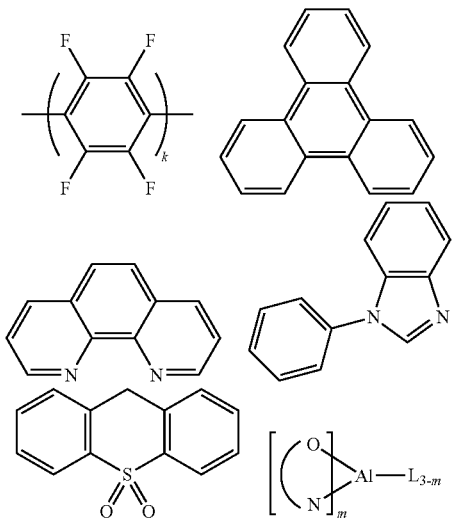

k is an integer from 0 to 20; L is an ancillary ligand, m is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

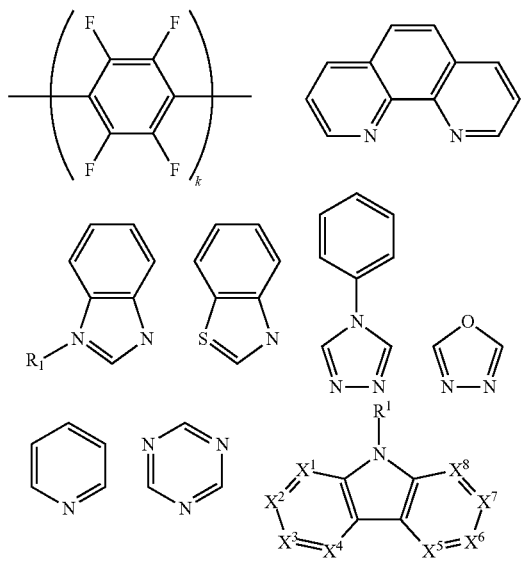

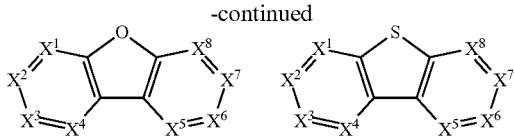

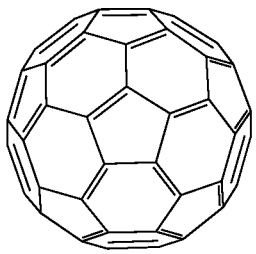

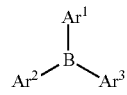

$R^1$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above.

$Ar^1$ to $Ar^3$ has the similar definition as Ar's mentioned above.

k is an integer from 0 to 20.

$X^1$ to $X^8$ is selected from C (including CH) or N.

In another aspect, the metal complexes used in ETL contains, but not limit to the following general formula:

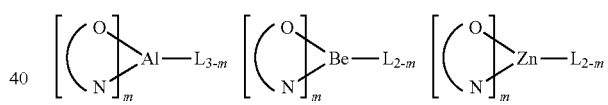

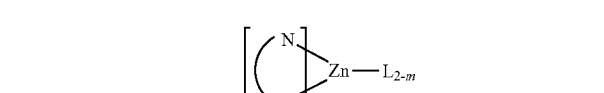

(O—N) or (N—N) is a bidentate ligand, having metal coordinated to atoms O, N or N,N; L is an ancillary ligand; m is an integer value from 1 to the maximum number of ligands that may be attached to the metal.

In any above-mentioned compounds used in each layer of the OLED device, the hydrogen atoms can be partially or fully deuterated.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 4 below. Table 4 lists non-limiting classes of materials, non-limiting examples of compounds for each class, and references that disclose the materials.

TABLE 4

| MATERIAL | EXAMPLES OF MATERIAL | PUBLICATIONS |
|---|---|---|
| Hole injection materials | | |
| Phthalocyanine and porphryin compounds | 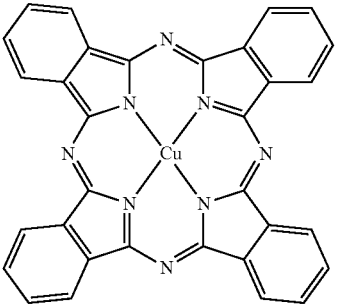 | Appl. Phys. Lett. 69, 2160 (1996) |
| Starburst triarylamines | 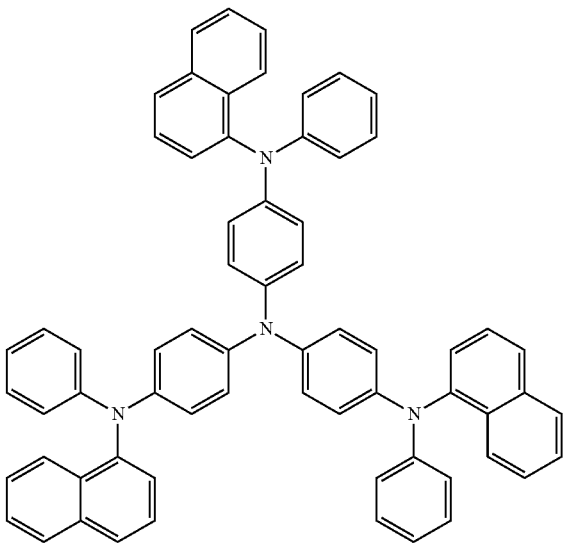 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | 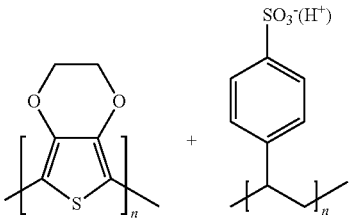 | Synth. Met. 87, 171 (1997)<br>WO2007002683 |
| Phosphonic acid and sliane SAMs | 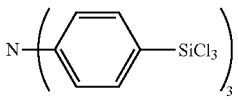 | US20030162053 |
| Triarylamine or polythiophene polymers with conductivity dopants | 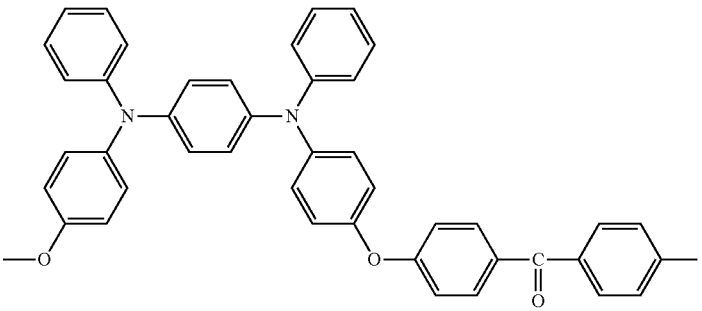 | EP1725079A1 |

TABLE 4-continued
| MATERIAL | EXAMPLES OF MATERIAL | PUBLICATIONS |
|---|---|---|
| | and 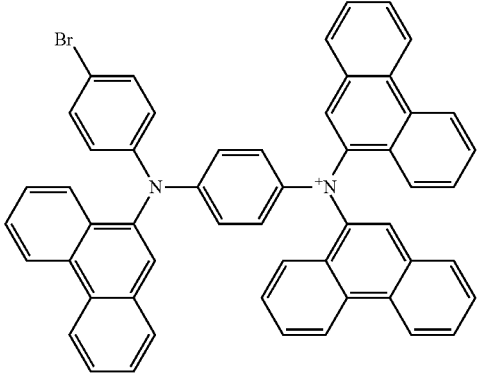 [SMILES: Brc1ccc(N(c2ccc([NH+](c3cc4ccccc4c4ccccc34)c3cc4ccccc4c4ccccc34)cc2)c2cc3ccccc3c3ccccc23)cc1] | |
| | 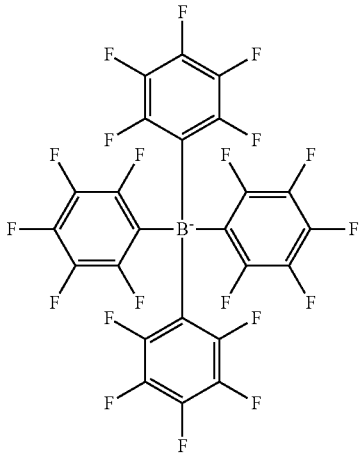 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Organic compounds with conductive inorganic compounds, such as molybdenum and tungsten oxides | 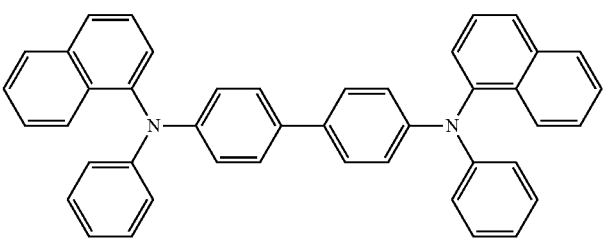 + $MoO_x$ | US20050123751 SID Symposium Digest, 37, 923 (2006) WO2009018009 |
| n-type semiconducting organic complexes | 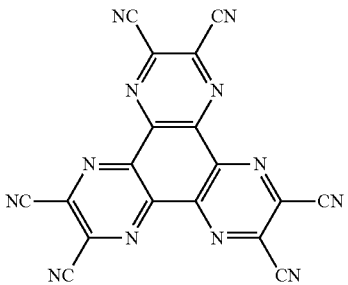 [SMILES: N#Cc1nc2c3nc(C#N)c(C#N)nc3c3nc(C#N)c(C#N)nc3c2nc1C#N] | US20020158242 |

TABLE 4-continued

| MATERIAL | EXAMPLES OF MATERIAL | PUBLICATIONS |
| --- | --- | --- |
| Metal organometallic complexes | | US20060240279 |
| Cross-linkable compounds | | US20080220265 |
| Polythiophene based polymers and copolymers | | WO 2011075644<br>EP2350216 |
| Hole transporting materials | | |
| Triarylamines<br>(e.g., TPD, α-NPD) | | Appl. Phys. Lett. 51, 913 (1987) |

TABLE 4-continued
| MATERIAL | EXAMPLES OF MATERIAL | PUBLICATIONS |
|---|---|---|
| | 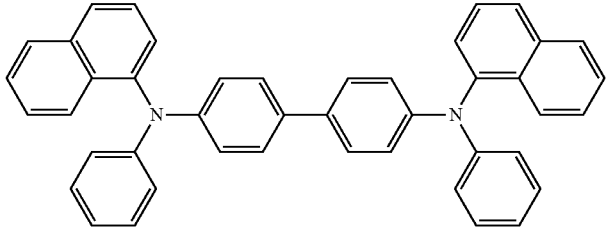 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |
| | 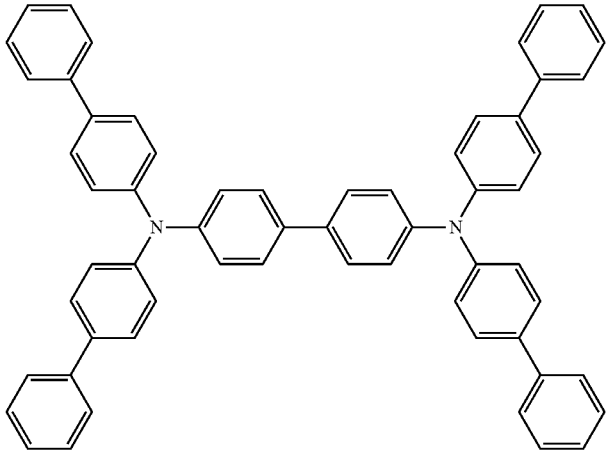 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 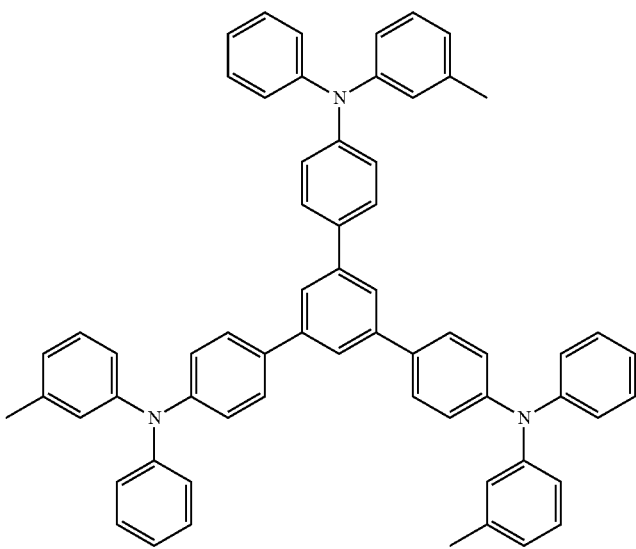 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |

TABLE 4-continued
| MATERIAL | EXAMPLES OF MATERIAL | PUBLICATIONS |
|---|---|---|
|  | 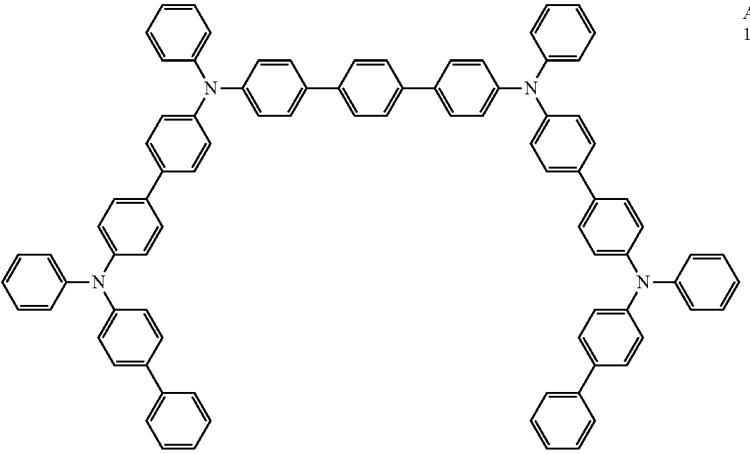 | Appl. Phys. Lett. 90, 183503 (2007) |
|  | 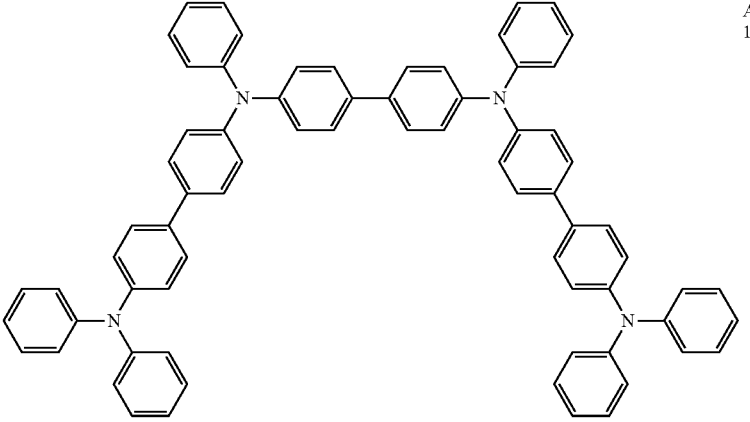 | Appl. Phys. Lett. 90, 183503 (2007) |
| Triaylamine on spirofluorene core | 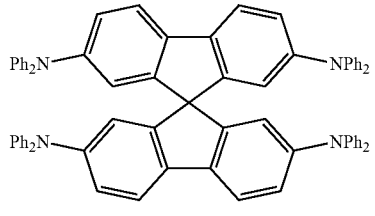 | Synth. Met. 91, 209 (1997) |
| Arylamine carbazole compounds | 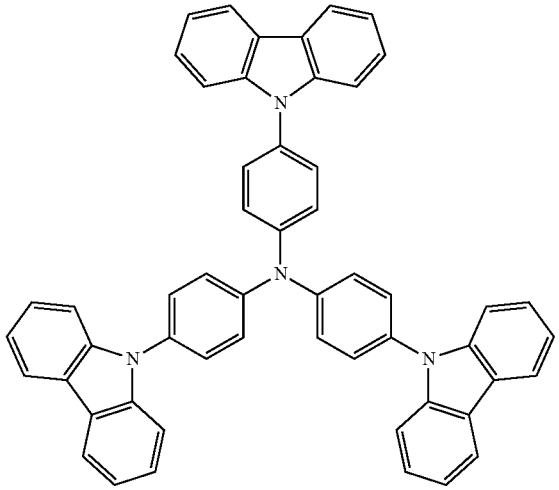 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |

TABLE 4-continued
| MATERIAL | EXAMPLES OF MATERIAL | PUBLICATIONS |
|---|---|---|
| Triarylamine with (di)benzothiophene/ (di)benzofuran | 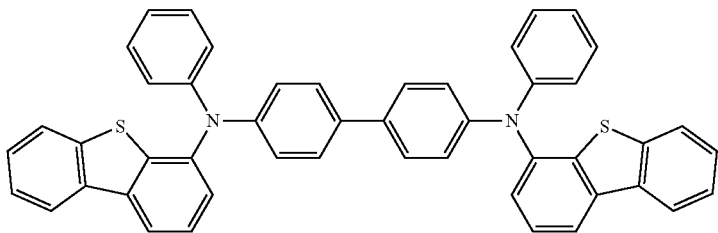 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 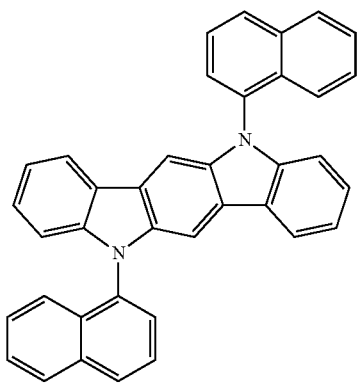 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 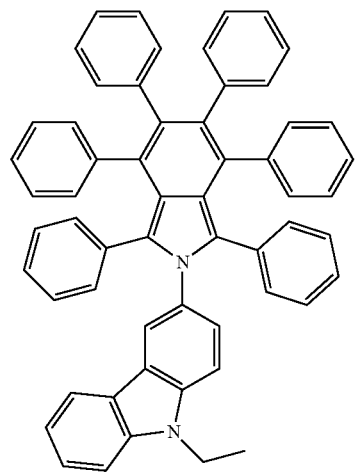 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 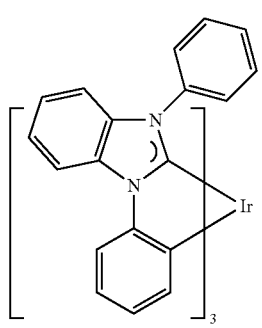 | US20080018221 |

TABLE 4-continued

| MATERIAL | EXAMPLES OF MATERIAL | PUBLICATIONS |
|---|---|---|
| Phosphorescent OLED host materials | | |
| Red hosts | | |
| Arylcarbazoles | | Appl. Phys. Lett. 78, 1622 (2001) |
| Metal 8-hydroxyquinolates (e.g., Alq$_3$, BAlq) | | Nature 395, 151 (1998) |
| | | US20060202194 |
| | | WO2005014551 |
| | | WO2006072002 |
| Metal phenoxybenzothiazole compounds | | Appl. Phys. Lett. 90, 123509 (2007) |
| Conjugated oligomers and polymers (e.g., polyfluorene) | | Org. Electron. 1, 15 (2000) |

TABLE 4-continued

| MATERIAL | EXAMPLES OF MATERIAL | PUBLICATIONS |
| --- | --- | --- |
| Aromatic fused rings | | WO2009066779, WO2009066778, WO2009063833, US20090045731, US20090045730, WO2009008311, US20090008605, US20090009065 |
| Zinc complexes | | WO2010056066 |
| Chrysene based compounds | | WO2011086863 |

Green hosts

| | | |
| --- | --- | --- |
| Arylcarbazoles | | Appl. Phys. Lett. 78, 1622 (2001) |
| | | US20030175553 |
| | | WO2001039234 |

TABLE 4-continued
| MATERIAL | EXAMPLES OF MATERIAL | PUBLICATIONS |
|---|---|---|
| Aryltriphenylene compounds | 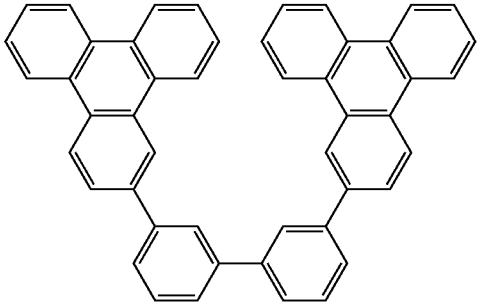 [SMILES: c1cc(-c2cccc(-c3ccc4c5ccccc5c5ccccc5c4c3)c2)cc(-c2ccc3c4ccccc4c4ccccc4c3c2)c1] | US20060280965 |
| | 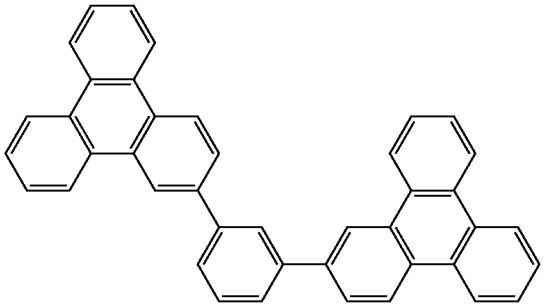 [SMILES: c1cc(-c2ccc3c4ccccc4c4ccccc4c3c2)cc(-c2ccc3c4ccccc4c4ccccc4c3c2)c1] | US20060280965 |
| | 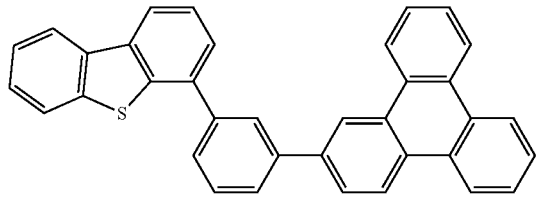 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 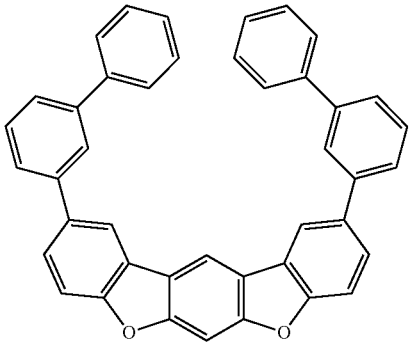 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 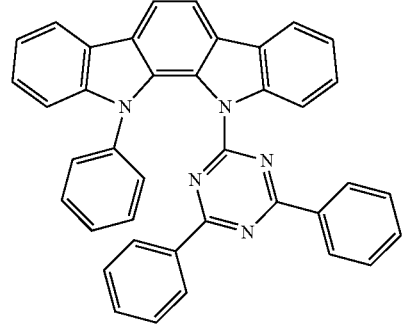 [SMILES: c1ccc(-c2nc(-c3ccccc3)nc(-n3c4ccccc4c4ccc5c6ccccc6n(-c6ccccc6)c5c43)n2)cc1] | WO2008056746 |

| MATERIAL | EXAMPLES OF MATERIAL | PUBLICATIONS |
|---|---|---|
| | 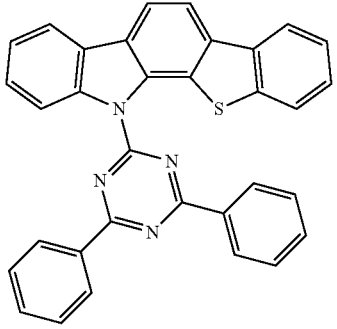 [SMILES: c1ccc(-c2nc(-c3ccccc3)nc(-n3c4ccccc4c4ccc5c6ccccc6sc5c43)n2)cc1] | WO2010107244 |
| Aza-carbazole/DBT/DBF | 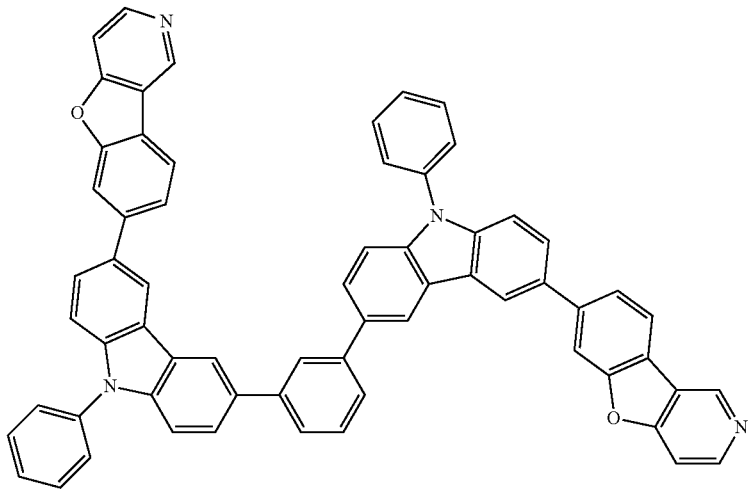 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 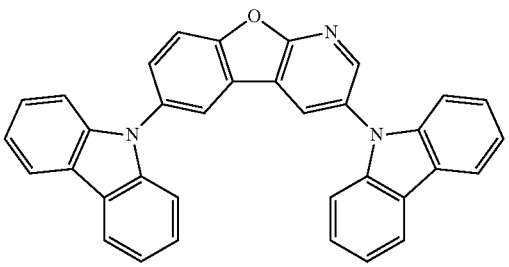 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 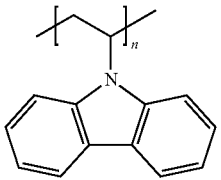 | Appl. Phys. Lett. 77, 2280 (2000) |
| Spirofluorene compounds | 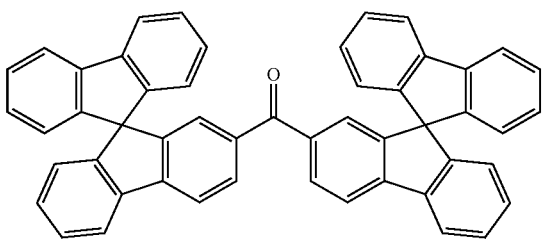 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE 4-continued
| MATERIAL | EXAMPLES OF MATERIAL | PUBLICATIONS |
|---|---|---|
| Metal phenoxybenzooxazole compounds | 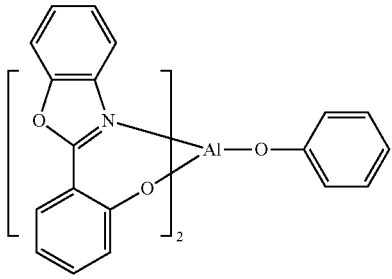 | WO2005089025 |
| | 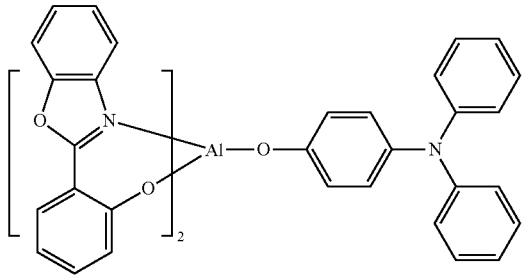 | WO2006132173 |
| | 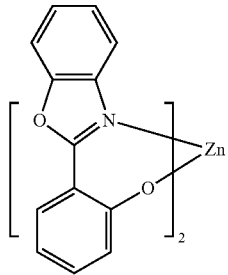 | JP200511610 |
| Spirofluorene-carbazole compounds | 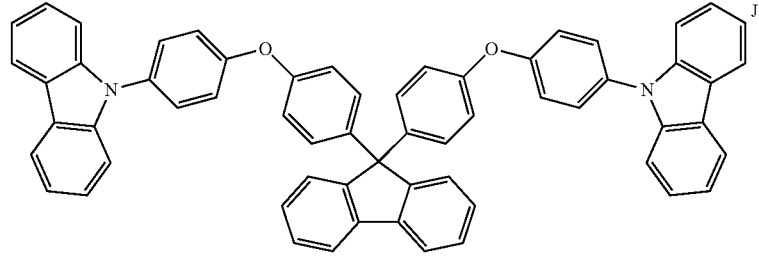 | JP2007254297 |
| | 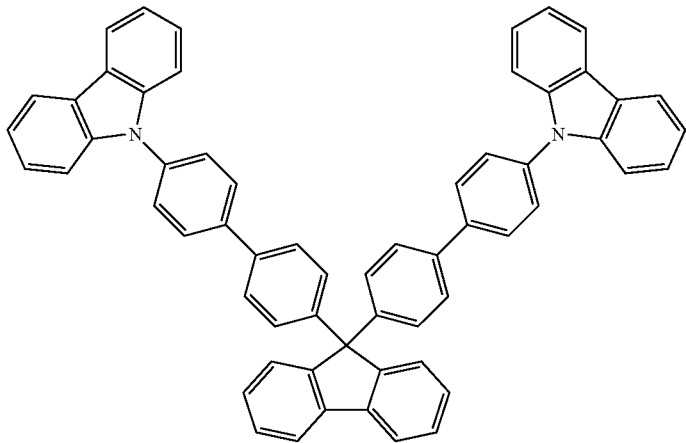 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |

TABLE 4-continued

| MATERIAL | EXAMPLES OF MATERIAL | PUBLICATIONS |
|---|---|---|
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE 4-continued

| MATERIAL | EXAMPLES OF MATERIAL | PUBLICATIONS |
| --- | --- | --- |
| Metal phenoxypyridine compounds | | WO2005030900 |
| Metal coordination complexes (e.g., Zn, Al with N^N ligands) | | US20040137268, US20040137267 |

Blue hosts

| MATERIAL | EXAMPLES OF MATERIAL | PUBLICATIONS |
| --- | --- | --- |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |

TABLE 4-continued
| MATERIAL | EXAMPLES OF MATERIAL | PUBLICATIONS |
|---|---|---|
| | 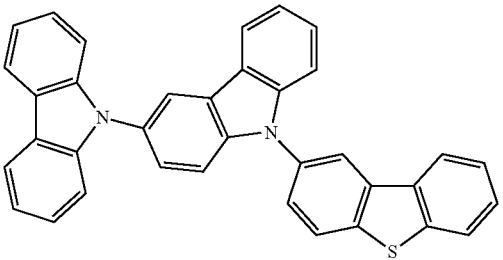 [SMILES: c1ccc2c(c1)sc1ccc(-n3c4ccccc4c4cc(-n5c6ccccc6c6ccccc65)ccc43)cc12] | WO2009086028 |
| | 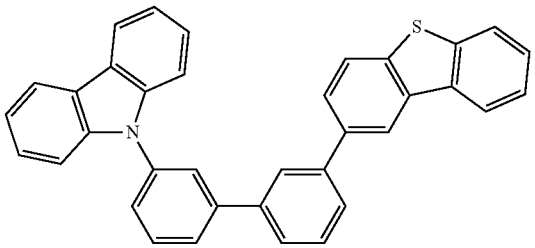 [SMILES: c1cc(-c2cccc(-n3c4ccccc4c4ccccc43)c2)cc(-c2ccc3sc4ccccc4c3c2)c1] | US20090030202, US20090017330 |
| | 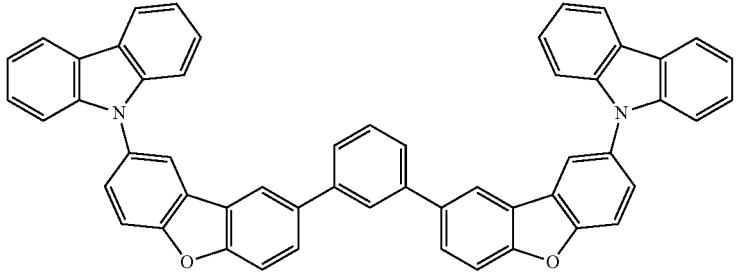 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 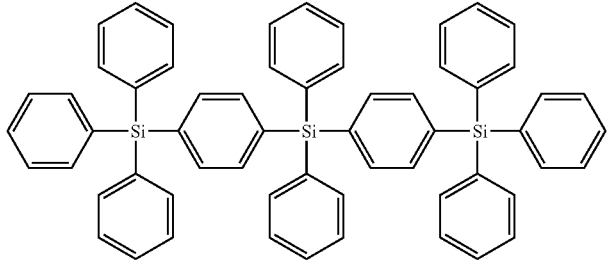 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 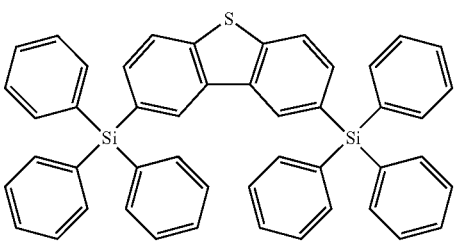 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |

TABLE 4-continued

| MATERIAL | EXAMPLES OF MATERIAL | PUBLICATIONS |
|---|---|---|
| Silicon/Germanium aryl compounds | | EP2034538A |
| Aryl benzoyl ester | | WO2006100298 |
| Carbazole linked by non-conjugated groups | | US20040115476 |
| Aza-carbazoles | | US20060121308 |
| High triplet metal organometallic complex | | U.S. Pat. No. 7,154,114 |

Phosphorescent dopants
Red dopants

| | | |
|---|---|---|
| Heavy metal porphyrins (e.g., PtOEP) | | Nature 395, 151 (1998) |

TABLE 4-continued

| MATERIAL | EXAMPLES OF MATERIAL | PUBLICATIONS |
| --- | --- | --- |
| Iridium(III) organometallic complexes | | Appl. Phys. Lett. 78, 1622 (2001) |
| | | US2006835469 |
| | | US2006835469 |
| | | US20060202194 |
| | | US20060202194 |

TABLE 4-continued

| MATERIAL | EXAMPLES OF MATERIAL | PUBLICATIONS |
|---|---|---|
| | | US20070087321 |
| | | US20080261076<br>US20100090591 |
| | | US20070087321 |
| | | Adv. Mater. 19, 739 (2007) |
| | | WO2009100991 |

TABLE 4-continued
| MATERIAL | EXAMPLES OF MATERIAL | PUBLICATIONS |
|---|---|---|
| | 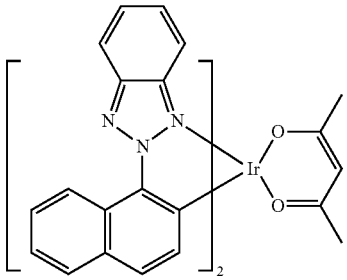 | WO2008101842 |
| | 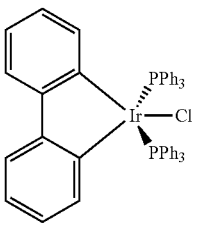 | U.S. Pat. No. 7,232,618 |
| Platinum(II) organometallic complexes | 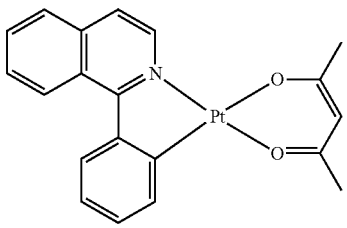 | WO2003040257 |
| | 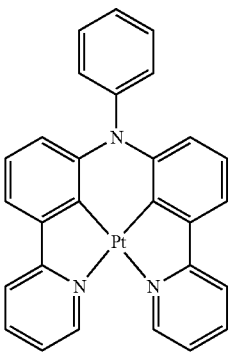 | US20070103060 |
| Osminum(III) complexes | 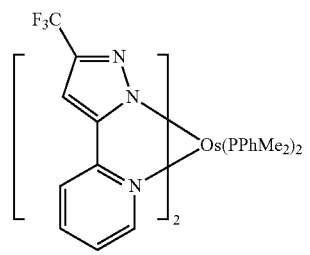 | Chem. Mater. 17, 3532 (2005) |

TABLE 4-continued

| MATERIAL | EXAMPLES OF MATERIAL | PUBLICATIONS |
| --- | --- | --- |
| Ruthenium(II) complexes | | Adv. Mater. 17, 1059 (2005) |
| Rhenium (I), (II), and (III) complexes | | US20050244673 |

Green dopants

| MATERIAL | EXAMPLES OF MATERIAL | PUBLICATIONS |
| --- | --- | --- |
| Iridium(III) organometallic complexes | and its derivatives | Inorg. Chem. 40, 1704 (2001) |
| | | US20020034656 |

TABLE 4-continued

| MATERIAL | EXAMPLES OF MATERIAL | PUBLICATIONS |
|---|---|---|
| | | U.S. Pat. No. 7,332,232 |
| | | US20090108737 |
| | | WO2010028151 |
| | | EP1841834B |

TABLE 4-continued

| MATERIAL | EXAMPLES OF MATERIAL | PUBLICATIONS |
|---|---|---|
|  |  | US20060127696 |
|  |  | US20090039776 |
|  |  | U.S. Pat. No. 6,921,915 |
|  |  | US20100244004 |
|  |  | U.S. Pat. No. 6,687,266 |

TABLE 4-continued

| MATERIAL | EXAMPLES OF MATERIAL | PUBLICATIONS |
|---|---|---|
| | | Chem. Mater. 16, 2480 (2004) |
| | | US20070190359 |
| | | US20060008670 JP2007123392 |
| | | WO2010086089, WO2011044988 |
| | | Adv. Mater. 16, 2003 (2004) |

TABLE 4-continued
| MATERIAL | EXAMPLES OF MATERIAL | PUBLICATIONS |
|---|---|---|
| | 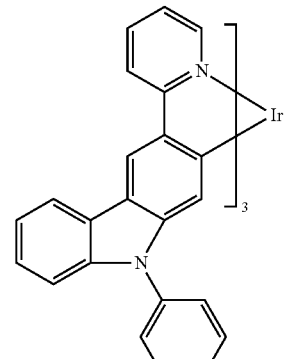 | Angew. Chem. Int. Ed. 2006, 45, 7800 |
| | 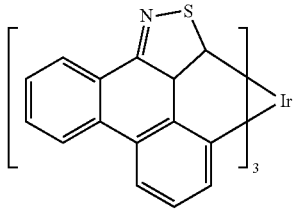 | WO2009050290 |
| | 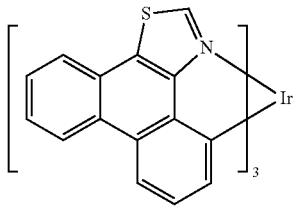 | US20090165846 |
| | 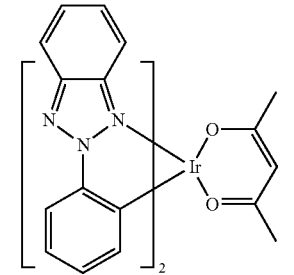 | US20080015355 |
| | 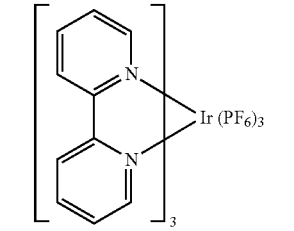 | US20010015432 |
| | 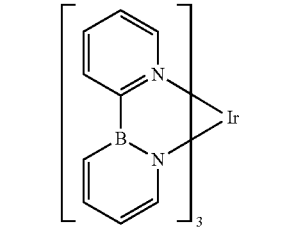 | US20100295032 |

TABLE 4-continued

| MATERIAL | EXAMPLES OF MATERIAL | PUBLICATIONS |
| --- | --- | --- |
| Monomer for polymeric metal organometallic compounds | | U.S. Pat. No. 7,250,226, U.S. Pat. No. 7,396,598 |
| Pt(II) organometallic complexes, including polydentated ligands | | Appl. Phys. Lett. 86, 153505 (2005) |
| | | Appl. Phys. Lett. 86, 153505 (2005) |
| | | Chem. Lett. 34, 592 (2005) |
| | | WO2002015645 |

TABLE 4-continued

| MATERIAL | EXAMPLES OF MATERIAL | PUBLICATIONS |
|---|---|---|
| | | US20060263635 |
| | | US20060182992<br>US20070103060 |
| Cu complexes | | WO2009000673 |
| | | US20070111026 |

TABLE 4-continued

| MATERIAL | EXAMPLES OF MATERIAL | PUBLICATIONS |
| --- | --- | --- |
| Gold complexes | | Chem. Commun. 2906 (2005) |
| Rhenium(III) complexes | | Inorg. Chem. 42, 1248 (2003) |
| Osmium(II) complexes | | U.S. Pat. No. 7,279,704 |
| Deuterated organometallic complexes | | US20030138657 |

TABLE 4-continued

| MATERIAL | EXAMPLES OF MATERIAL | PUBLICATIONS |
|---|---|---|
| Organometallic complexes with two or more metal centers | | US20030152802 |
| | | U.S. Pat. No. 7,090,928 |
| Blue dopants | | |
| Iridium(III) organometallic complexes | | WO2002002714 |
| | | WO2006009024 |
| | | US20060251923<br>US20110057559<br>US20110204333 |

TABLE 4-continued

| MATERIAL | EXAMPLES OF MATERIAL | PUBLICATIONS |
| --- | --- | --- |
| | | U.S. Pat. No. 7,393,599, WO2006056418, US20050260441, WO2005019373 |
| | | U.S. Pat. No. 7,534,505 |
| | | WO2011051404 |
| | | U.S. Pat. No. 7,445,855 |
| | | US20070190359, US20080297033 US20100148663 |

TABLE 4-continued

| MATERIAL | EXAMPLES OF MATERIAL | PUBLICATIONS |
| --- | --- | --- |
| | | U.S. Pat. No. 7,338,722 |
| | | US20020134984 |
| | | Angew. Chem. Int. Ed. 47, 1 (2008) |
| | | Chem. Mater. 18, 5119 (2006) |
| | | Inorg. Chem. 46, 4308 (2007) |
| | | WO2005123873 |

TABLE 4-continued

| MATERIAL | EXAMPLES OF MATERIAL | PUBLICATIONS |
|---|---|---|
| | | WO2005123873 |
| | | WO2007004380 |
| | | WO2006082742 |
| Osmium(II) complexes | | U.S. Pat. No. 7,279,704 |
| | | Organometallics 23, 3745 (2004) |
| Gold complexes | | Appl. Phys. Lett. 74, 1361 (1999) |

TABLE 4-continued

| MATERIAL | EXAMPLES OF MATERIAL | PUBLICATIONS |
| --- | --- | --- |
| Platinum(II) complexes | | WO2006098120, WO2006103874 |
| Pt tetradentate complexes with at least one metal-carbene bond | | U.S. Pat. No. 7,655,323 |
| Exciton/hole blocking layer materials | | |
| Bathocuprine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |

TABLE 4-continued
| MATERIAL | EXAMPLES OF MATERIAL | PUBLICATIONS |
|---|---|---|
| 5-member ring electron deficient heterocycles such as triazole, oxadiazole, imidazole, benzoimidazole | 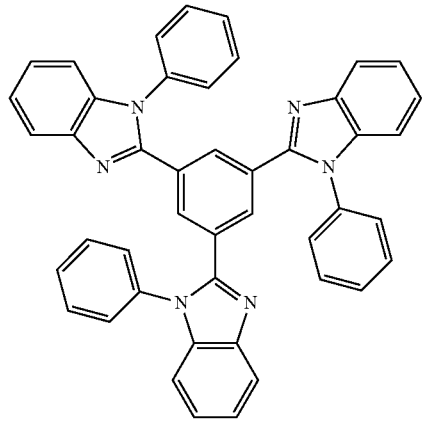 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |
| Triphenylene compounds | 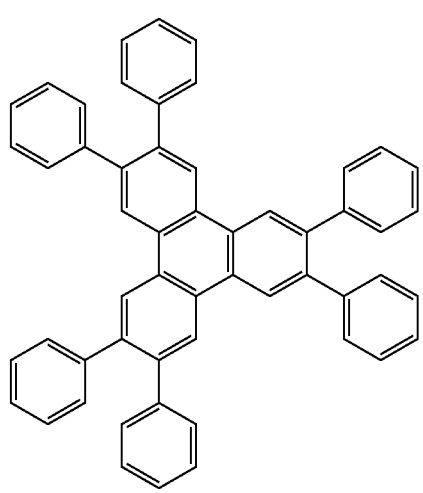 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 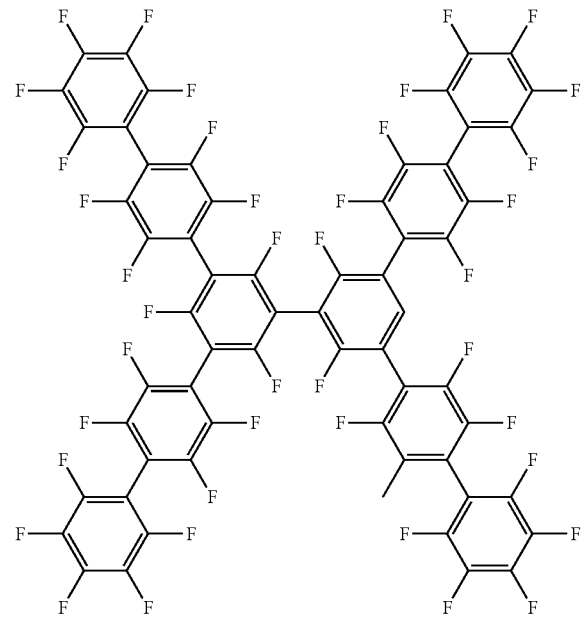 [SMILES: Cc1c(F)c(-c2cc(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |

TABLE 4-continued

| MATERIAL | EXAMPLES OF MATERIAL | PUBLICATIONS |
|---|---|---|
| Phenothiazine-S-oxide | | WO2008132085 |
| Silylated five-membered nitrogen, oxygen, sulfur or phosphorus dibenzoheterocycles | | WO2010079051 |
| Aza-carbazoles | | US20060121308 |
| Electron transporting materials | | |
| Anthracene-benzoimidazole compounds | | WO2003060956 |
| | | US20090179554 |

TABLE 4-continued

| MATERIAL | EXAMPLES OF MATERIAL | PUBLICATIONS |
| --- | --- | --- |
| Aza triphenylene derivatives | | US20090115316 |
| Anthracene-benzothiazole compounds | | Appl. Phys. Lett. 89, 063504 (2006) |
| Metal 8-hydroxyquinolates (e.g., $Alq_3$, $Zrq_4$) | | Appl. Phys. Lett. 51, 913 (1987)<br>U.S. Pat. No. 7,230,107 |
| Metal hydroxybenoquinolates | | Chem. Lett. 5, 905 (1993) |
| Bathocuprine compounds such as BCP, BPhen, etc | | Appl. Phys. Lett. 91, 263503 (2007)<br><br>Appl. Phys. Lett. 79, 449 (2001) |

TABLE 4-continued
| MATERIAL | EXAMPLES OF MATERIAL | PUBLICATIONS |
|---|---|---|
| 5-member ring electron deficient heterocycles (e.g., triazole, oxadiazole, imidazole, benzoimidazole) | 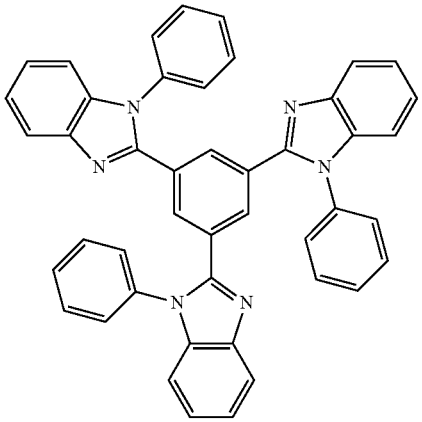 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 74, 865 (1999) |
| |  | Appl. Phys. Lett. 55, 1489 (1989) |
| | 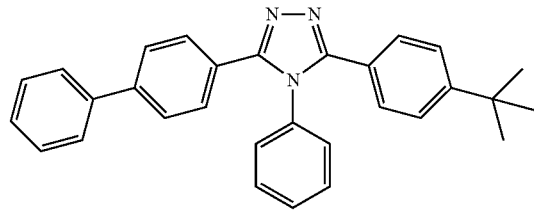 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 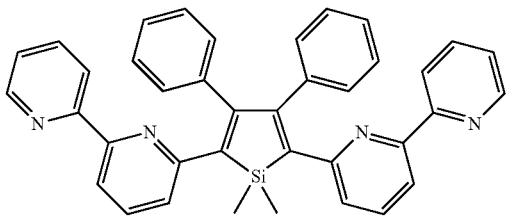 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 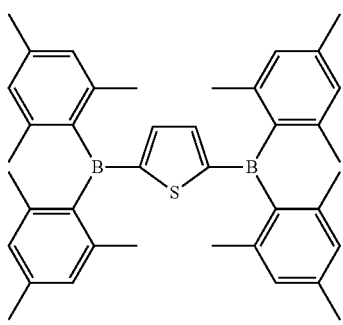 [SMILES: Cc1cc(C)c(B(c2ccc(B(c3c(C)cc(C)cc3C)c3c(C)cc(C)cc3C)s2)c2c(C)cc(C)cc2C)c(C)c1] | J. Am. Chem. Soc. 120, 9714 (1998) |
| Fluorinated aromatic compounds | 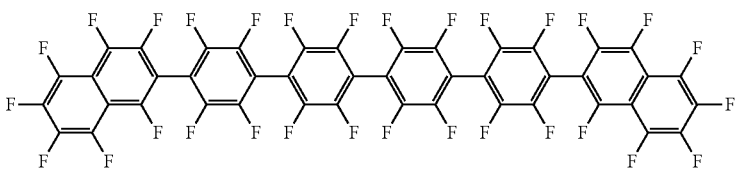 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |

TABLE 4-continued

| MATERIAL | EXAMPLES OF MATERIAL | PUBLICATIONS |
| --- | --- | --- |
| Fullerene (e.g., C60) | 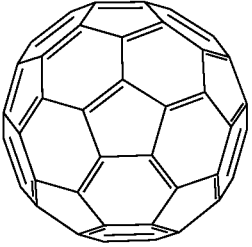 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 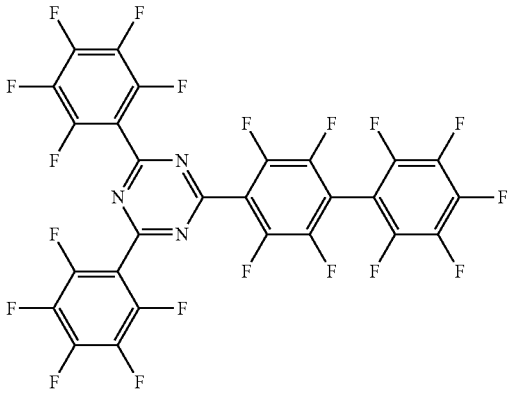 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |
| Zn (N^N) complexes | 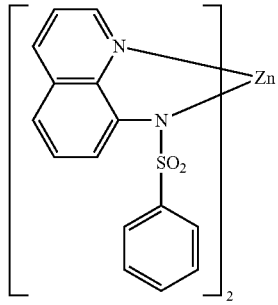 | U.S. Pat. No. 6,528,187 |

EXPERIMENTAL

Chemical abbreviations used throughout this document are as follows: Cy is cyclohexyl, dba is dibenzylideneacetone, EtOAc is ethyl acetate, DME is dimethoxyethane, dppe is 1,2-bis(diphenylphosphino)ethane, THF is tetrahydrofuran, DCM is dichloromethane, DMF is dimethylformamide, S-Phos is dicyclohexyl(2',6'-dimethoxy-[1,1'-biphenyl]-2-yl)phosphine.

Synthesis of Compound 1

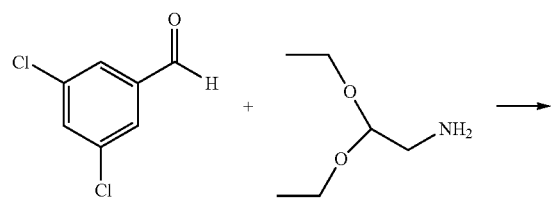

-continued

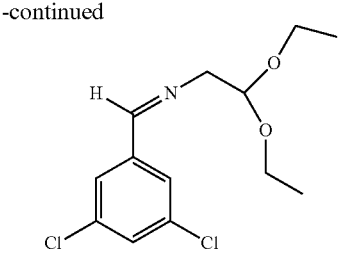

Synthesis of N-(3,5-dichlorobenzylidene)-2,2-diethoxyethanamine 3,5-dichlorobenzaldehyde (51.2 g, 284 mmol), 2,2-diethoxyethanamine (38.6 g, 284 mmol) and 270 mL toluene were charged in a 500 mL three-necked flask. The mixture was heated to reflux for 24 hours under $N_2$ with Dean-Stark apparatus to collect water by-product. 86 g (100%) light yellow liquid was obtained after evaporated solvent. The product was confirmed by GC-MS and NMR and taken on to the next step without further purification.

Synthesis of 5,7-dichloroisoquinoline

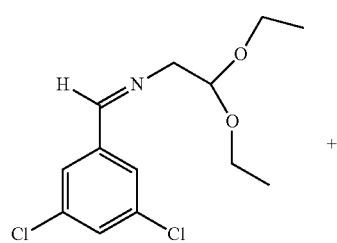

+

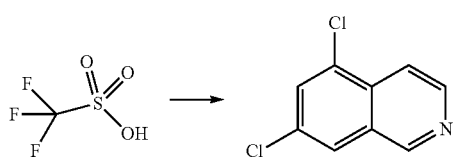

Trifluoromethanesulfonic acid (15.83 g, 103 mmol) was charged in a three-necked 100 mL flask which was equipped with a Dean-Stark apparatus and addition funnel. The trifluoromethanesulfonic acid was first heated to 120° C. and to the acid, N-(3,5-dichlorobenzylidene)-2,2-diethoxyethanamine (4 g, 13.78 mmol) dissolved in 4 mL DCM was added dropwise. After addition, the mixture was heated for another 2 hours at 120° C., then cooled to room temperature, and 8 mL of MeOH was added to quench the reaction. The reaction mixture was poured into aqueous ammonium hydroxide (120 mmol) solution, made basic with additional aqueous ammonium hydroxide, and stirred and filtered. A white solid (2.1 g, 77%) was obtained after distillation. The identity of the product was confirmed by GC and HPLC. A larger scale reaction with 32.2 g of N-(3,5-dichlorobenzylidene)-2,2-diethoxyethanamine was conducted in a same way and 16.5 g (75%) of the product was obtained for next step.

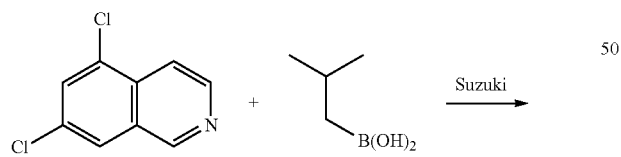

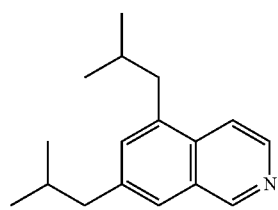

Synthesis of 5,7-diisobutylisoquinoline 5,7-Dichloroisoquinoline (5.8 g, 29.3 mmol), isobutylboronic acid (8.96 g, 88 mmol), dicyclohexyl(2',6'-dimethoxy-[1,1'-biphenyl]-2-yl)phosphine (0.962 g, 2.34 mmol), Pd$_2$(dba)$_3$ (0.536 g, 0.586 mmol), K$_3$PO$_4$ (21.8 g, 103 mmol), 150 mL toluene and 15 mL water were charged in a flask. The reaction mixture was purged by bubbling N$_2$ for 30 minutes then heated to reflux overnight. GC-MS analysis showed that the reaction was complete. Silica gel chromatography with 15% ethyl acetate in hexane (v/v) as elutent resulted in 6.7 g (95%) of the product.

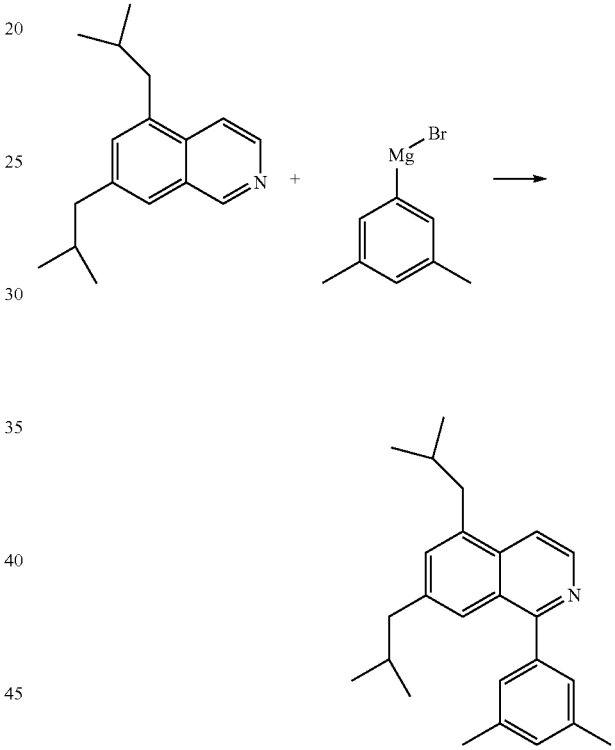

Synthesis of 1-(3,5-dimethylphenyl)-5,7-diisobutylisoquinoline 5,7-Diisobutylisoquinoline (7.4 g, 30.7 mmol) in 50 mL dry THF and was added to (3,5-dimethylphenyl)magnesium bromide (100 mL, 50.0 mmol) dropwise at room temperature and allowed to stir for 16 hours, after which the reaction mixture was heated to reflux for 5 hours. GC and HPLC analysis indicated the reaction was complete, but contained a small amount of reduced byproducts which were converted to the desired product by treatment with DDQ in THF for few minutes. After aqueous workup, 6.5 g (61.4%) of product was obtained.

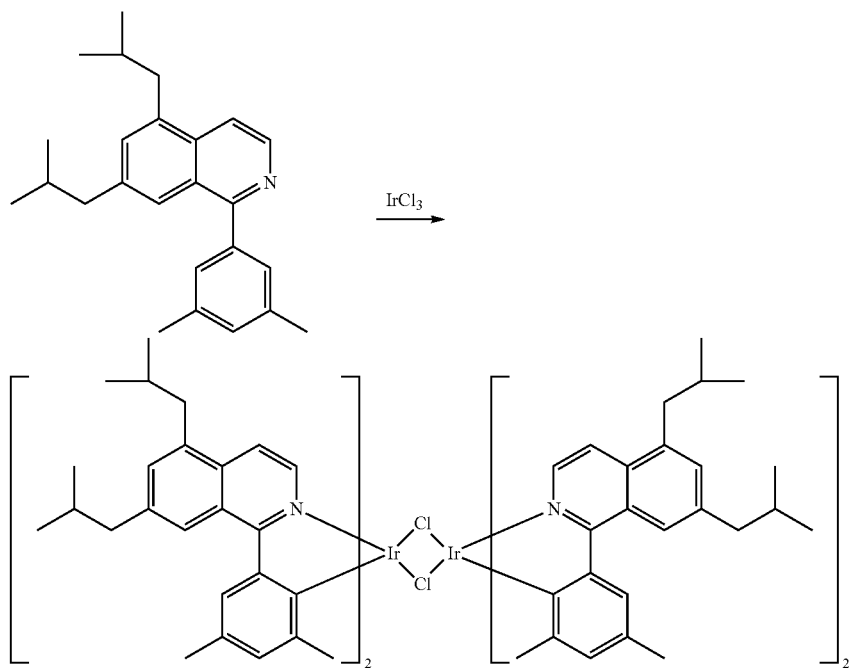

Synthesis of Iridium Dimer 1-(3,5-dimethylphenyl)-5,7-diisobutylisoquinoline (6.0 g, 17.37 mmol) and IrCl$_3$·H$_2$O (2.57 g, 6.95 mmol), 90 mL 2-ethoxylethanol and 30 mL water were charged in a 250 mL flask. The reaction mixture was heated to reflux under nitrogen for 19 hours. 3.1 g (24.3%) of dimer was obtained after filtration and washing with methanol, which was used for next step without further purification.

Synthesis of Compound 1

2-(3,5-dimethylphenyl)-5,7-diisobutylquinoline iridium dimer (1.5 g, 0.82 mmol), 2,4-pentanedione (1.63 g, 16.36 mmol), Na$_2$CO$_3$ (1.73 g, 16.36 mmol) and 2-ethoxyethanol (60 mL) were charged in a 250 flask and stirred at room temperature for 72 hours. The resulting precipitate was filtered and washed with methanol. The solid was further purified by passing it through a silica gel plug (that was

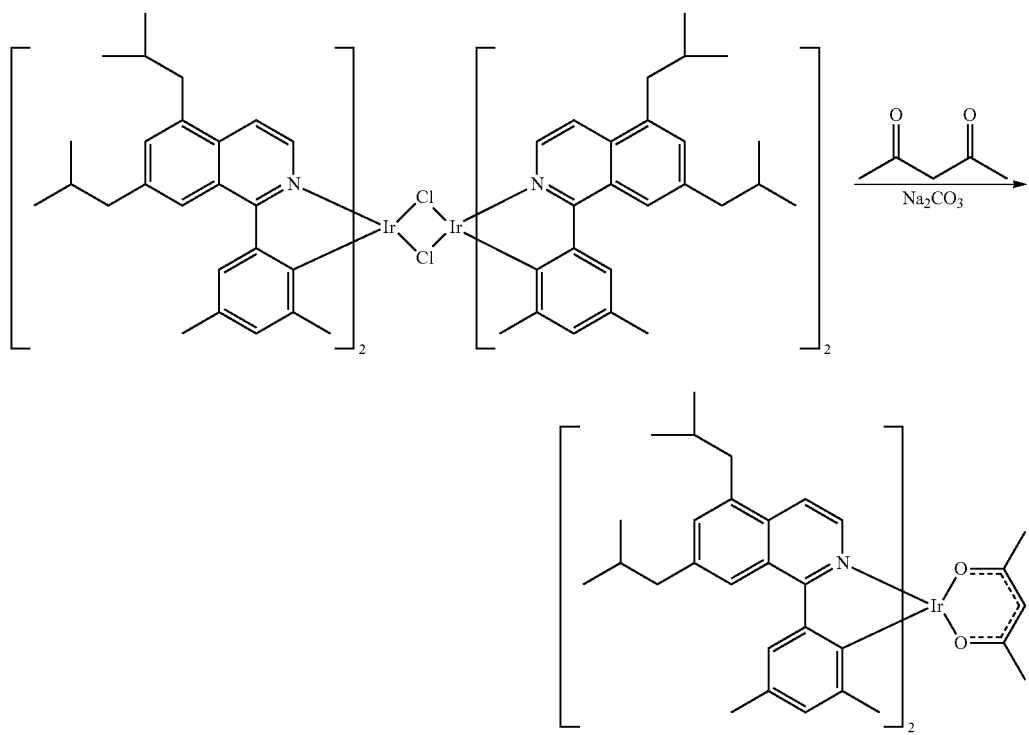

pretreated with 15% triethylamine in hexanes). 0.55 g (34.3%) of product was obtained after workup. The identity of the product was confirmed by LC-MS.

Synthesis of Compound 2

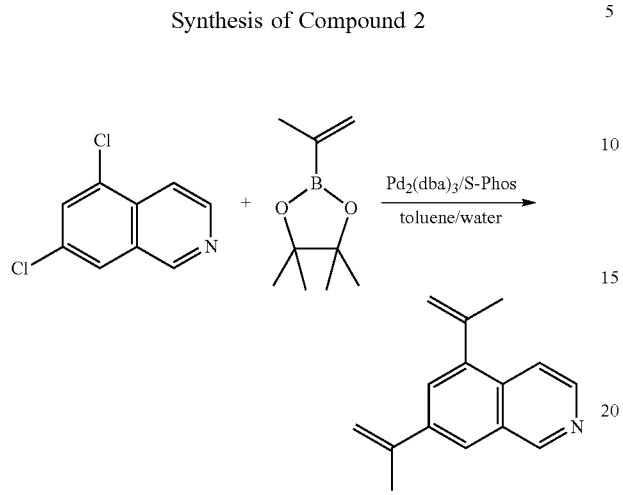

Synthesis of 5,7-di(prop-1-en-2-yl)isoquinoline 5,7-Dichloroisoquinoline (5.1 g, 25.8 mmol), 4,4,5,5-tetramethyl-2-(prop-1-en-2-yl)-1,3,2-dioxaborolane (9.95 g, 59.2 mmol), dicyclohexyl(2',6'-dimethoxy-[1,1'-biphenyl]-2-yl)phosphine (0.846 g, 2.06 mmol), Pd$_2$(dba)$_3$ (0.472 g, 0.515 mmol), K$_3$PO$_4$ (19.13 g, 90 mmol), 100 mL toluene and 10 mL water were charged in a flask. The reaction mixture was purged by bubbling N$_2$ for 30 minutes then heated to reflux overnight. GC-MS analysis showed that the reaction was complete. 5.1 g (91%) of product was obtained after silica gel column chromatography and confirmed by GC-MS.

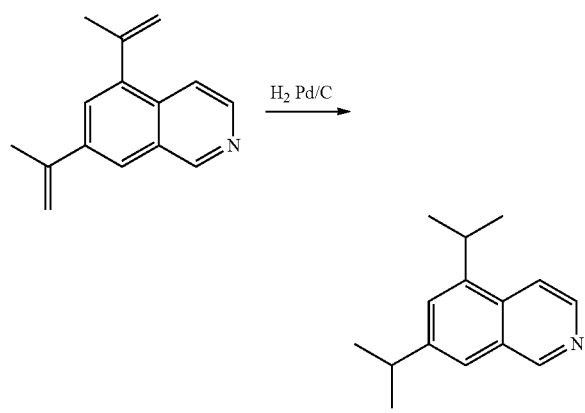

Synthesis of 5,7-diisopropyl)isoquinoline 5,7-Di(prop-1-en-2-yl)isoquinoline (5.1 g, 24.37 mmol) was dissolved in 50 mL EtOH in a glass bottle and purged with N$_2$ for 30 minutes. To the solution, 10% Pd/C (1.3 g, 1.218 mmol) was added into the bottle under nitrogen. Hydrogenation was conducted for 4 hours, after which GC-MS analysis indicated the reaction was complete.

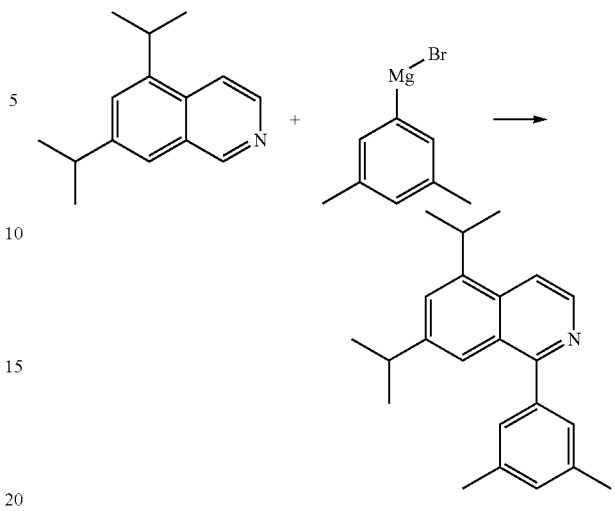

Synthesis of 1-(3,5-dimethylphenyl)-5,7-diisopropylisoquinoline 5,7-diisopropylisoquinoline (3.1 g, 14.5 mmol) in 50 mL dry THF and was added with 0.5 M (3,5-dimethylphenyl) magnesium bromide THF solution (50 mL, 25.0 mmol) dropwise at room temperature and allowed to stir for 16 hours, after which the reaction mixture was heated to reflux for 5 hours. GC and HPLC analysis indicated the reaction was complete, but contained a small amount of reduced byproducts which were converted to the desired product by treatment with DDQ in THF for few minutes. After aqueous workup, 2.4 g (52%) of product was obtained.

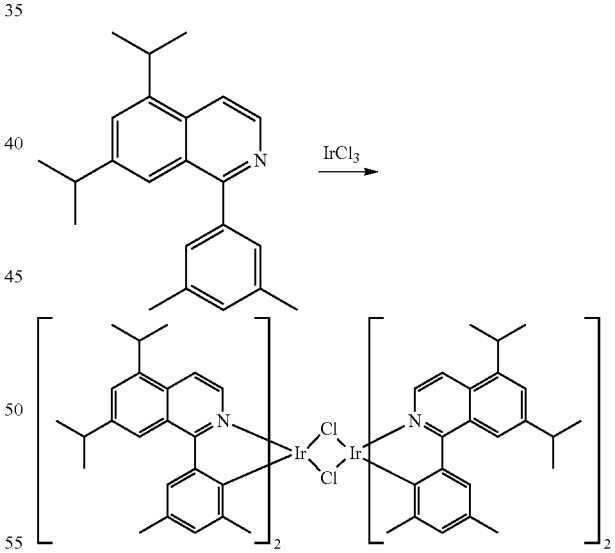

Synthesis of Iridium Dimer 1-(3,5-Dimethylphenyl)-5,7-diisopropylisoquinoline (2.4 g, 7.56 mmol) and IrCl$_3$·H$_2$O (1.167 g, 3.15 mmol), 45 mL 2-ethoxyethanol and 15 mL water were charged in a 250 mL flask. The reaction mixture was heated to reflux under nitrogen for 19 hours. After cooling the reaction, filtration, and washing with methanol, 1.2 g (44.2%) of dimer was obtained, which was used for next step without further purification.

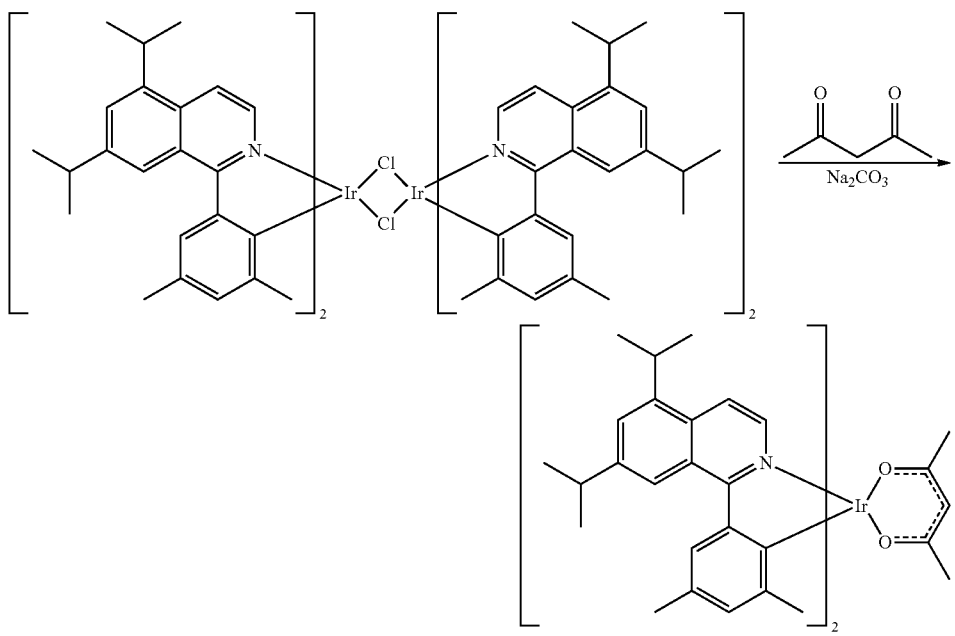

Synthesis of Compound 2

2-(3,5-Dimethylphenyl)-5,7-diisopropylquinoline iridium dimer (1.2 g, 0.697 mmol), 2,4-pentanedione (0.697 g, 6.97 mmol), Na$_2$CO$_3$ (0.739 g, 6.97 mmol) and 2-ethoxyethanol (40 mL) were stirred at room temperature for 48 hours. The precipitate was filtered and washed with methanol. The solid was further purified by passing it through a silica gel plug (pretreated with 15% tryethylamine in hexanes). After workup of the reaction 0.68 g (52.8%) of product was obtained, which was confirmed by LC-MS.

Synthesis of Compound 3

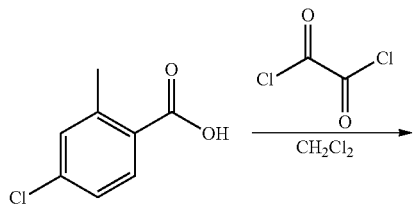

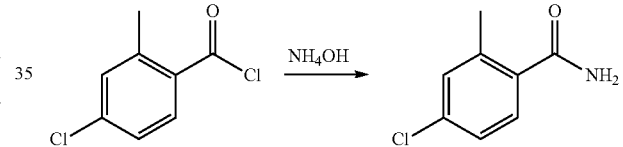

Synthesis of 4-Chloro-2-methylbenzoyl chloride

To a mixture of 4-chloro-2-methylbenzoic acid (24.0 g, 141 mmol) in dichloromethane (20 mL) and dimethylformamide (4 mL) at room temperature was added dropwise oxalyl chloride (26.8 g, 258 mmol). The reaction was stirred room temperature for 2 hours. Hexanes were added and the reaction mass was concentrated to give 4-chloro-2-methylbenzoyl chloride (26.6 g, quantitative) and used in the next step without purification.

Synthesis of 4-Chloro-2-methylbenzamide

30% Ammonium hydroxide (300 mL, 4.76 mol) was cooled in a salt ice bath. 4-chloro-2-methylbenzoyl chloride (26.4 g, 140 mmol) in tetrahydrofuran (150 mL) added and stirred for 1 hr. Water was added. Crystals were filtered off and washed with water and dried under vacuum to give 4-chloro-2-methylbenzamide (20.0 g, 84% yield).

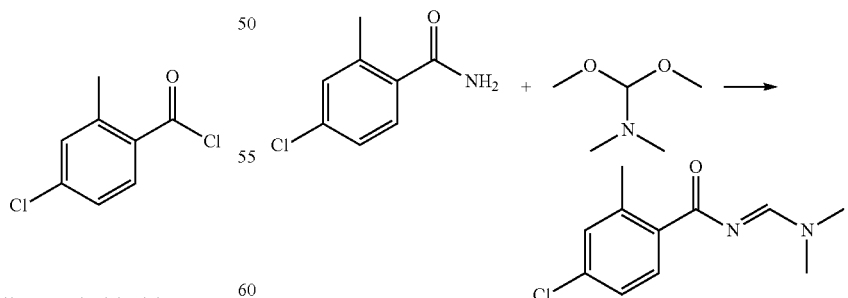

Synthesis of 4-Chloro-N-((dimethylamino)methylene)-2-methylbenzamide

A mixture of 4-chloro-2-methylbenzamide (20.8 g, 123 mmol) and 1,1-dimethylmethaneamine (17.5 g, 147 mmol)

in tetrahydrofuran (250 mL) was refluxed for 2.5 hours and then concentrated. The resulting crystals were triturated in hexanes and filtered to give 4-chloro-N-((dimethylamino)methylene)-2-methylbenzamide (25.7 g, 93% yield).

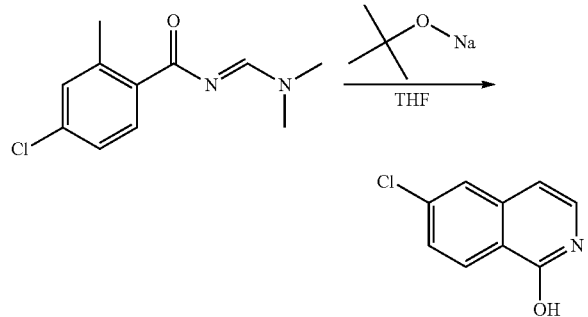

Synthesis of 6-Chloroisoquinolin-1-ol

A mixture of 4-chloro-N-((dimethylamino)methylene)-2-methylbenzamide (25.7 g, 114 mmol), sodium tert-butoxide (25.7 g, 267 mmol) and tetrahydrofuran (450 mL) was refluxed under N₂ for 3 hours and then poured into water (1 L). The pH was adjusted to 4 with aqueous HCl. The solids were filtered off and washed with water and dried under vacuum to give 6-chloroisoquinolin-1-ol (14.7 g, 71.6% yield).

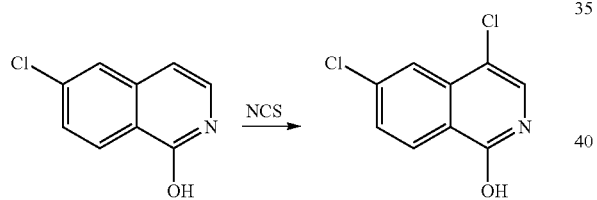

Synthesis of 4,6-Dichloroisoquinolin-1-ol

A mixture of 6-chloroisoquinolin-1-ol (13.5 g, 75 mmol) and acetonitrile (400 mL) was heated to reflux. N-Chlorosuccinimide (10.57 g, 79 mmol) in acetonitrile (110 mL) was added dropwise. The mixture was refluxed overnight. Crystals were filtered off. The filtrate was concentrated and the resulting crystals were washed with water and combined with the above crystals and dried under vacuum to give 4,6-dichloroisoquinolin-1-ol (14.2 g, 88% yield). It was taken on without analysis to the next step.

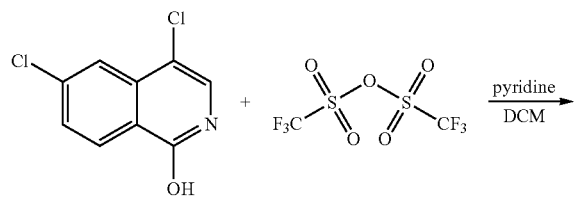

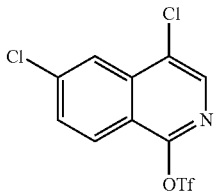

Synthesis of 4,6-Dichloroisoquinolin-1-yl trifluoromethanedsulfonate. A mixture of 4,6-dichloroisoquinolin-1-ol (14.2 g, 66.5 mmol), pyridine (10.8 mL, 133 mmol) and dichloromethane (200 mL) was cooled in an ice bath. Trifluoromethanesulfonic anhydride (22.4 mL, 133 mmol) was added dropwise. The mixture was stirred overnight at room temperature. Water was added and NaHCO₃ (20 g) was added slowly. The organic layer was dried over Na₂SO₄, concentrated and flash chromatographed using silica gel chromatography (4:1 hexanes:dichloromethane, v/v) to give 4,6-dichloroisoquinolin-1-yl trifluoromethanedsulfonate (3.7 g, 16% yield).

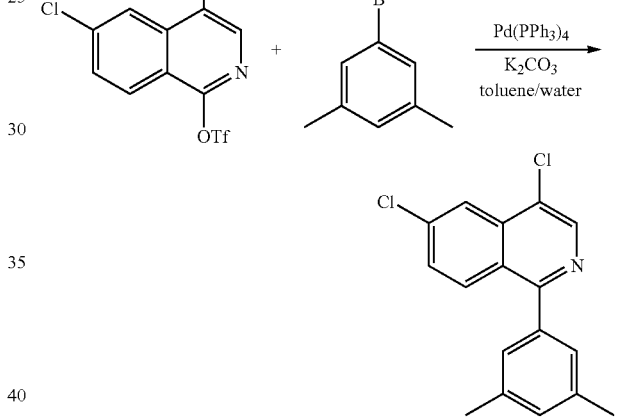

Synthesis of 4,6-Dichloro-1-(3,5-dimethylphenyl)isoquinoline

A mixture of 4,6-dichloroisoquinolin-1-yl trifluoromethanesulfonate (4.0 g, 11.6 mmol), 3,5-dimthylphenyl)boronic acid (1.6 g, 10.8 g), Pd(PPh₃)₄ (0.67 g, 0.58 mmol), potassium carbonate (4.79, 34.7 mmol), toluene (100 mL) and water (10 mL) was purged with nitrogen and refluxed overnight. The concentrated toluene layer was chromatographed using silica gel chromatography (2:1 hexanes:dichloromethane, v/v) to give 4,6-dichloro-1-(3,5-dimethylphenyl)isoquinoline (3.0 g, 92% yield).

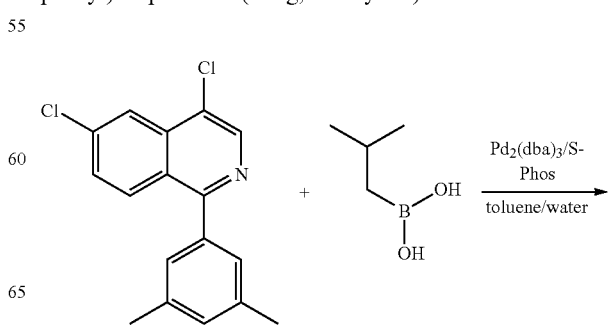

Synthesis of 1-(3,5-Dimethylphenyl)isoquinoline

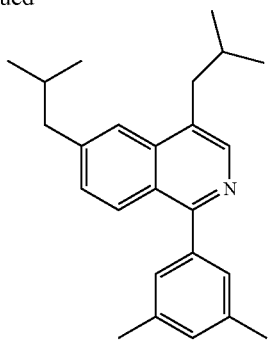

A mixture of 4,6-dichloro-1-(3,5-dimethylphenyl)isoquinoline (3.2 g, 10.59 mmol), isobutylboronic acid (4.32 g, 42.4 mmol), $Pd_2(dba)_3$ (0.388 g, 0.424 mmol), dicyclohexyl (2',6'-dimethoxy-[1,1'-biphenyl]-2-yl)phosphine (0.696 g, 1.694 mmol), $K_3PO_4 \cdot H_2O$ (24.38 g, 106 mmol), toluene (133 mL) and water (11 mL) were purged with nitrogen for 30 minutes and refluxed overnight. The toluene layer was chromatographed using silica gel chromatography (100% dichloromethane to 4:1 dichloromethane:ethyl acetate, v/v) to give 1-(3,5-dimethylphenyl)isoquinoline (3.3 g, 90% yield).

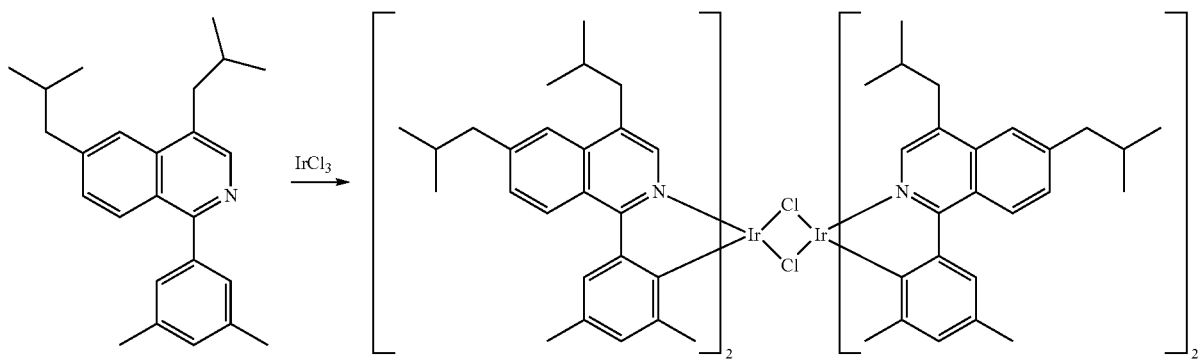

Synthesis of 1-(3,5-Dimethylphenyl)isoquinoline Iridium dimer

A mixture of 1-(3,5-dimethylphenyl)-4,6-diisobutylisoquinoline (3.3 g, 9.55 mmol), $IrCl_3 \cdot 3H_2O$ (1.475 g, 3.98 mmol), 2-ethoxyethanol (45 mL) and water (15 mL) were refluxed overnight and then filtered and washed with methanol to give 1-(3,5-dimethylphenyl)isoquinoline iridium dimer (2.0 g, 54.8% yield).

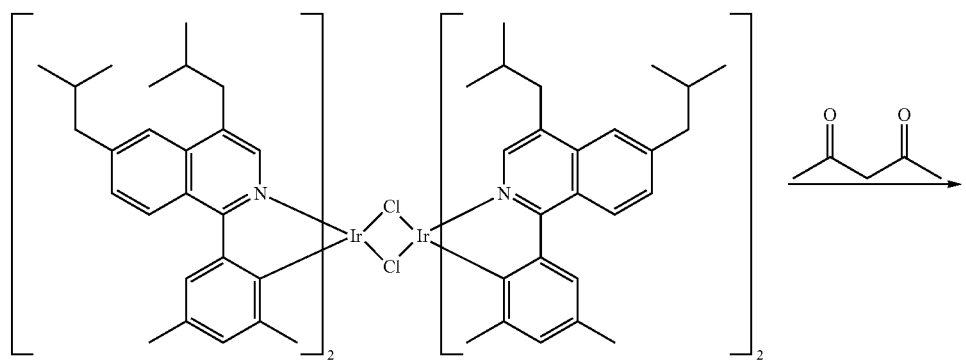

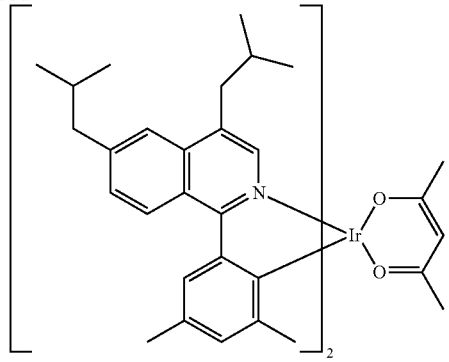

Synthesis of Compound 3

A mixture of 1-(3,5-dimethylphenyl)isoquinoline iridium dimer (1.2 g, 0.655 mmol), pentane-2,4-dione (0.655 g, 6.55 mmol), potassium carbonate (0.905 g, 6.55 mmol) and 2-ethoxyethanol (60 mL) was stirred at room temperature overnight and filtered, washed with methanol and chromaographed using silica gel chromatography (4:1 hexanes:dichloromethane, v/v, silica gel pre-treated with triethylamine). The residue was dissolved in dichloromethane and 2-propanol. The dichloromethane was removed on a rotoevaporator and 0.68 g of crystals were filtered off and then sublimed at 230° C. to give Compound 3 (0.32 g, 24.9%), which was confirmed by LC-MS.

Synthesis of Compound 22

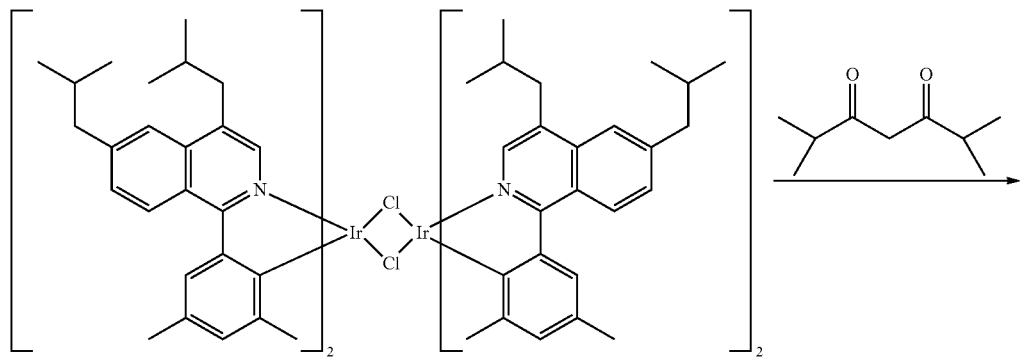

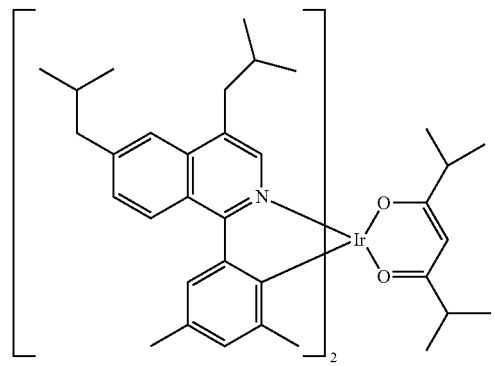

Synthesis of Compound 22

A mixture of 1-(3,5-dimethylphenyl)isoquinoline iridium dimer (0.8 g, 0.436 mmol), 2,6-dimethylheptane-3,5-dione (0.682 g, 4.36 mmol), potassium carbonate (0.603 g, 4.36 mmol) and 2-ethoxyethanol (60 mL) were stirred at room temperature overnight and filtered, washed with methanol and chromaographed on silica gel (4:1 hexanes:dichloromethane, v/v, silica gel pre-treated with triethylamine). The residue was dissolved in dichloromethane and 2-propanol. The dichloromethane was removed on a rotoevaporator and 0.60 g of crystals were obtained after filtration. It was confirmed by LC-MS.

It is understood that the various embodiments described herein are by way of example only, and are not intended to limit the scope of the invention. For example, many of the materials and structures described herein may be substituted with other materials and structures without deviating from the spirit of the invention. The present invention as claimed

The invention claimed is:

1. A compound having the formula:

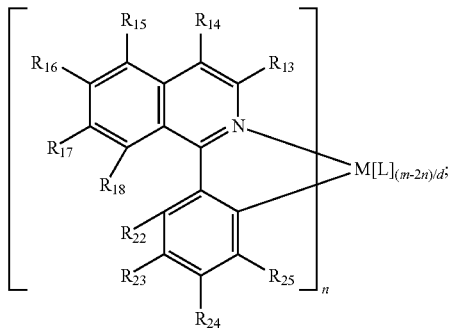

Formula I wherein M is a metal having an atomic weight higher than 40;

wherein L is a second ligand;

wherein m is the maximum coordination number of the metal M;

wherein d is the denticity of L;

wherein n is at least 1;

wherein one of $R_{13}$, $R_{14}$, $R_{15}$, $R_{16}$, $R_{17}$, and $R_{18}$ is hydrogen and the remainder are independently selected from the group consisting of hydrogen, deuterium, halide, alkyl, cycloalkyl, heteroalkyl, arylalkyl, alkoxy, aryloxy, amino, silyl, germyl, alkenyl, cycloalkenyl, heteroalkenyl, alkynyl, aryl, heteroaryl, acyl, carbonyl, carboxylic acids, ester, nitrile, isonitrile, sulfanyl, sulfonyl, sulfonyl, phosphino, and combinations thereof;

wherein at least two of $R_{13}$, $R_{14}$, $R_{15}$, $R_{16}$, $R_{17}$, and $R_{18}$ are independently selected from two to three carbon containing alkyl, silyl, germyl, cycloalkyl, and combinations thereof;

wherein each of $R_{22}$, $R_{23}$, $R_{24}$, and $R_{25}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein at least one of the following (i)-(ii) is true:
(i) at least one of $R_{13}$ to $R_{18}$ is cycloalkyl or germyl; and
(ii) at least one of $R_{13}$ to $R_{18}$ is silyl, $R_{23}$ and $R_{25}$ are alkyl, and $R_{22}$ and $R_{24}$ are hydrogen.

2. The compound of claim 1, wherein two of $R_{13}$ to $R_{18}$ are alkyl substitutions.

3. The compound of claim 1, wherein at least one of $R_{13}$ to $R_{18}$ represents a silyl or a germyl substitution.

4. The compound of claim 1, wherein the compound has the formula:

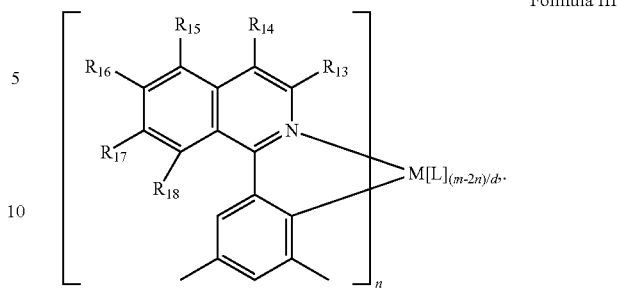

Formula III

5. The compound of claim 1, wherein at least one of $R_{13}$, $R_{15}$, $R_{16}$, and $R_{18}$ is selected from the group consisting of ethyl and $CH(CH_3)_2$, or
at least one of $R_{13}$ to $R_{18}$ is selected from the group consisting of cyclopentyl, cyclohexyl, trimethylsilyl, triethylsilyl, triisopropylsilyl, trimethylgermyl, triethylgermyl, and triisopropylgermyl.

6. The compound of claim 1, wherein M is Ir.

7. The compound of claim 1, wherein n is 2.

8. The compound of claim 1, wherein L is a monoanionic bidentate ligand.

9. The compound of claim 8, wherein L is

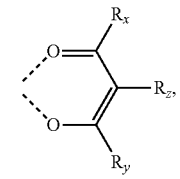

and
wherein $R_x$, $R_y$, and $R_z$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

10. The compound of claim 9, wherein $R_x$, $R_y$, and $R_z$ are independently selected from the group consisting of alkyl, hydrogen, deuterium, and combinations thereof.

11. The compound of claim 10, wherein $R_z$ is hydrogen or deuterium, and $R_x$ and $R_y$ are independently selected from the group consisting of methyl, $CH(CH_3)_2$, and $CH_2CH(CH_3)_2$.

12. The compound of claim 9, wherein the compound has the formula:

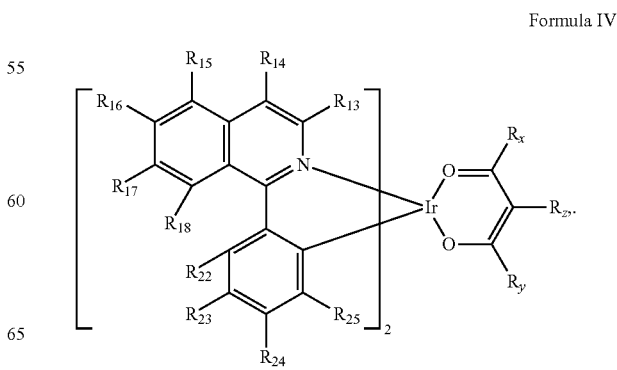

Formula IV

13. The compound of claim 1, wherein the compound is selected from the group consisting of:
Compound 17
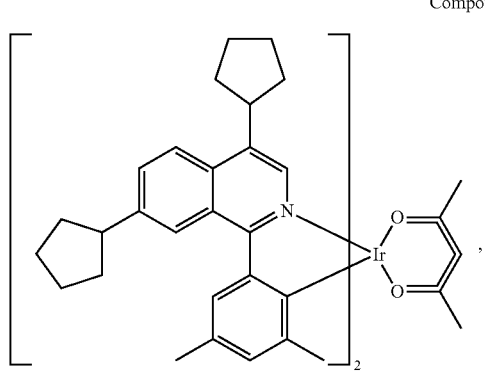
Compound 18
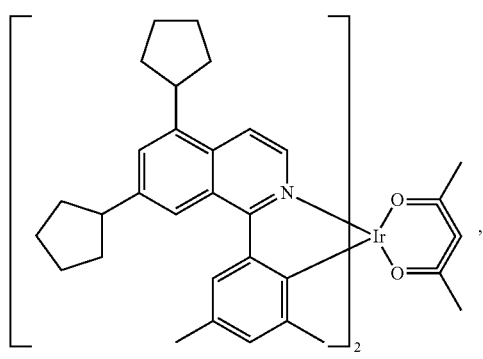
Compound 19
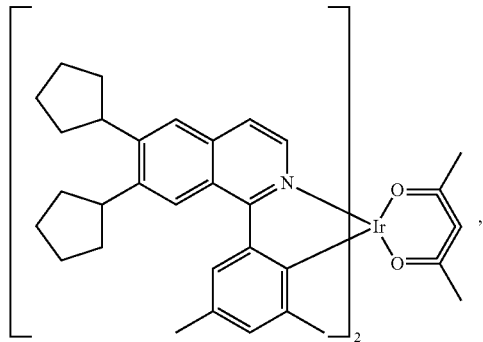
Compound 35
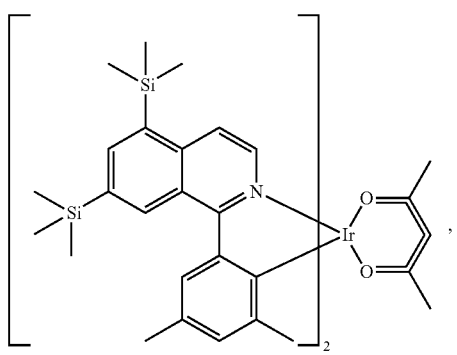
Compound 36
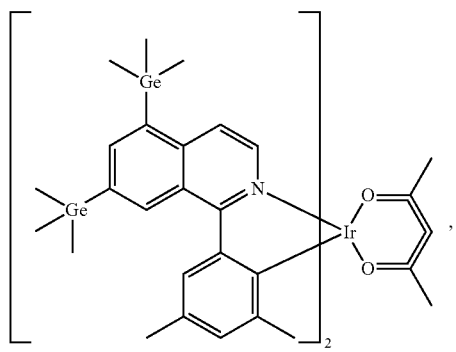
Compound 37
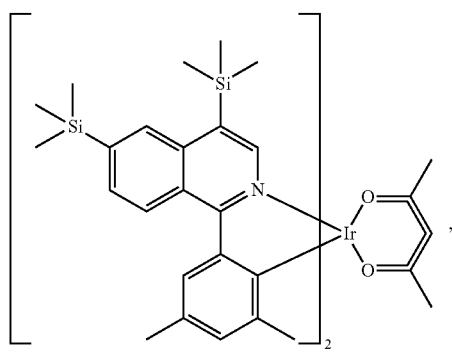
Compound 38
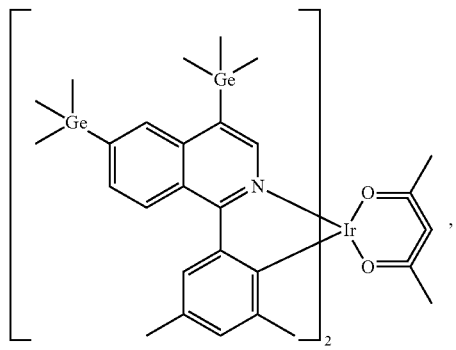
Compound 41
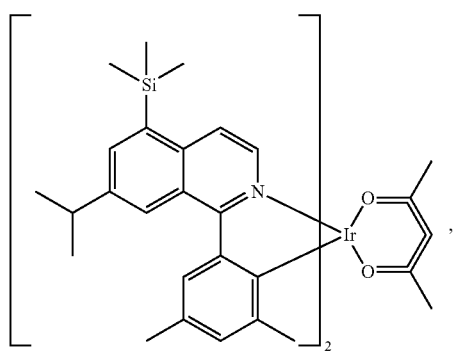

-continued

Compound 42

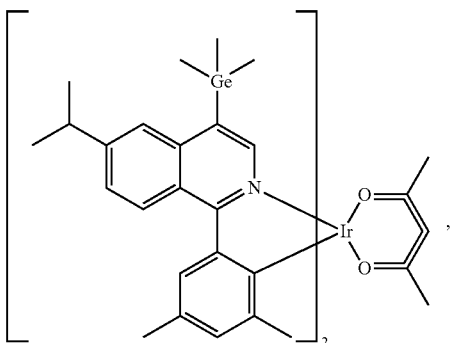

Compound 43

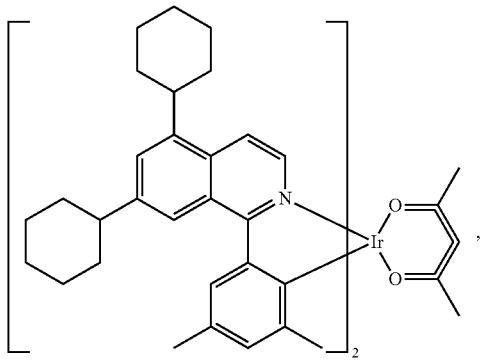

Compound 44

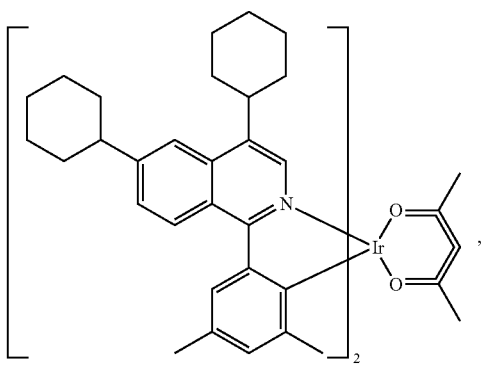

Compound 45

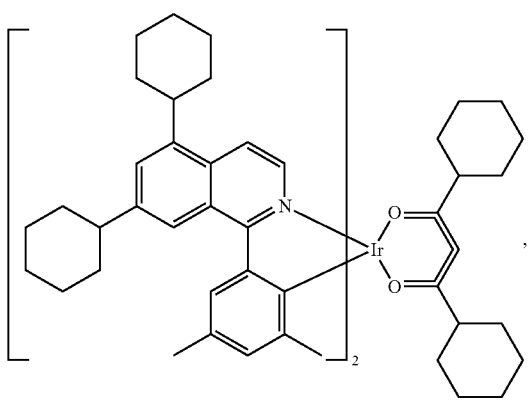

and

-continued

Compound 46

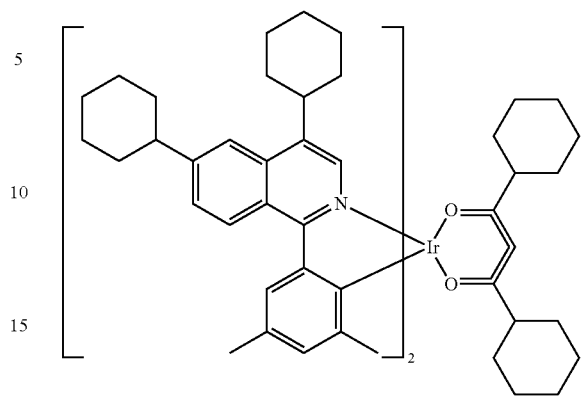

14. A first device comprising a first organic light emitting device, comprising:
   an anode;
   a cathode; and
   an organic layer, disposed between the anode and the cathode, comprising a compound having the formula:

Formula I

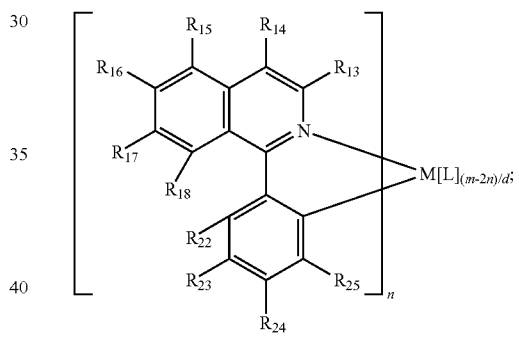

wherein M is a metal having an atomic weight higher than 40;
wherein L is a second ligand;
wherein m is the maximum coordination number of the metal M;
wherein d is the denticity of L;
wherein n is at least 1;
wherein one of $R_{13}$, $R_{14}$, $R_{15}$, $R_{16}$, $R_{17}$, and $R_{18}$ is hydrogen and the remainder are independently selected from the group consisting of hydrogen, deuterium, halide, alkyl, cycloalkyl, heteroalkyl, arylalkyl, alkoxy, aryloxy, amino, silyl, germyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein at least two of $R_{13}$, $R_{14}$, $R_{15}$, $R_{16}$, $R_{17}$, and $R_{18}$ are independently selected from two to three carbon containing alkyl, silyl, germyl, cycloalkyl, and combinations thereof;
wherein each of $R_{22}$, $R_{23}$, $R_{24}$, and $R_{25}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein at least one of the following (i)-(ii) is true:

(i) at least one of $R_{13}$ to $R_{18}$ is cycloalkyl or germyl; and (ii) at least one of $R_{13}$ to $R_{13}$ is silyl, $R_{23}$ and $R_{25}$ are alkyl, and $R_{22}$ and $R_{24}$ are hydrogen.

15. The first device of claim 14, wherein the first device is a consumer product or an organic light-emitting device.

16. The first device of claim 14, wherein the organic layer is an emissive layer and the compound is a non-emissive dopant.

17. The first device of claim 14, wherein the organic layer further comprises a host.

18. The first device of claim 17, wherein the host is a metal 8-hydroxyquinolate.

19. The first device of claim 17, wherein the host is selected from the group consisting of:

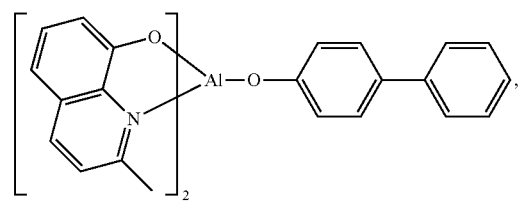

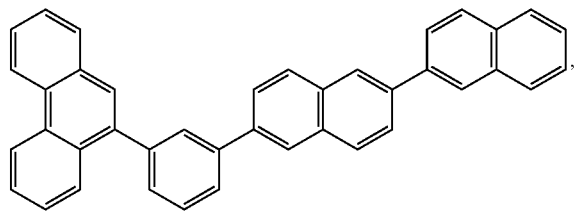

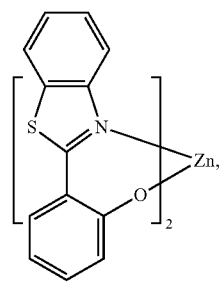

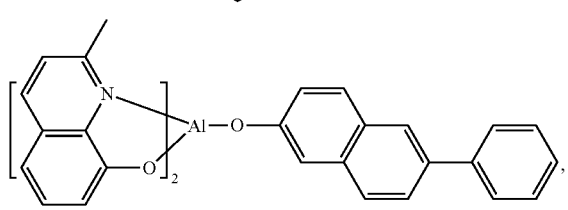

and combinations thereof.

20. The first device of claim 14, wherein the compound is selected from the group consisting of:

Compound 17

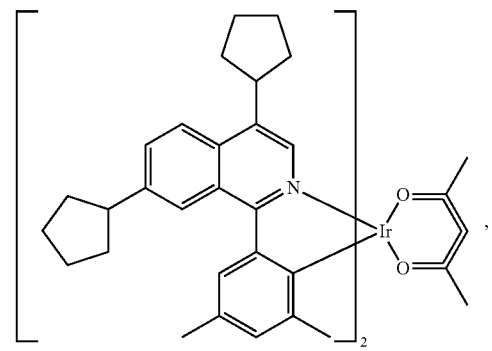

Compound 18

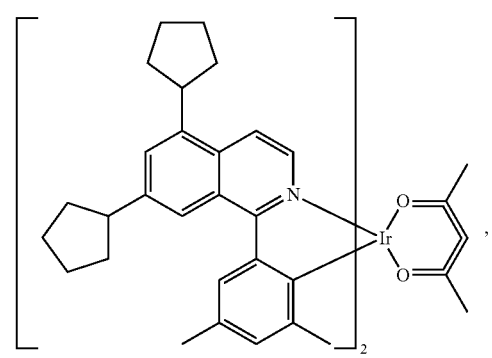

Compound 19

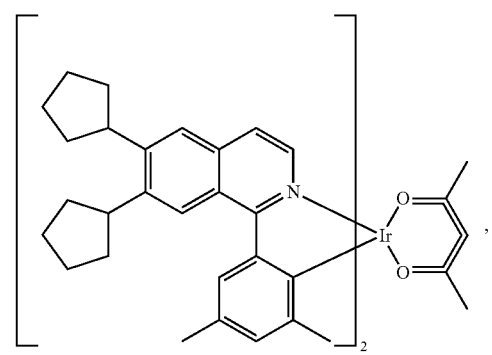

Compound 35

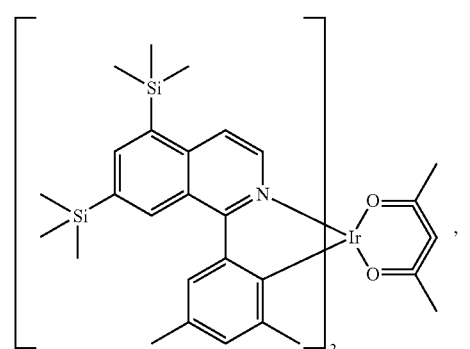

Compound 36
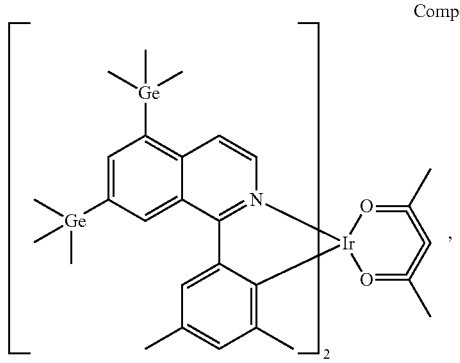
Compound 37
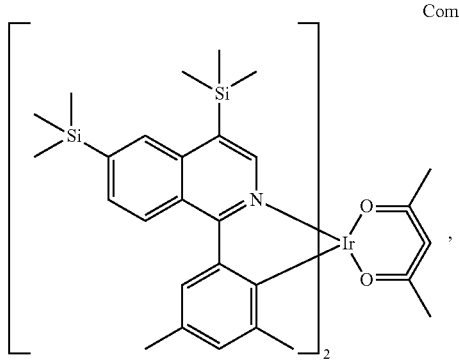
Compound 38
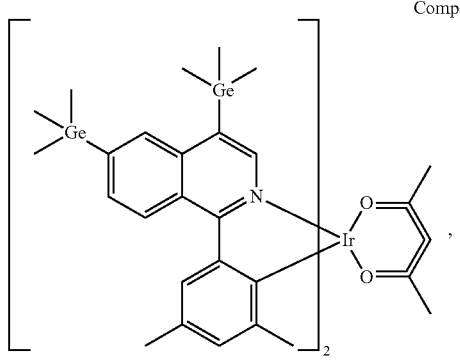
Compound 41
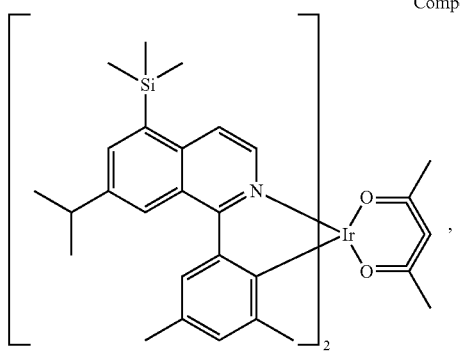
Compound 42
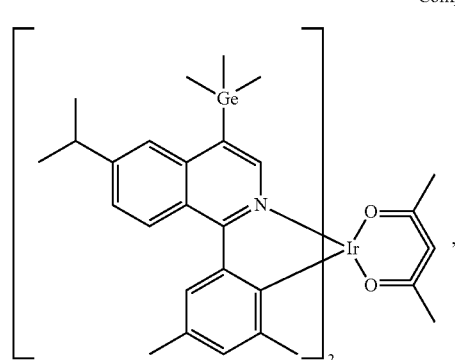
Compound 43
Compound 44
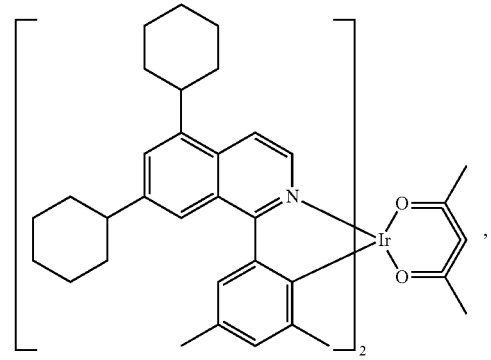
Compound 45
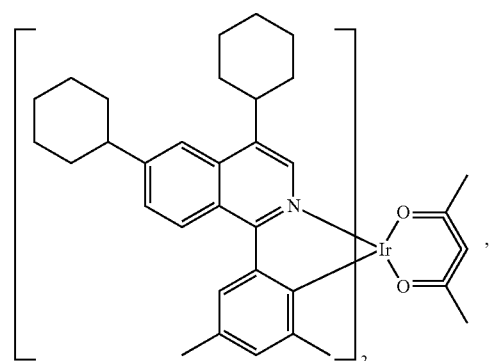
and Compound 46
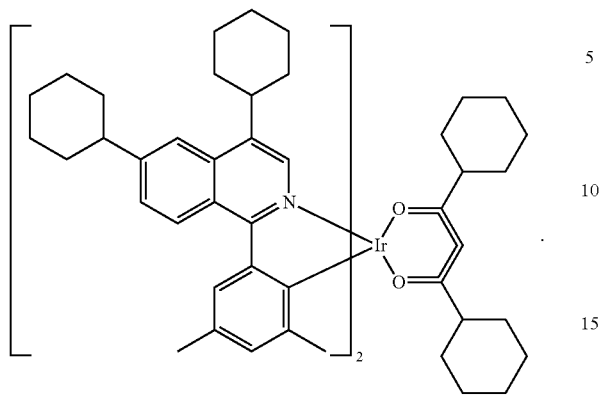
* * * * *

UNITED STATES PATENT AND TRADEMARK OFFICE
CERTIFICATE OF CORRECTION

PATENT NO. : 9,512,355 B2
APPLICATION NO. : 13/316162
DATED : December 6, 2016
INVENTOR(S) : Bin Ma, Alan DeAngelis and Chuanjun Xia Page 1 of 10

It is certified that error appears in the above-identified patent and that said Letters Patent is hereby corrected as shown below:

In the Claims
In Claim 1, Column 125, Line 43, please delete "sulfonyl" and insert -- sulfinyl --
In Claim 13, Column 127, Lines 5-19, please delete

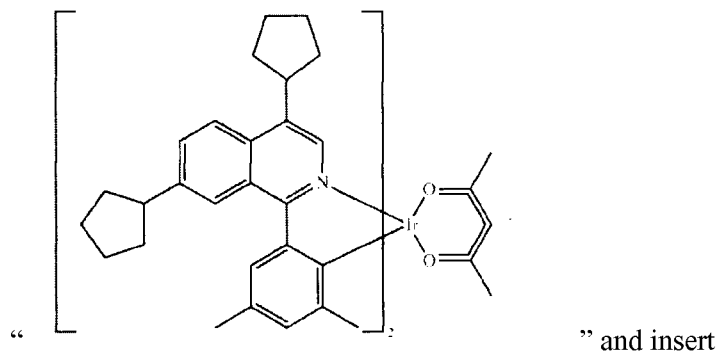

" and insert

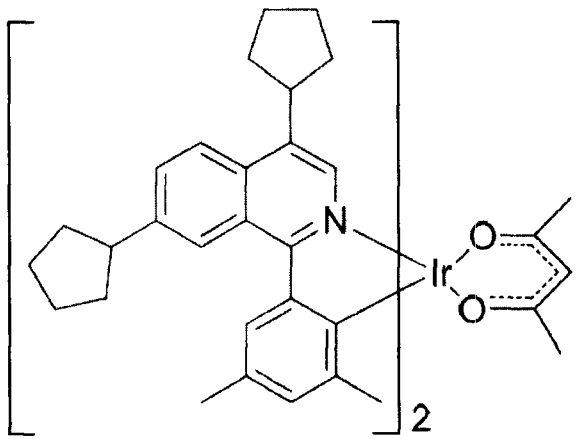

Compound 17

--

Signed and Sealed this
Eleventh Day of April, 2017

Michelle K. Lee
*Director of the United States Patent and Trademark Office*

CERTIFICATE OF CORRECTION (continued)
U.S. Pat. No. 9,512,355 B2

In Claim 13, Column 127, Lines 20-35, please delete

" 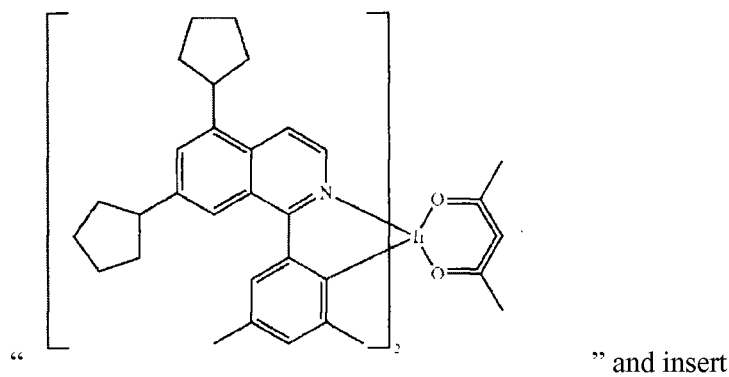 " and insert

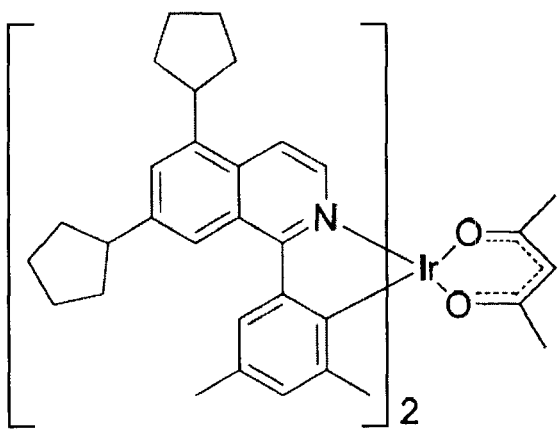

Compound 18

-- --

In Claim 13, Column 127, Lines 36-51, please delete

" 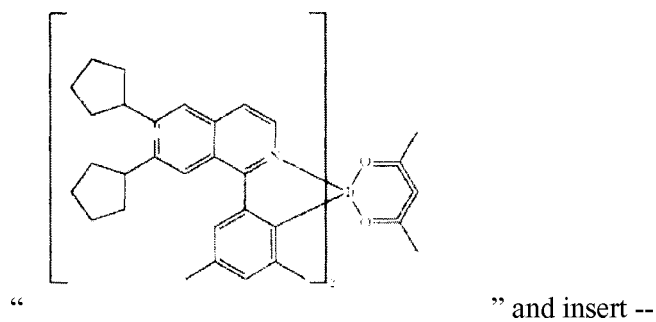 " and insert -- 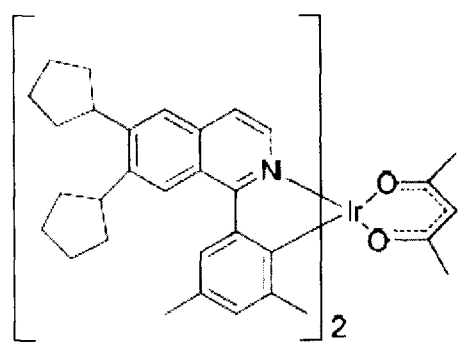

Compound 19

--

CERTIFICATE OF CORRECTION (continued)
U.S. Pat. No. 9,512,355 B2

In Claim 13, Column 127, Lines 52-66, please delete

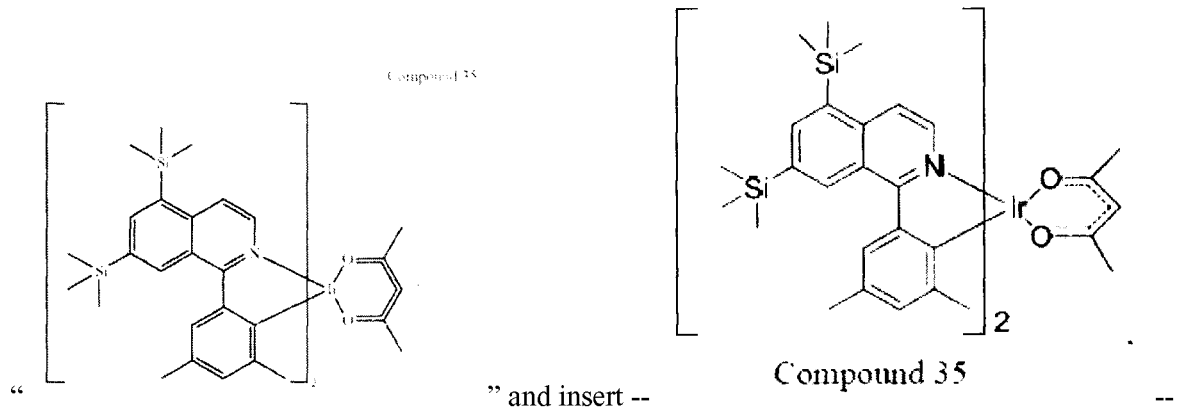

" and insert --

In Claim 13, Column 128, Lines 1-16, please delete

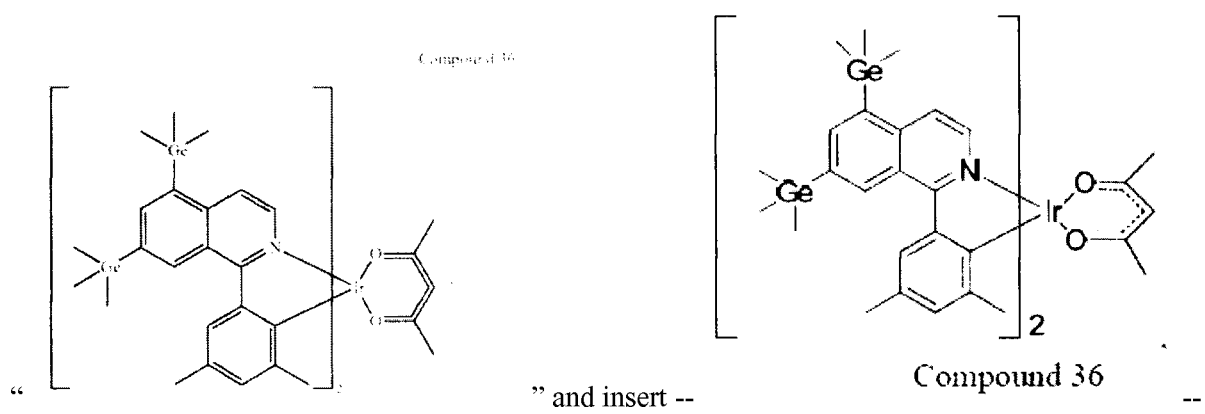

" and insert --

In Claim 13, Column 128, Lines 17-33, please delete

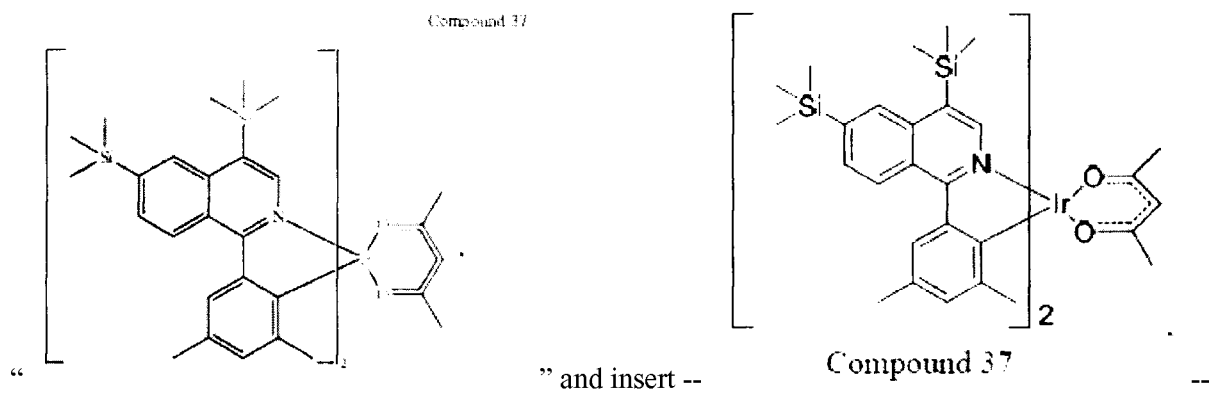

" and insert --

CERTIFICATE OF CORRECTION (continued)
U.S. Pat. No. 9,512,355 B2

Page 4 of 10

In Claim 13, Column 128, Lines 34-49, please delete

"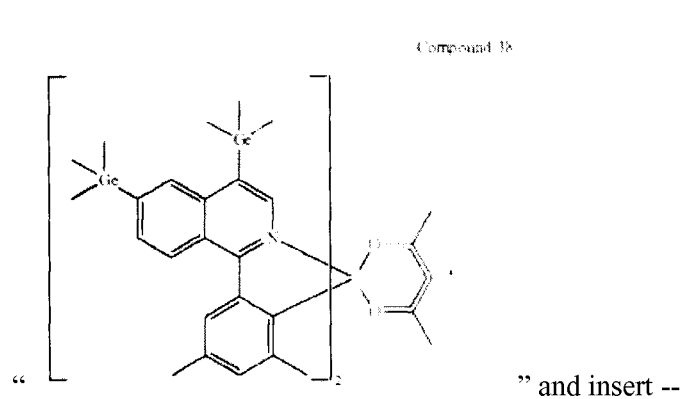" and insert -- 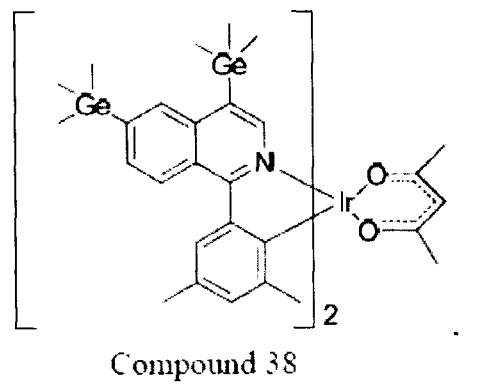

Compound 38

--

In Claim 13, Column 128, Lines 50-66, please delete

"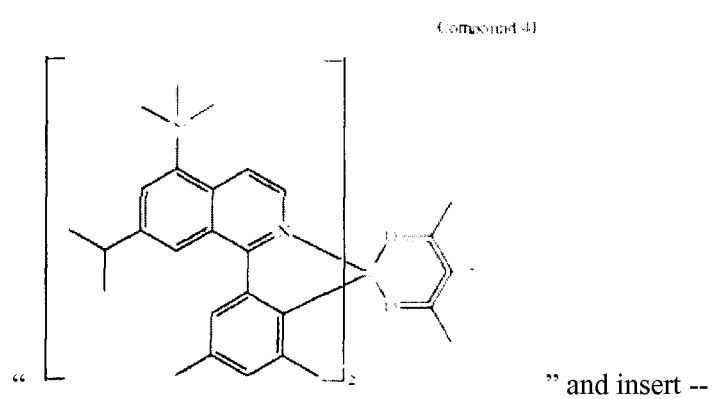" and insert -- 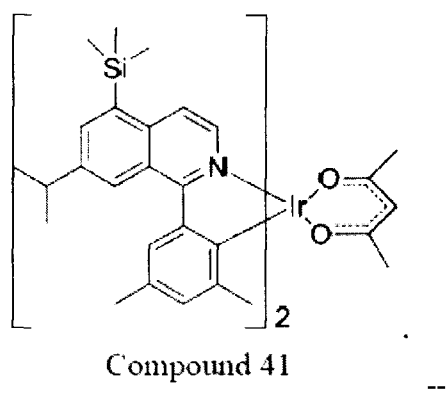

Compound 41

--

In Claim 13, Column 129, Lines 1-16, please delete

"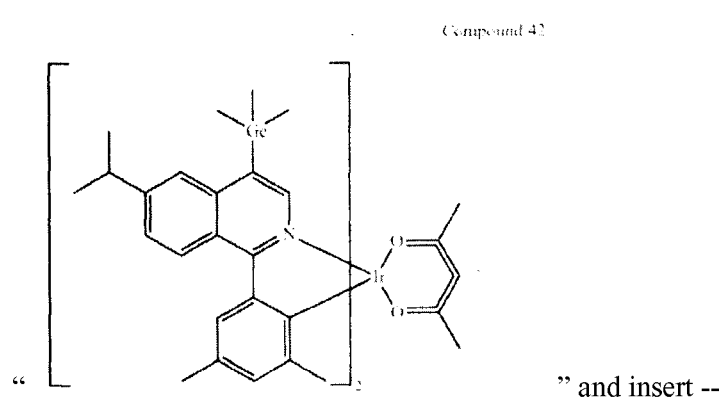" and insert -- 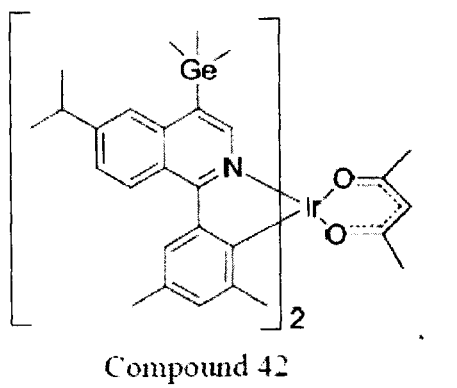

Compound 42

--

CERTIFICATE OF CORRECTION (continued)
U.S. Pat. No. 9,512,355 B2

In Claim 13, Column 129, Lines 17-31, please delete

" 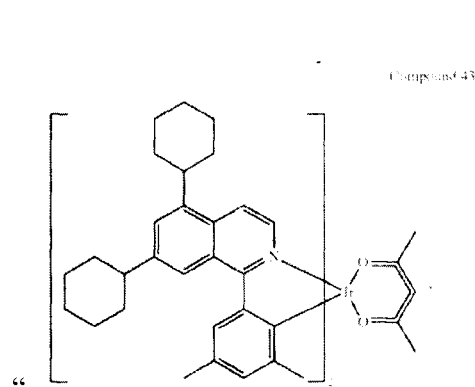 " and insert -- 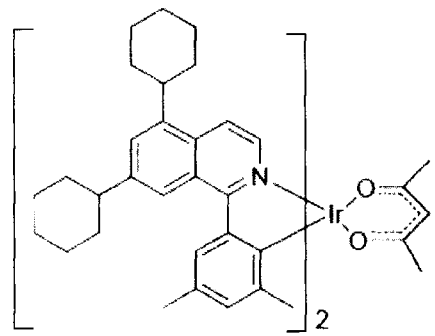

Compound 43

--

In Claim 13, Column 129, Lines 32-47, please delete

" 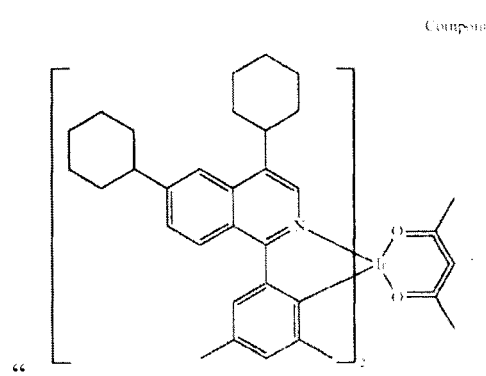 " and insert -- 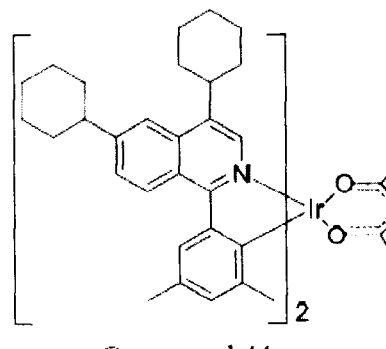

Compound 44

--

In Claim 13, Column 129, Lines 48-64, please delete

" 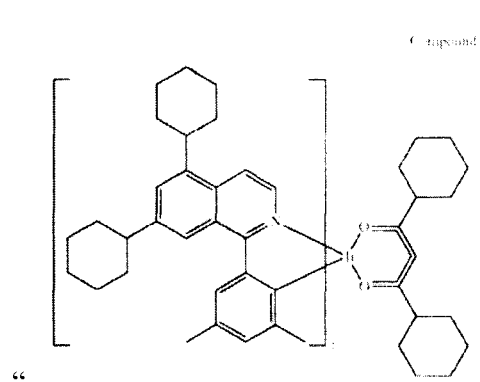 " and insert -- 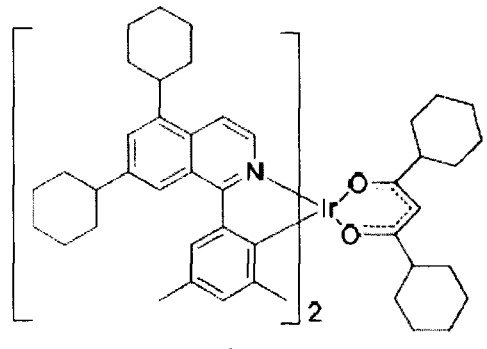

Compound 45

--

CERTIFICATE OF CORRECTION (continued)
U.S. Pat. No. 9,512,355 B2

Page 6 of 10

In Claim 13, Column 130, Lines 1-18, please delete

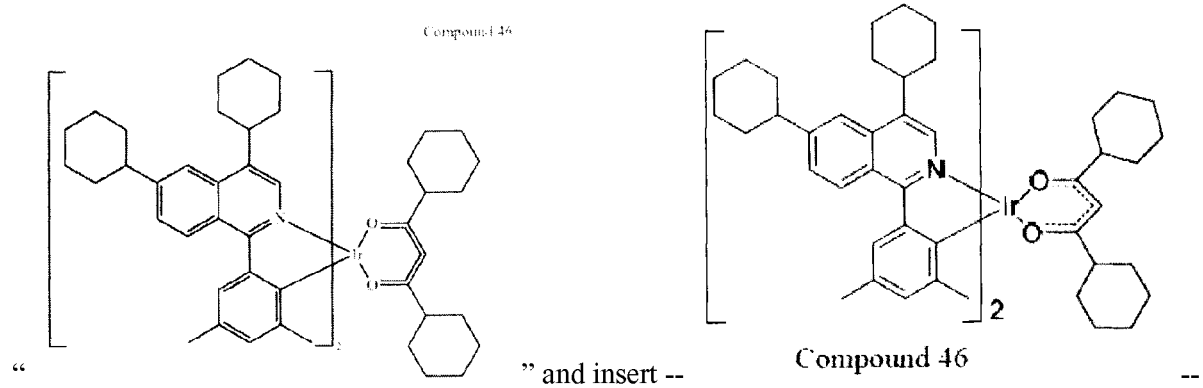

" and insert --Compound 46--

In Claim 20, Column 132, Lines 1-16, please delete

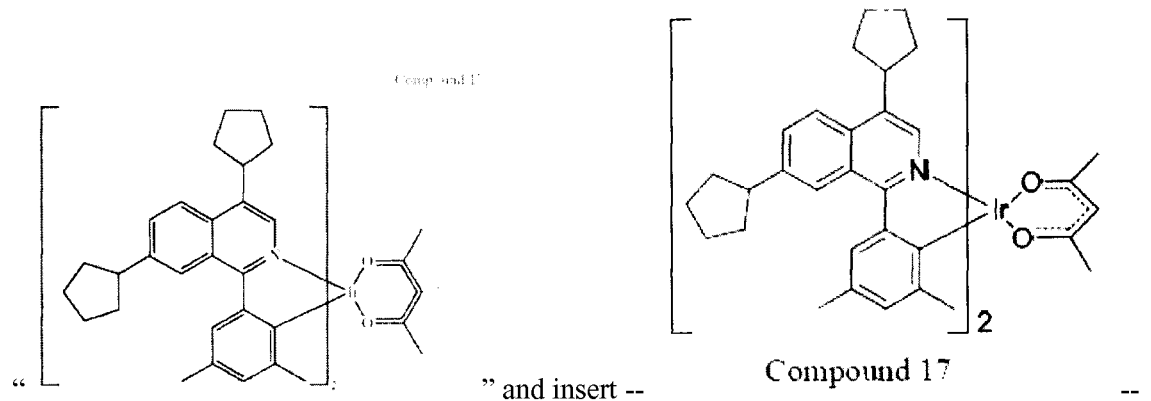

" and insert --Compound 17--

In Claim 20, Column 132, Lines 17-33, please delete

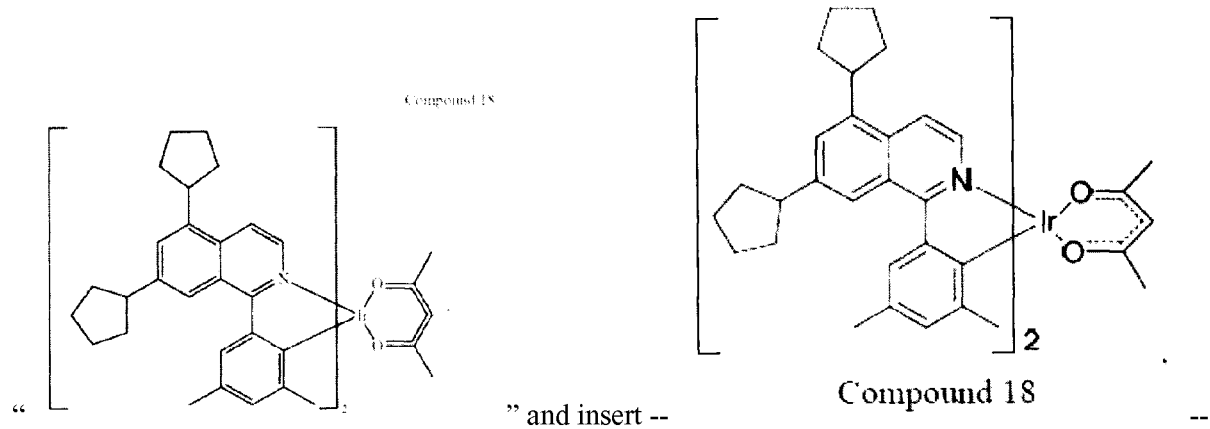

" and insert --Compound 18--

CERTIFICATE OF CORRECTION (continued)
U.S. Pat. No. 9,512,355 B2

In Claim 20, Column 132, Lines 37-49, please delete "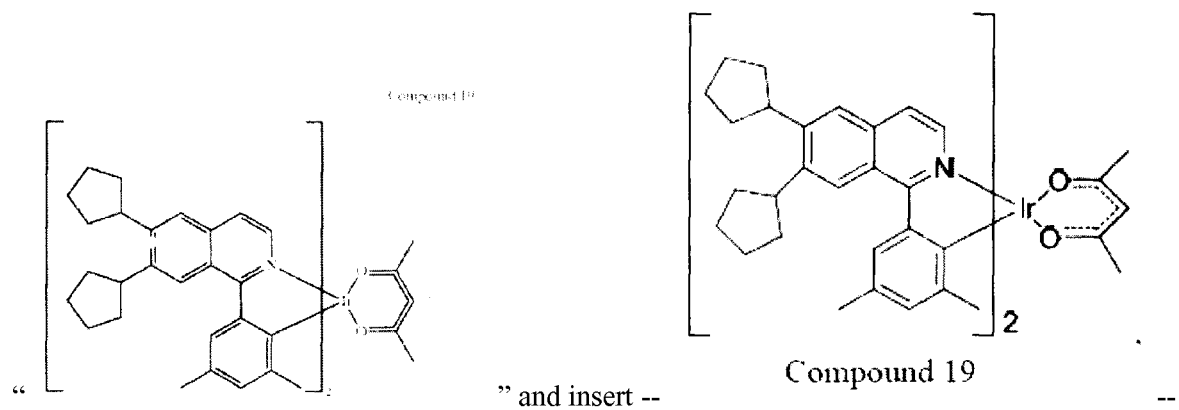" and insert --Compound 19--

In Claim 20, Column 132, Lines 50-66, please delete "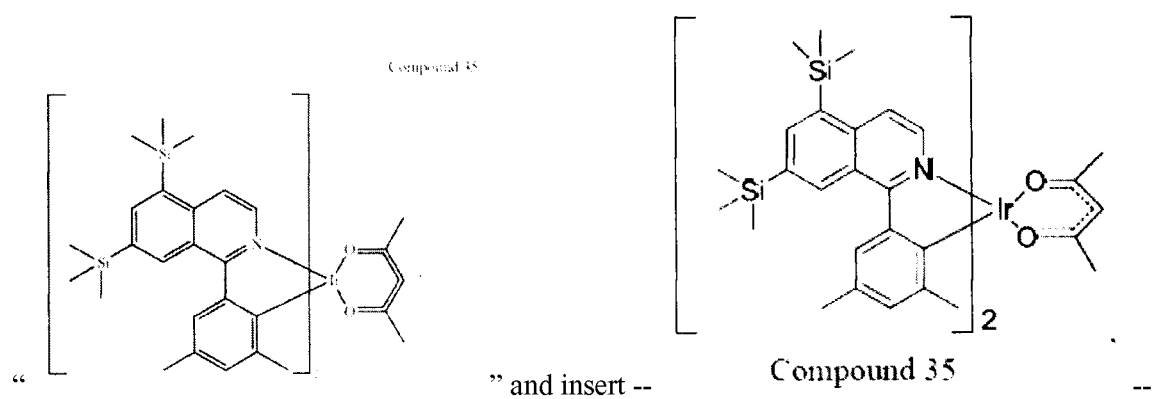" and insert --Compound 35--

In Claim 20, Column 133, Lines 1-15, please delete "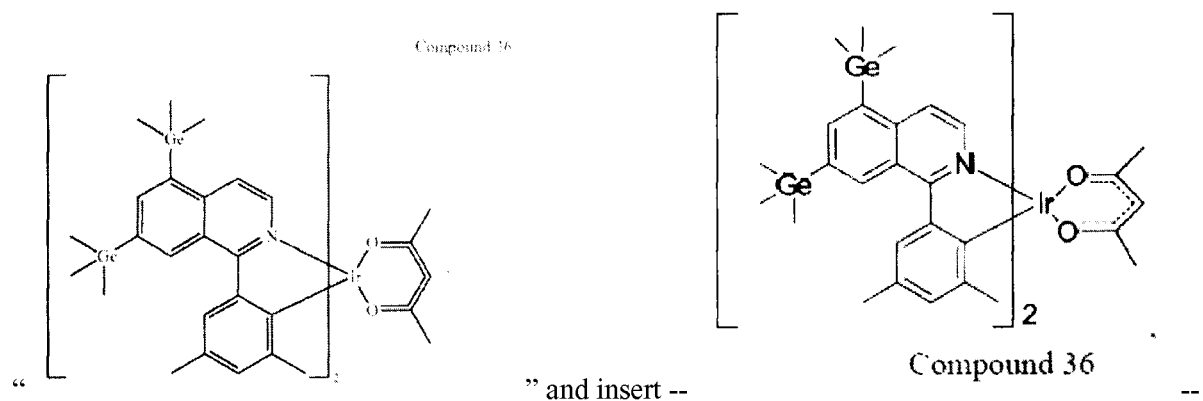" and insert --Compound 36--

CERTIFICATE OF CORRECTION (continued)
U.S. Pat. No. 9,512,355 B2

In Claim 20, Column 133, Lines 16-33, please delete

" and insert --

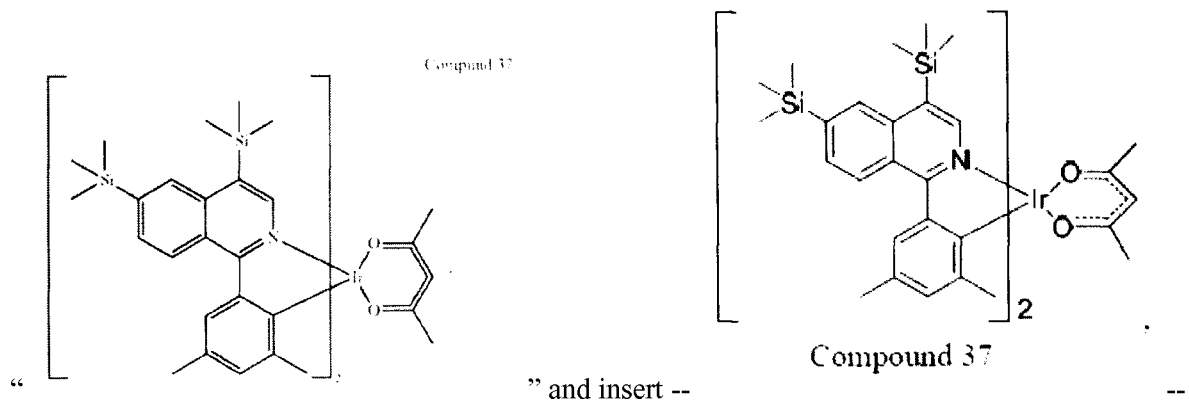

--

In Claim 20, Column 133, Lines 34-48, please delete

" and insert --

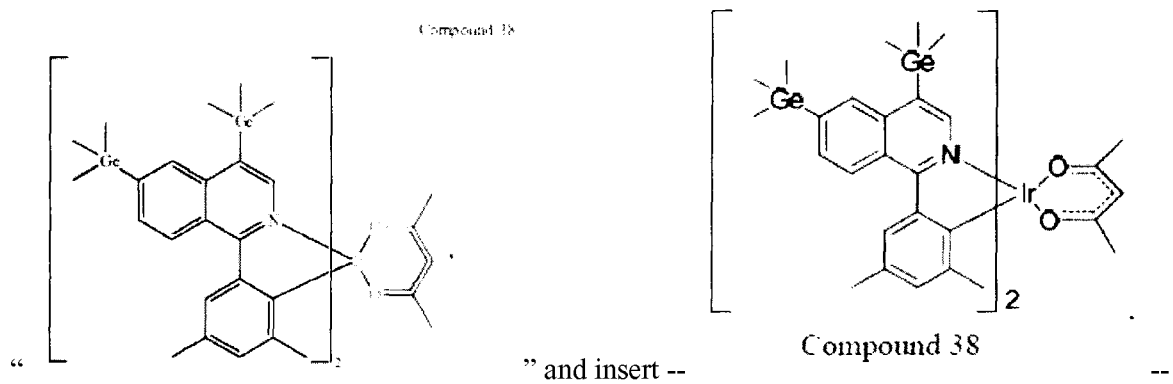

--

In Claim 20, Column 128, Lines 49-66, please delete

" and insert --

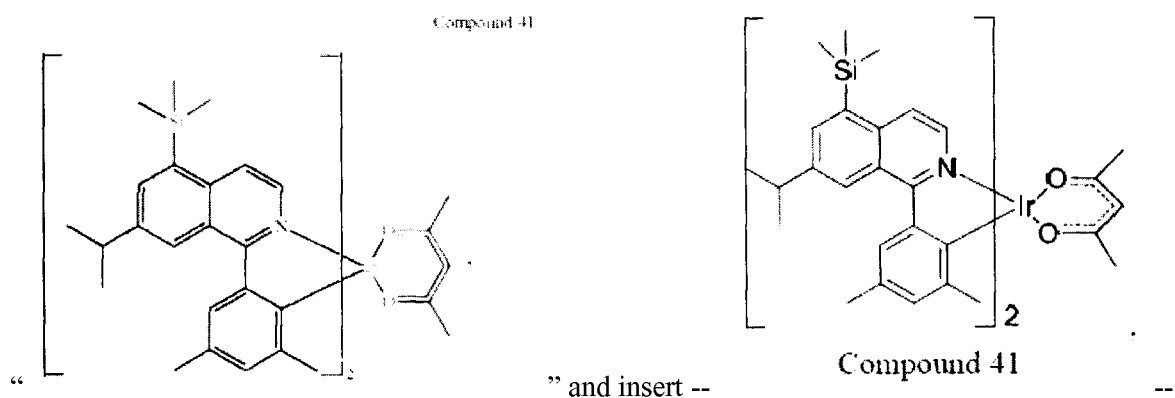

--

CERTIFICATE OF CORRECTION (continued)
U.S. Pat. No. 9,512,355 B2

In Claim 20, Column 134, Lines 1-16, please delete

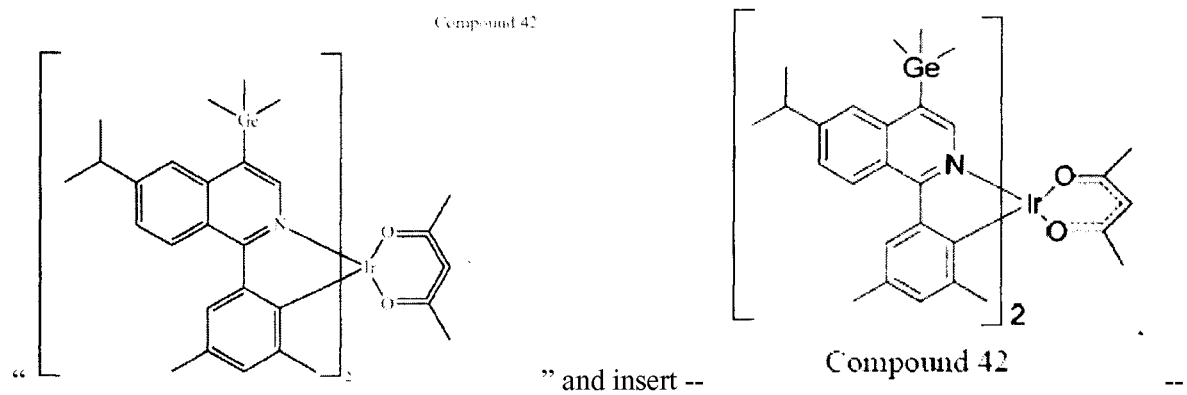

" and insert --

In Claim 20, Column 134, Lines 17-31, please delete

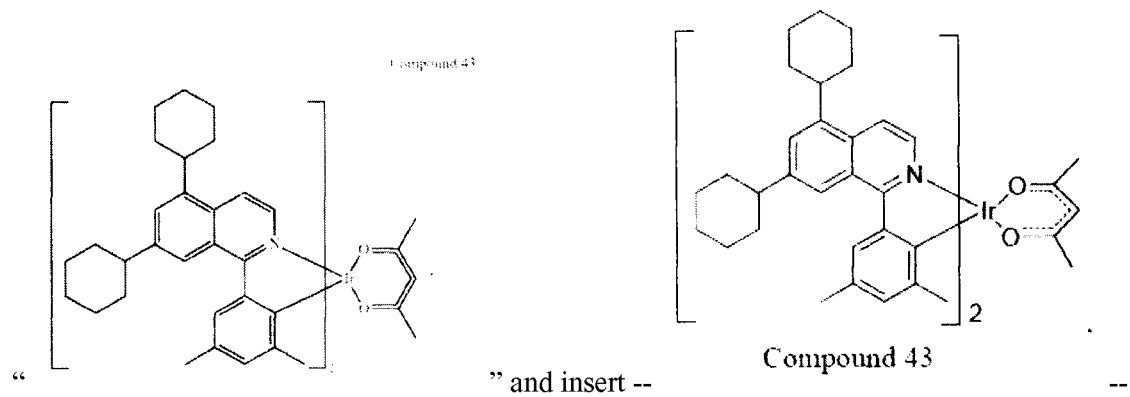

" and insert --

In Claim 20, Column 134, Lines 32-47, please delete

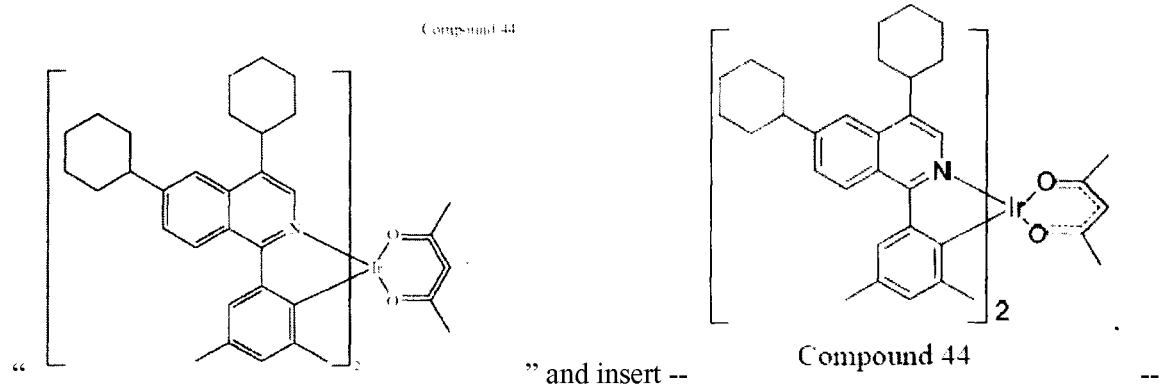

" and insert --

CERTIFICATE OF CORRECTION (continued)
U.S. Pat. No. 9,512,355 B2

In Claim 20, Column 134, Lines 48-64, please delete

" 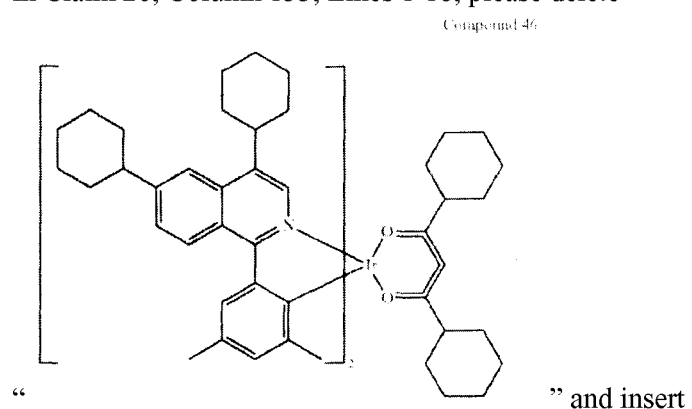 " and insert --

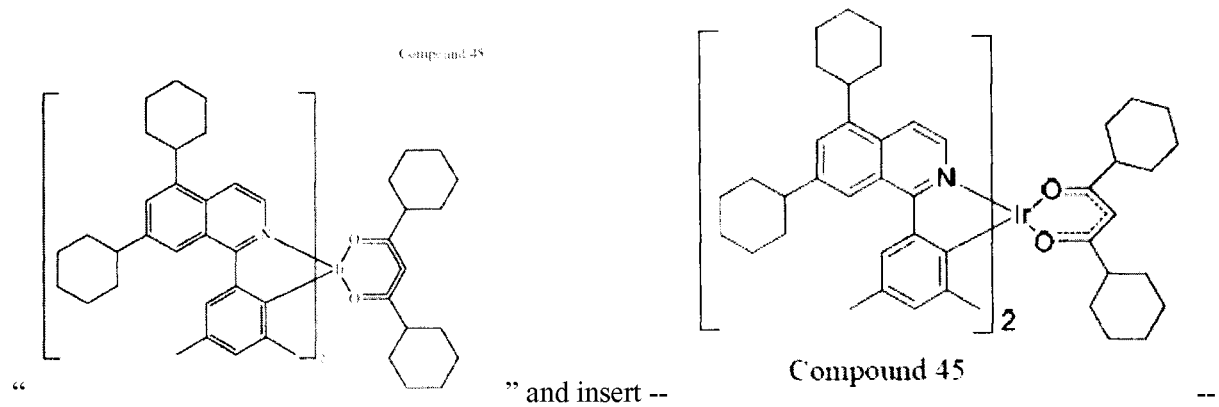

Compound 45

--

In Claim 20, Column 135, Lines 1-18, please delete

" 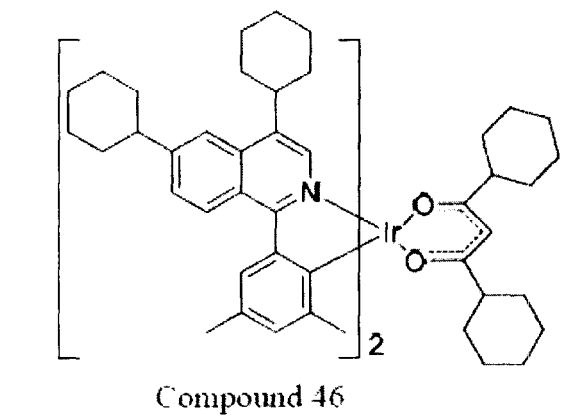 " and insert

Compound 46

-- --